(12) United States Patent
Arnold et al.

(10) Patent No.: US 10,214,513 B2
(45) Date of Patent: Feb. 26, 2019

(54) HETEROCYCLIC COMPOUNDS USEFUL FOR KINASE INHIBITION

(71) Applicant: Amitech Therapeutic Solutions, Inc., La Jolla, CA (US)

(72) Inventors: Lee Daniel Arnold, Mt. Sinai, NY (US); Eric A. Murphy, Encinitas, CA (US)

(73) Assignee: AMITECH THERAPEUTIC SOLUTIONS, INC., La Jolla, CA (US)

( * ) Notice: Subject to any disclaimer, the term of this patent is extended or adjusted under 35 U.S.C. 154(b) by 0 days.

(21) Appl. No.: 14/965,334

(22) Filed: Dec. 10, 2015

(65) Prior Publication Data
US 2016/0096824 A1    Apr. 7, 2016

Related U.S. Application Data

(62) Division of application No. 14/620,527, filed on Feb. 12, 2015, now Pat. No. 9,212,151, which is a division of application No. 13/636,298, filed as application No. PCT/US2011/029879 on Mar. 24, 2011, now Pat. No. 8,957,216.

(60) Provisional application No. 61/317,223, filed on Mar. 24, 2010.

(51) Int. Cl.

| | | |
|---|---|---|
| *C07D 403/14* | (2006.01) | |
| *C07D 403/12* | (2006.01) | |
| *A61K 31/4196* | (2006.01) | |
| *A61K 31/4439* | (2006.01) | |
| *C07D 401/12* | (2006.01) | |
| *C07D 401/14* | (2006.01) | |
| *C07D 409/14* | (2006.01) | |
| *C07D 413/12* | (2006.01) | |
| *C07D 487/04* | (2006.01) | |
| *C07D 249/14* | (2006.01) | |
| *C07D 413/14* | (2006.01) | |
| *C07D 417/12* | (2006.01) | |
| *C07D 471/04* | (2006.01) | |
| *C07D 487/22* | (2006.01) | |
| *A61N 5/10* | (2006.01) | |
| *C12N 5/09* | (2010.01) | |
| *A61K 31/4709* | (2006.01) | |
| *A61K 31/4725* | (2006.01) | |
| *A61K 31/506* | (2006.01) | |
| *A61K 31/517* | (2006.01) | |
| *A61K 31/519* | (2006.01) | |
| *A61K 45/06* | (2006.01) | |

(52) U.S. Cl.
CPC ........ *C07D 403/12* (2013.01); *A61K 31/4196* (2013.01); *A61K 31/4439* (2013.01); *A61K 31/4709* (2013.01); *A61K 31/4725* (2013.01); *A61K 31/506* (2013.01); *A61K 31/517* (2013.01); *A61K 31/519* (2013.01); *A61K 45/06* (2013.01); *A61N 5/10* (2013.01); *C07D 249/14* (2013.01); *C07D 401/12* (2013.01); *C07D 401/14* (2013.01); *C07D 403/14* (2013.01); *C07D 409/14* (2013.01); *C07D 413/12* (2013.01); *C07D 413/14* (2013.01); *C07D 417/12* (2013.01); *C07D 471/04* (2013.01); *C07D 487/04* (2013.01); *C07D 487/22* (2013.01); *C12N 5/0693* (2013.01); *C12N 2501/48* (2013.01)

(58) Field of Classification Search
CPC .. C07D 403/12; C07D 487/22; C07D 413/14; C07D 417/12; C07D 471/04; C07D 249/14; C07D 409/14; C07D 401/14; C07D 413/12; C07D 401/12; C07D 403/14; C07D 487/04; A61K 31/506; A61K 31/4725; A61K 31/4709; A61K 31/519; A61K 45/06; A61K 31/517; A61K 31/4439; A61K 31/4196; C12N 5/0693; C12N 2501/48; A61N 5/10
See application file for complete search history.

(56) References Cited

U.S. PATENT DOCUMENTS

| | | | |
|---|---|---|---|
| 3,598,122 A | 8/1971 | Zaffaroni | |
| 3,598,123 A | 8/1971 | Zaffaroni | |
| 3,710,795 A | 1/1973 | Higuchi et al. | |
| 3,731,683 A | 5/1973 | Zaffaroni | |
| 3,742,951 A | 7/1973 | Zaffaroni | |
| 3,814,097 A | 6/1974 | Ganderton et al. | |
| 3,921,636 A | 11/1975 | Zaffaroni | |
| 3,972,995 A | 8/1976 | Tsuk et al. | |
| 3,993,072 A | 11/1976 | Zaffaroni | |
| 3,993,073 A | 11/1976 | Zaffaroni | |
| 3,996,934 A | 12/1976 | Zaffaroni | |
| 4,031,893 A | 6/1977 | Kaplan et al. | |
| 4,031,894 A | 6/1977 | Urquhart et al. | |
| 4,060,084 A | 11/1977 | Chandrasekaran et al. | |
| 4,069,307 A | 1/1978 | Higuchi et al. | |
| 4,077,407 A | 3/1978 | Theeuwes et al. | |
| 4,201,211 A | 5/1980 | Chandrasekaran et al. | |
| 4,230,105 A | 10/1980 | Harwood | |
| 4,292,299 A | 9/1981 | Suzuki et al. | |
| 4,292,303 A | 9/1981 | Keith et al. | |
| 4,476,116 A | 10/1984 | Anik | |
| 5,116,817 A | 5/1992 | Anik | |
| 5,336,168 A | 8/1994 | Sibalis | |
| 5,358,489 A | 10/1994 | Wyrick | |

(Continued)

FOREIGN PATENT DOCUMENTS

| | | |
|---|---|---|
| CN | 101044125 A | 9/2007 |
| CN | 101600712 A | 12/2009 |

(Continued)

OTHER PUBLICATIONS

Ashour. Synthesis of some phenoxymethylbenzimidazole derivatives as potential antibacterial and antifungal agents. Alexandria Journal of Pharmaceutical Sciences. 5(1):16-20 Accession No. 1992:55400 (1991).

(Continued)

*Primary Examiner* — Robert H Havlin
(74) *Attorney, Agent, or Firm* — Wilson Sonsini Goodrich & Rosati

(57) ABSTRACT

Provided herein are compounds useful for kinase inhibition.

3 Claims, No Drawings

(56) References Cited

U.S. PATENT DOCUMENTS

| | | | |
|---|---|---|---|
| 5,540,664 | A | 7/1996 | Wyrick |
| 5,665,071 | A | 9/1997 | Wyrick |
| 5,665,378 | A | 9/1997 | Davis et al. |
| 5,695,472 | A | 12/1997 | Wyrick |
| 5,837,280 | A | 11/1998 | Kenealy et al. |
| 5,869,090 | A | 2/1999 | Rosenbaum |
| 5,962,685 | A | 10/1999 | Ueda et al. |
| 6,391,452 | B1 | 5/2002 | Antonsen et al. |
| 6,923,983 | B2 | 8/2005 | Morgan et al. |
| 6,929,801 | B2 | 8/2005 | Klose et al. |
| 6,946,144 | B1 | 9/2005 | Jordan |
| 8,329,739 | B2 | 12/2012 | Shibutani et al. |
| 8,957,216 | B2 | 2/2015 | Arnold et al. |
| 9,212,151 | B2 | 12/2015 | Arnold et al. |
| 2006/0079526 | A1 | 4/2006 | Wrasidlo et al. |

FOREIGN PATENT DOCUMENTS

| | | |
|---|---|---|
| EP | 2128156 A1 | 12/2009 |
| JP | 2006503081 A | 1/2006 |
| JP | 2007145828 A | 6/2007 |
| JP | 2008510839 A | 4/2008 |
| JP | 2008266294 A | 11/2008 |
| JP | 2008266295 A | 11/2008 |
| JP | 2009541424 A | 11/2009 |
| JP | 2013518909 A | 5/2013 |
| JP | 5540227 B2 | 7/2014 |
| JP | 6065183 B2 | 1/2017 |
| WO | WO-9604278 A1 | 2/1996 |
| WO | WO-03032916 A2 | 4/2003 |
| WO | WO-2004032882 A2 | 4/2004 |
| WO | WO-2005004818 A2 | 1/2005 |
| WO | WO-2005087297 A1 | 9/2005 |
| WO | WO-2006023864 A1 | 3/2006 |
| WO | WO-2006023865 A1 | 3/2006 |
| WO | WO-2006024034 A1 | 3/2006 |
| WO | WO-2006083760 A1 | 8/2006 |
| WO | WO-2007100646 A1 | 9/2007 |
| WO | WO-2008093674 A1 | 8/2008 |
| WO | WO-2008093677 A1 | 8/2008 |
| WO | WO-2011097594 A2 | 8/2011 |

OTHER PUBLICATIONS

Englesbe et al. Concomitant blockade of platelet-derived growth factor receptors alpha and beta induces intimal atrophy in baboon PTFE grafts. J Vasc Surg 39:440-446 (2004).

Gaonkar et al. Synthesis and Antimicrobial Studies of a new Series of 2-{4-[2-(5-ethylpryridin-2-yl)ethoxy]phenyl}-5-substituted-1,3,4-oxadiazoles. European Journal of Medicinal Chemistry 41:(7):841-846 (Jul. 1, 2006).

Hirpara et al. 2-Methoxy-5-methylphenyl thiosemicarba-zide : A versatile molecule for the synthesis of thiadiazoles and imidazolinones possessing multiple biological activities. Indian J. Chem. 42:1172-1175 (2003) (Abstract).

IUPAC 1974 Recommendations for Section E. Fundamental Stereochemistry Pure Appl. Chem 45:13-30 (1976).

Kubinyi. 3D QSAR in Drug Design: Ligand-Protein Interactions and Molecular Similarity. (vol. 2-3, Springer, 800 pages). pp. 243-244 provided (1998).

Li et al. Ablation of MEK kinase 1 suppresses intimal hyperplasia by impairing smooth muscle cell migration and urokinase plasminogen activator expression in a mouse blood-flow cessation model. Circulation 111:1672-1678 (2005).

Malerich et al. Diamino-1,2,4-triazole derivatives are selective inhibitors of TYK2 and JAK1 over JAK2 and JAK3. Bioorg. Med. Chem. Lett. 20:7454-7457 (2010).

Matysiak. QSAR of Antiproliferative Activity of N-Substituted 2-Amino-5(2,4-dihydroxyphenyl)-1,3,4-thiadiazoles in Various Human Cancer Cells. QSAR & Combinatorial Science 27(5):607-617 (2008).

Murphy et al. Disruption of angiogenesis and tumor growth with an orally active drug that stabilizes the inactive state of PDGFRbeta/B-RAF. PNAS USA 107:4299-4304 (2010).

Ouyang et al. Synthesis and structure-activity relationships of 1,2,4-triazoles as a novel class of potent tubulin polymerization inhibitors. Bioorganic & Medicinal Chemistry Letters 15:5154-5159 (2005).

PCT/US2011/029879 International Search Report and Written Opinion dated Dec. 28, 2011.

Pintucci et al. Anti-proliferative and anti-inflammatory effects of topical MAPK inhibition in arterialized vein grafts. FASEB J 20:398-400 (2006).

STN International. Pyridine, 3-chloro-2-(2-(5-(4-chlorophenyl)-1,3,4-oxadiazol-2-yl]phenoxy]-5-(trifluoromethyl)-, file Registry [online], published Nov. 22, 2000, [Feb. 9, 2015], CAS Registry No. 303997-37-7.

Terfloth et al. Electronic Screening: Lead Finding From Database Mining. Wermuth, The Practice of Medicinal Chemistry, 2d ed. 768 pages. Chs. 9-10 provided (2003).

U.S. Appl. No. 13/636,298 Office Action dated Oct. 17, 2013.
U.S. Appl. No. 13/636,298 Final Office Action dated Jun. 10, 2014.

HETEROCYCLIC COMPOUNDS USEFUL FOR KINASE INHIBITION

CROSS-REFERENCE

This patent application is a divisional of U.S. patent application Ser. No. 14/620,527, filed Feb. 12, 2015, issues as U.S. Pat. No. 9,212,151 on Dec. 15, 2015; which is a divisional of U.S. patent application Ser. No. 13/636,298, filed Dec. 3, 2012, issued as U.S. Pat. No. 8,957,216 on Feb. 17, 2015; which is a U.S. national phase application of PCT Application No. PCT/US2011/029879, filed on Mar. 24, 2011; and claims the benefit of U.S. Provisional Patent Application No. 61/317,223, filed Mar. 24, 2010, which applications are incorporated herein by reference in their entirety.

BACKGROUND OF THE INVENTION

Kinases regulate fundamental processes in cancer and other hyperproliferative disorders including aspects such as proliferation, migration and metastasis, neovascularization, and chemoresistance. Accordingly, kinase inhibitors have been a major focus of drug development and several kinase inhibitors are now approved for various cancer indications. Typically, kinase inhibitors are selected via high throughput screening using catalytic kinase domains at low ATP concentration and this process often yields ATP mimetics that lack specificity and/or function poorly in cells where ATP levels are high.

SUMMARY OF THE INVENTION

In accordance with the present invention, there is provided a compound having the structure (I) or an N-oxide, N,N'-dioxide, N,N',N"-trioxide, or a pharmaceutically acceptable salt thereof:

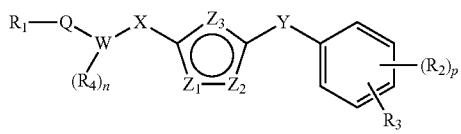

wherein:

Q is O or S;

W is $C_6$-$C_{12}$ aryl or $C_3$-$C_{12}$ heteroaryl having 1-3 heteroatoms;

each of X and Y is independently absent or a NH;

each of $Z_1$ and $Z_2$ is independently selected from a group consisting of CH, N, and $NR_5$, wherein $R_5$ is hydrogen or lower alkyl;

$Z_3$ is O, S, N, or $NR_5$, wherein $R_5$ is hydrogen or lower alkyl;

$R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;

each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;

$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NH$COR_6$, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; p=0-4; and n is 1 or 2.

In some embodiments, there is provided a compound having the structure (II) or an N-oxide, N,N'-dioxide, N,N', N"-trioxide, or a pharmaceutically acceptable salt thereof:

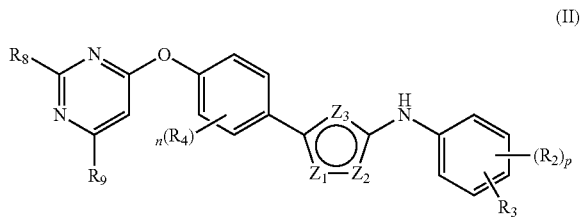

or an N-oxide, N,N'-dioxide, N,N',N"-trioxide, or a pharmaceutically acceptable salt thereof:

wherein each of $Z_1$ and $Z_2$ is independently selected from a group consisting of CH, N, and $NR_5$, wherein $R_5$ is hydrogen or lower alkyl;

$Z_3$ is O, S, N, or $NR_5$, wherein $R_5$ is hydrogen or lower alkyl;

each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;

$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NH$COR_6$, —$NH_2$, —$NR_6R_7$, —$SR_6$, —$S(O)R_6$, $S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; n is 1 or 2; and $R_8$ and $R_9$ is independently selected from the group consisting of hydrogen, halogen, optionally substituted $C_1$-$C_6$ alkyl, —$CF_3$, —OH, optionally substituted $C_1$-$C_6$ alkoxy, —$NR_{10}R_{11}$, and —$SO_mR_{12}$, wherein $R_{10}$ and $R_{11}$ are independently selected from a group consisting of hydrogen, optionally substituted $C_1$-$C_6$ alkyl, —$SO_2R_{12}$, —$S(O)R_{12}$, and —$COR_{12}$, and $R_{12}$ is an optionally substituted alkyl or an optional substituted $C_3$-$C_{12}$ heteroaryl having 1-3 heteroatoms and m is 0-2.

In other embodiments, there is provided a compound having the structure (III) or an N-oxide, N,N'-dioxide, N,N',N"-trioxide, or a pharmaceutically acceptable salt thereof:

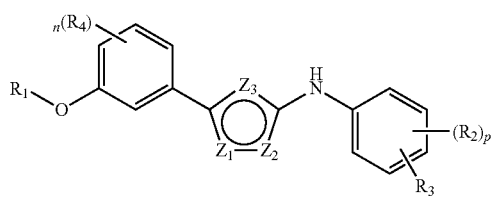

(III)

wherein
- each of $Z_1$ and $Z_2$ is independently selected from a group consisting of CH, N, and $NR_5$, wherein $R_5$ is hydrogen or lower alkyl; and
- $Z_3$ is O, S, N, or $NR_5$, wherein $R_5$ is hydrogen or lower alkyl.
- $R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;
- each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;
- $R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NH-$COR_6$, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; p=0-4; and n is 1 or 2.

In some embodiments, there is provided a compound having the structure (IV) or an N-oxide, N,N'-dioxide, N,N',N''-trioxide, or a pharmaceutically acceptable salt thereof:

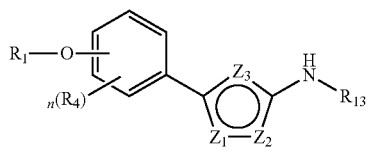

(IV)

wherein:
- each of $Z_1$ and $Z_2$ is independently selected from a group consisting of CH, N, and $NR_5$, wherein $R_5$ is hydrogen or lower alkyl;
- $Z_3$ is O, S or $NR_5$, wherein $R_5$ is hydrogen or lower alkyl;
- $R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;
- $R_4$ is independently selected from a group consisting of hydrogen, halogen, $C_1$-$C_6$ alkyl, —OH, —$NO_2$, —CN, $C_1$-$C_6$ alkoxy, —$NHSO_2R_6$, —$SO_2NHR_6$, —NH-$COR_6$, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl and n is 1 or 2; and
- $R_{13}$ is an optionally substituted —N—($C_1$-$C_6$ alkyl)pyrazolyl or selected from a group consisting of the following structures:

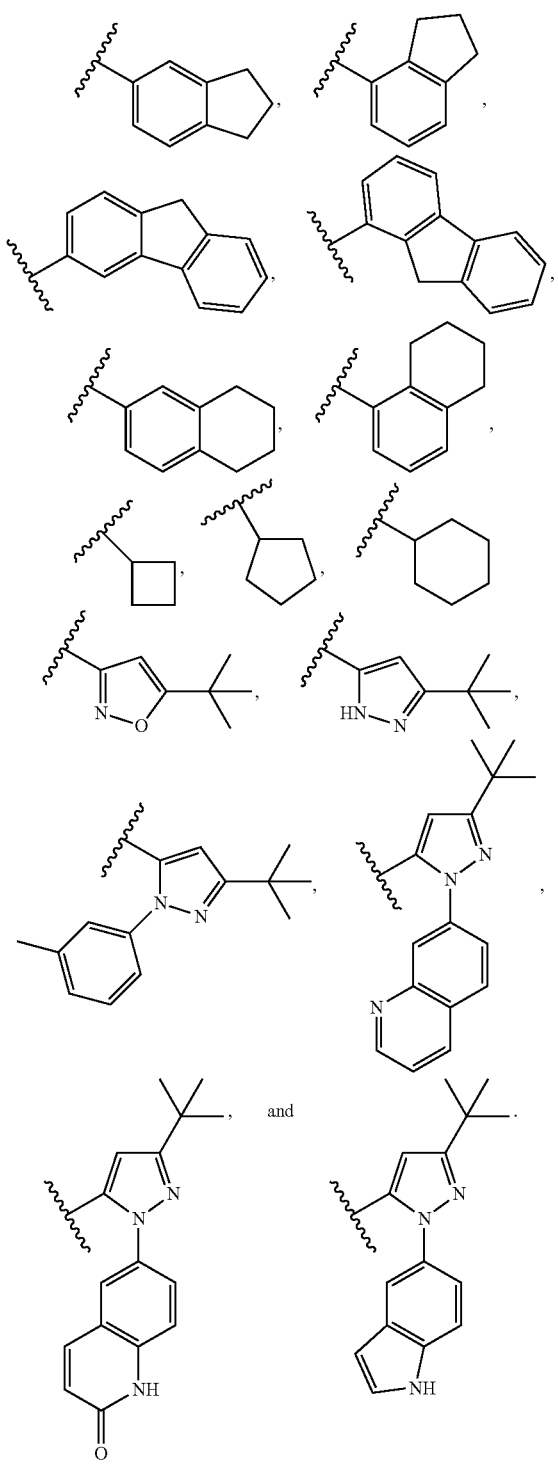

In other embodiments, there is provided a compound having the structure (V) or an N-oxide, N,N'-dioxide, N,N', N''-trioxide, or a pharmaceutically acceptable salt thereof:

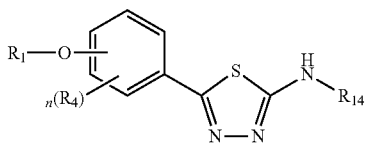

(V)

wherein:
R$_1$ is an unsubstituted or a substituted C$_3$-C$_{12}$ heteroaryl having 1-3 heteroatoms or an alkyl substituted with an unsubstituted or a substituted C$_3$-C$_{12}$ heteroaryl having 1-3 heteroatoms;
R$_4$ is independently selected from a group consisting of hydrogen, halogen, C$_1$-C$_6$ alkyl, —OH, —NO$_2$, —CN, C$_1$-C$_6$ alkoxy, —NHSO$_2$R$_6$, —SO$_2$NHR$_6$, —NHCOR$_6$, —NH$_2$, —NR$_6$R$_7$, —SR$_6$, —S(O)R$_6$, —S(O)$_2$R$_6$, —CO$_2$R$_6$, and —CONR$_6$R$_7$, wherein R$_6$ and R$_7$ are independently selected from a group consisting of hydrogen, and an optionally substituted C$_1$-C$_6$ alkyl; n is 1 or 2; and
R$_{14}$ is selected from a group consisting of an optionally substituted C$_1$-C$_{12}$ alkyl, an optionally substituted C$_3$-C$_{12}$ cycloalkyl, an optionally substituted C$_3$-C$_{10}$ heterocycle having 1-3 heteroatoms, an optionally substituted C$_6$-C$_{12}$ aryl, and an optional substituted C$_3$-C$_{12}$ heteroaryl having 1-3 heteroatoms.

In some embodiments, there are provided methods for suppressing, preventing or inhibiting lymphangiogenesis, neovascularization, recruitment of periendothelial cells, angiogenesis, hyderproliferative disorder, fibrotic lesion, ocular disorder and/or growth of a tumor. The methods comprise contacting the tumor with a compound of structures I-V or Ia-Va or a pharmaceutical composition comprising the compound of structures I-V or Ia-Va thereof.

In some embodiments, there are also provided methods for treating cancer, restenosis, intimal hyperplasia, fibrotic diseases or angiogenesis-dependent disorder in a human subject. The methods comprise administering to a patient in need a compound of structures I-V or Ia-Va or a pharmaceutical composition comprising the compound of structures I-V or Ia-Va thereof.

In certain embodiments, there are provided methods for preventing inhibition of ASK1-mediated apoptosis in a cell, sensitizing a cell to an extrinsic stress or inhibiting MEK1/2- and/or ERK1/2-mediated cellular proliferation or migration. The methods comprise contacting the tumor with a compound of structures I-V or Ia-Va or a pharmaceutical composition comprising the compound of structures I-V or Ia-Va thereof.

In some embodiments, there are provided methods of inhibiting a protein kinase comprising contacting the protein kinase with an inhibitory concentration of a compound of structures I-V or Ia-Va or a pharmaceutical composition comprising the compound of structures I-V or Ia-Va thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

In the case of 1,2,4-triazoles, there exist three tautomeric structures, as shown below:

Which tautomeric structure is prevailing depends on the substituents on the triazole moiety and on the reaction conditions. As known to those having ordinary skill in the art, typically, 1H-1,2,4-triazole is the most common tautomeric form, especially if an amino substituent is attached to the ring. Even though all three tautomeric structures can be present and interconvert, all the generic structures and all the examples having 1,2,4-triazole moiety are shown herein in one tautomeric form, such as 4H-1,2,4-triazole, for simplicity and for the comparison with its direct analogues, such as examples containing 1,3,4-oxadiazole moiety. Using only 4H-tautomeric form to draw the structures for the sake of simplicity, does not imply that the compounds provided herein exist in that particular tautomeric form.

In accordance with the present invention, there are provided a compound having the structure (I) or an N-oxide, N,N'-dioxide, N,N',N''-trioxide, or a pharmaceutically acceptable salt thereof:

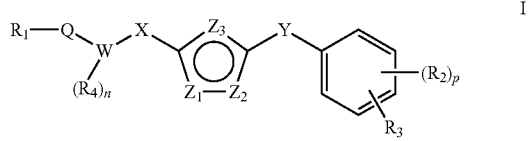

I wherein:
Q is O or S;
W is C$_6$-C$_{12}$ aryl or C$_3$-C$_{12}$ heteroaryl having 1-3 heteroatoms;
each of X and Y is independently absent or a NH;
each of Z$_1$ and Z$_2$ is independently selected from a group consisting of CH, N, and NR$_5$, wherein R$_5$ is hydrogen or lower alkyl;
Z$_3$ is O, S, N, or NR$_5$, wherein R$_5$ is hydrogen or lower alkyl;
R$_1$ is an unsubstituted or a substituted C$_3$-C$_{12}$ heteroaryl having 1-3 heteroatoms or an alkyl substituted with an unsubstituted or a substituted C$_3$-C$_{12}$ heteroaryl having 1-3 heteroatoms;

each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;

$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NH-$COR_6$, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; p=0-4; and n is 1 or 2.

In accordance with the present invention, there are also provided deuterium-enriched compounds having the structure (I) or an N-oxide, N,N'-dioxide, N,N',N''-trioxide, or a pharmaceutically acceptable salt thereof. The hydrogens present on the compounds of structure (I) have different capacities for exchange with deuterium. Some are easily exchangeable under physiological conditions (e.g. any acidic hydrogens) which may be changed during or after the synthesis of the final compounds. Some are not easily exchangeable and may be incorporated by the use of deuterated starting materials or intermediates during the construction of the final compounds.

Some embodiments further provide a compound having the structure (I) or an N-oxide, N,N'-dioxide, N,N',N''-trioxide, or a pharmaceutically acceptable salt thereof, wherein $Z_3$ is O or S. In some embodiments, Q is S. In other embodiments, Q is O. In certain embodiments, n is 2. In some embodiments, W is $C_3$-$C_{10}$ heterocycle having 1-3 heteroatoms. In certain embodiment, W is selected from the group consisting of thiophene, pyridine, pyridazine, pyrimidine and pyrazine. For example, the compound is selected from the group consisting of

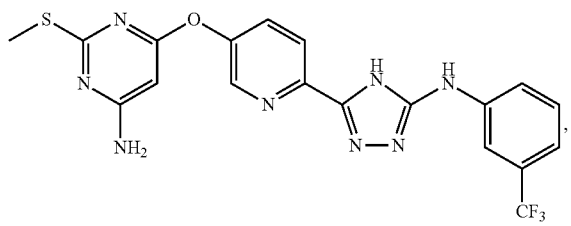

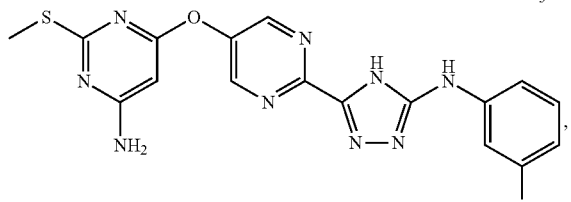

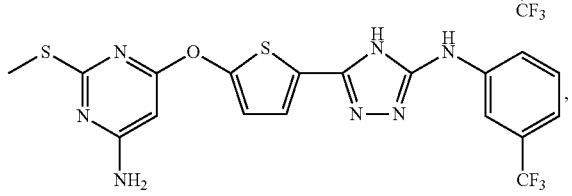

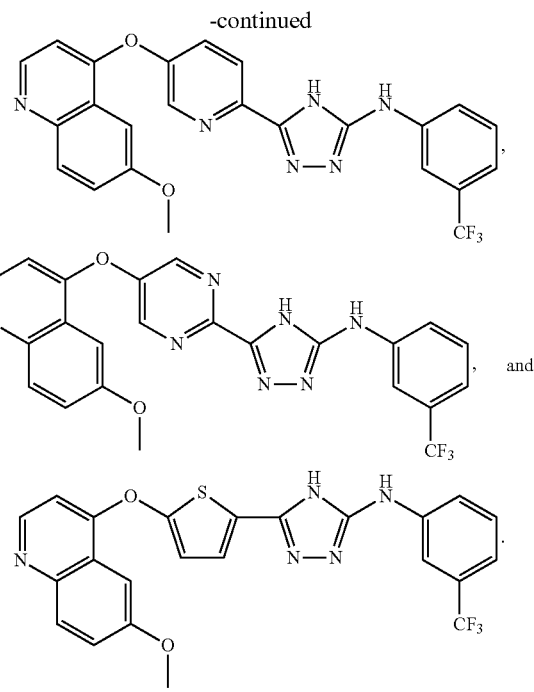

In other embodiments, W is $C_6$-$C_{12}$ aryl. In certain embodiments, W is phenyl. In certain embodiments, $Z_3$ is O or S, and each $R_2$ and $R_3$ are independently selected from a group consisting of a hydrogen, a $C_1$-$C_6$ alkoxy, an optionally substituted $C_1$-$C_6$ alkyl, —$CF_3$, halogen, —CN, and —$CO_2R'$ wherein R' is hydrogen or $C_1$-$C_6$ alkyl; or, optionally, $R_2$ and $R_3$ are joined to form a five to seven membered carbocycle. In some embodiments, $R_1$ is an unsubstituted or a substituted $C_3$-$C_{12}$ heteroaryl having 1-3 heteroatoms. In certain embodiments, $R_1$ is an unsubstituted or a substituted pyridine. In certain embodiments, $R_1$ is an unsubstituted pyridine or a $C_1$-$C_6$ alkyl substituted pyridine. In certain embodiments, $R_1$ is an unsubstituted or a substituted pyrimidine. In some embodiments, the compounds have the structure (I) wherein $R_4$ is hydrogen. In some embodiments, the compound have the structure (I) wherein each $R_2$ and $R_3$ are independently selected from a group consisting of a $C_1$-$C_6$ alkyl, —$CF_3$, and halogen, wherein p is 0 or 1 or 2; or, optionally, $R_2$ and $R_3$ are joined to form a five to seven membered carbocycle.

In certain embodiments, the compound having structure (I) is selected from the group consisting of

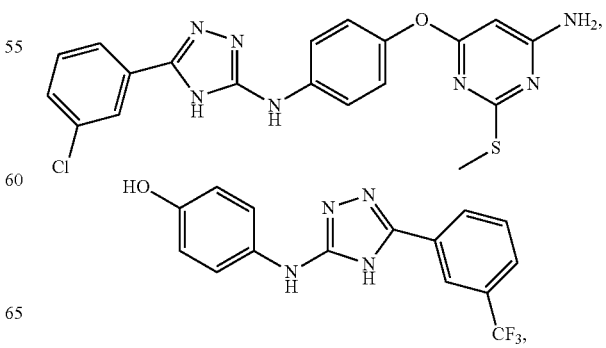

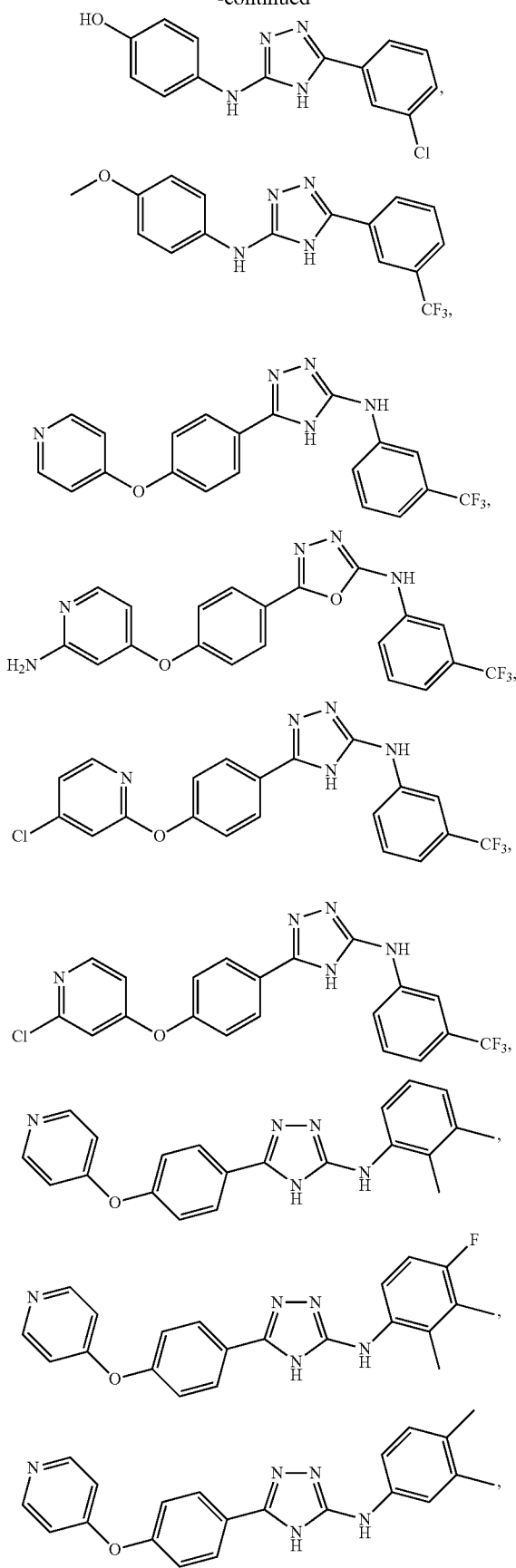
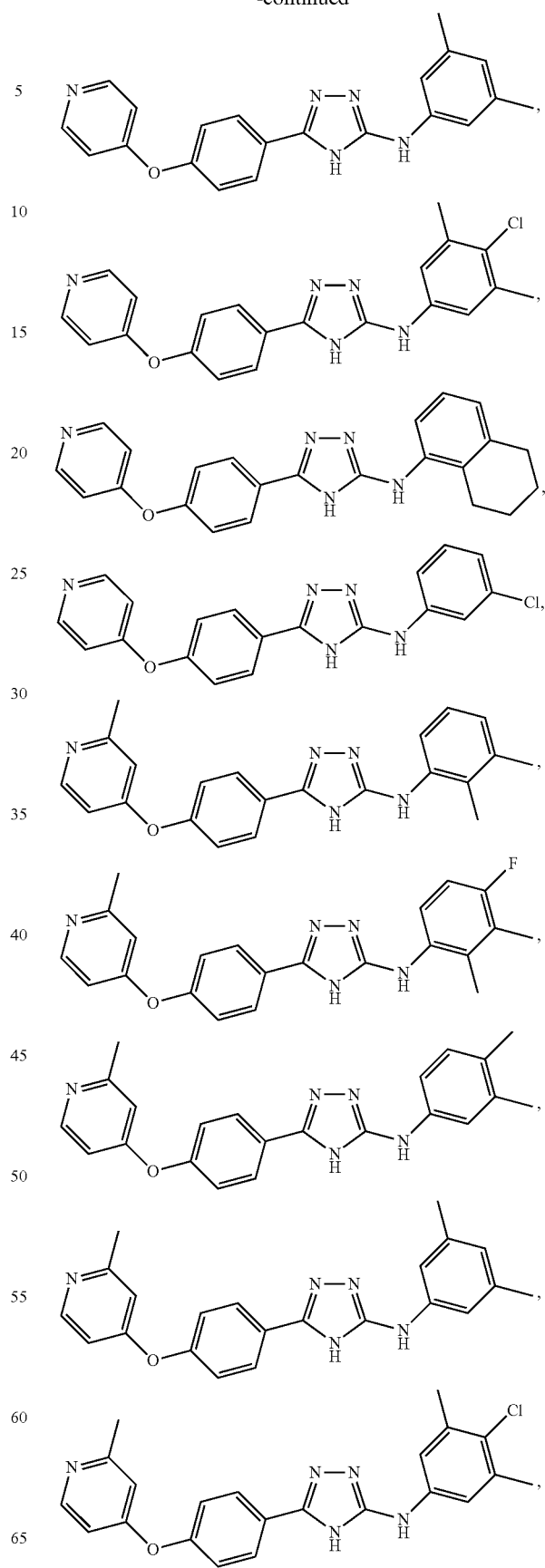

-continued
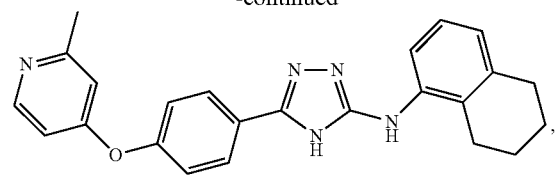
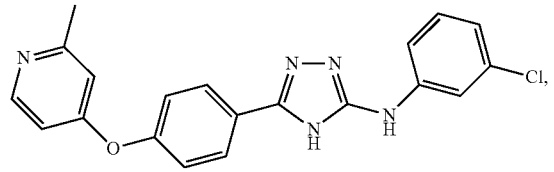
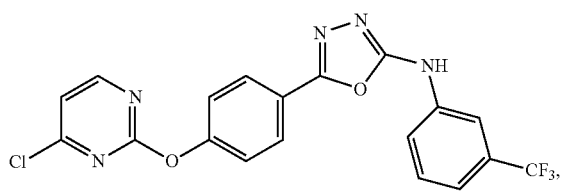
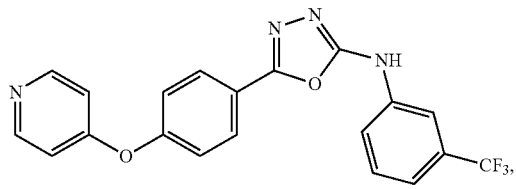
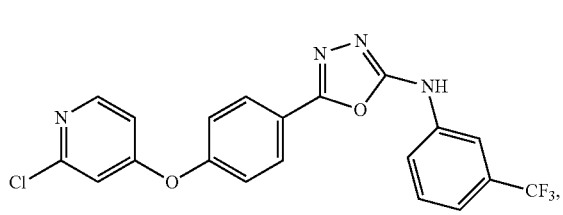
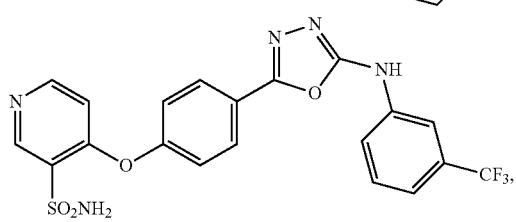
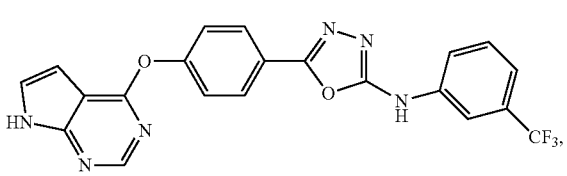
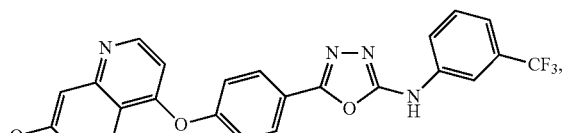
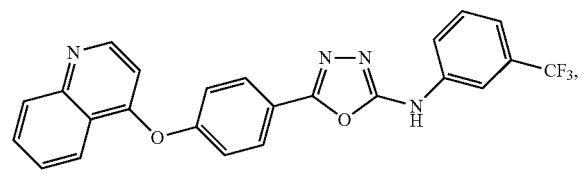
-continued
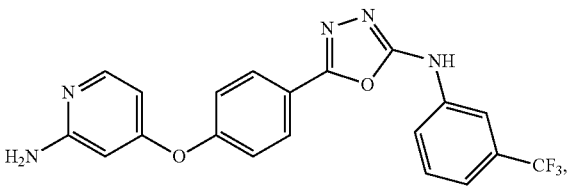
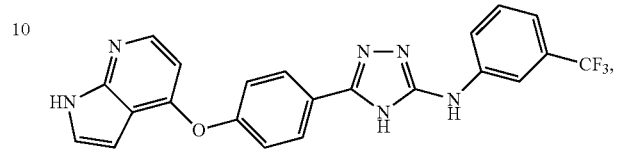
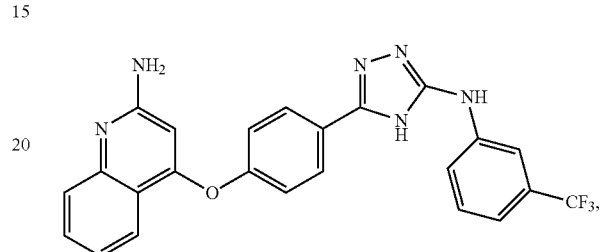
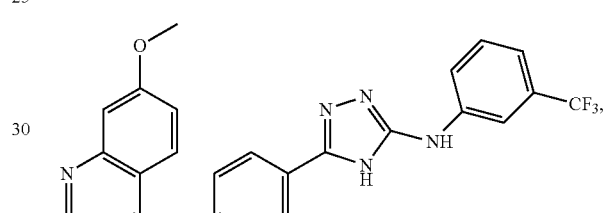
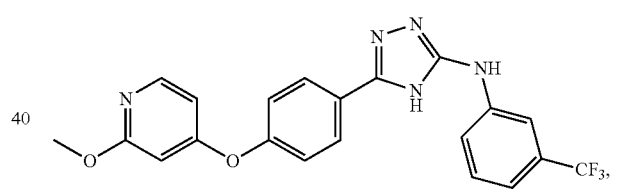
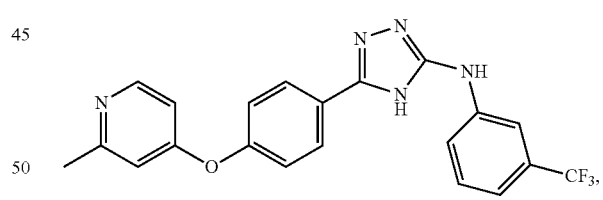
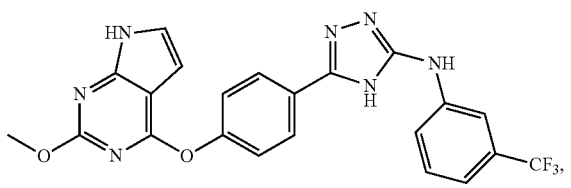
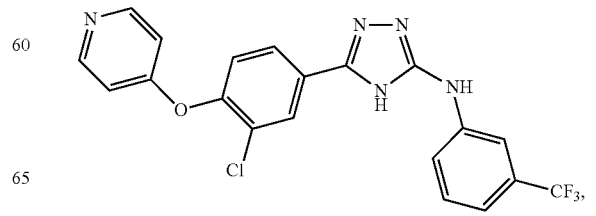

-continued
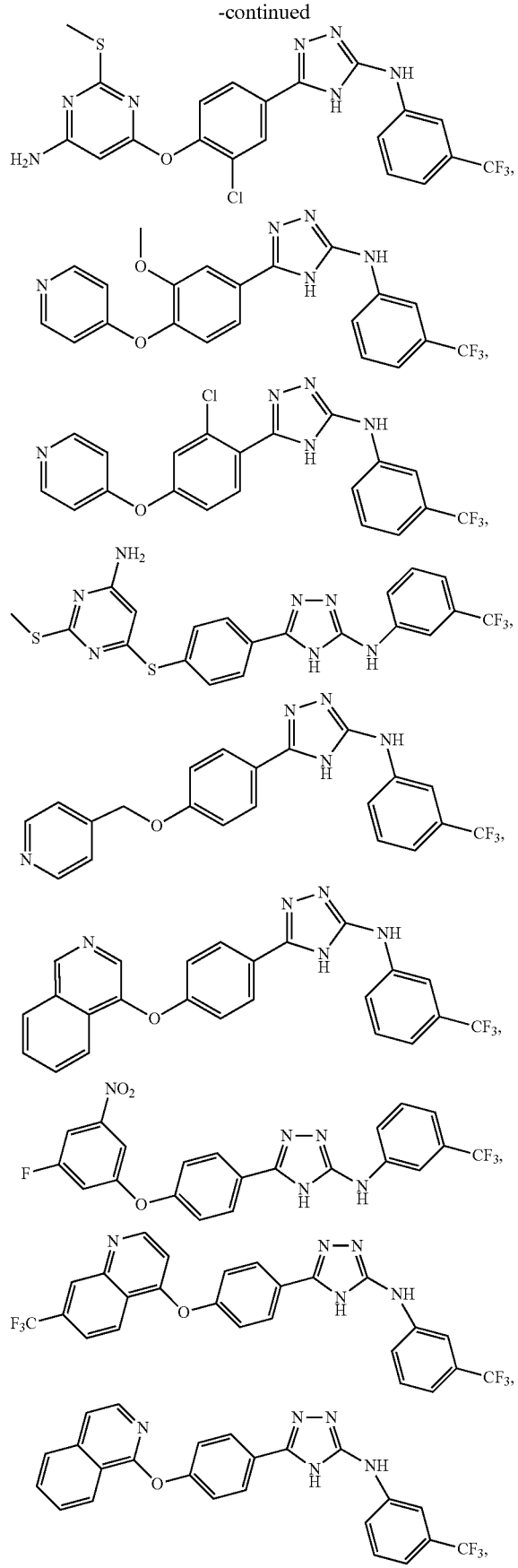
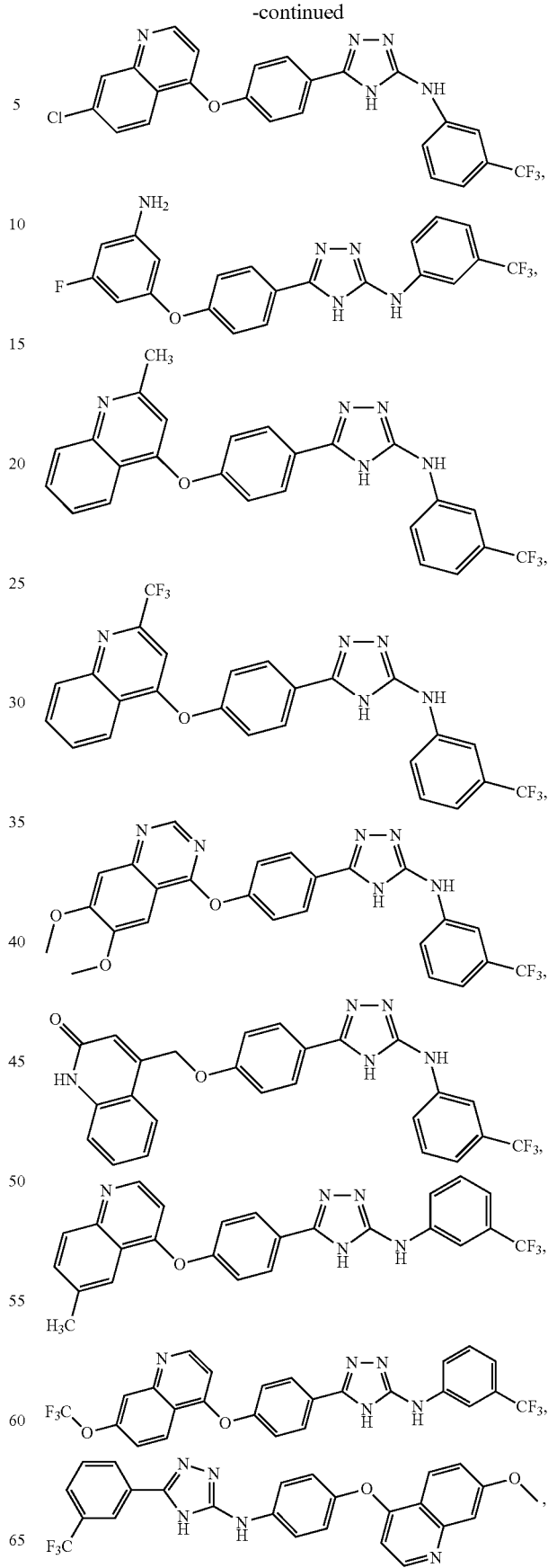

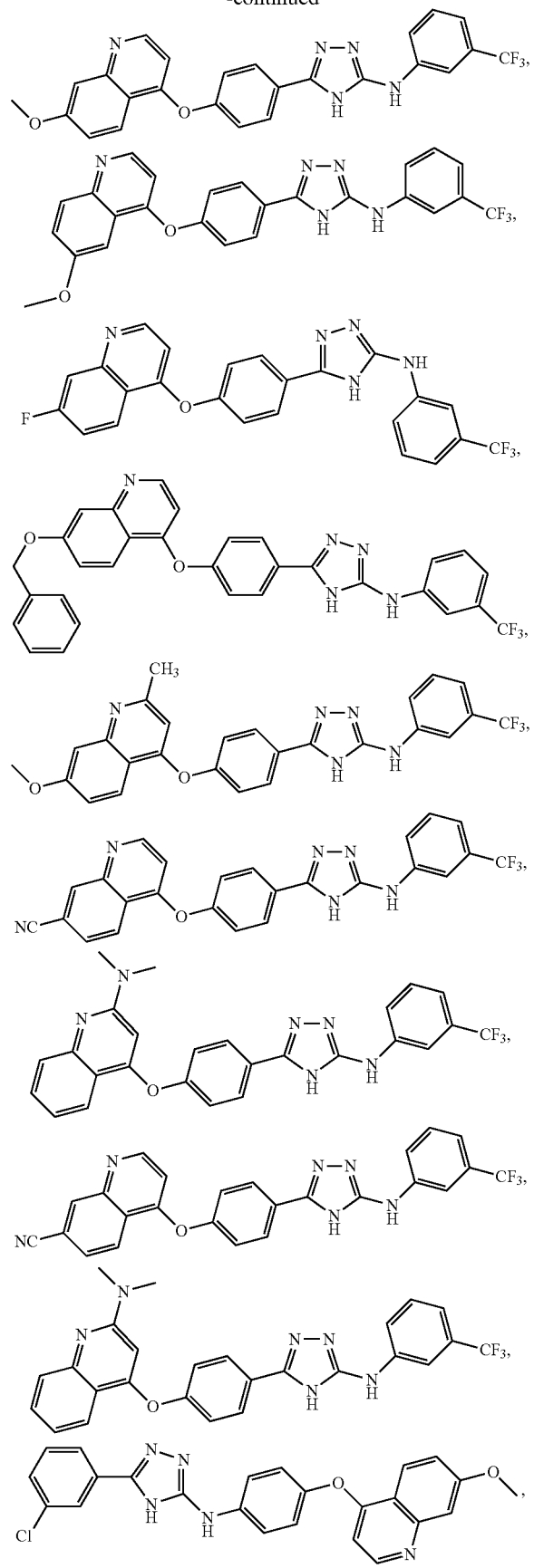
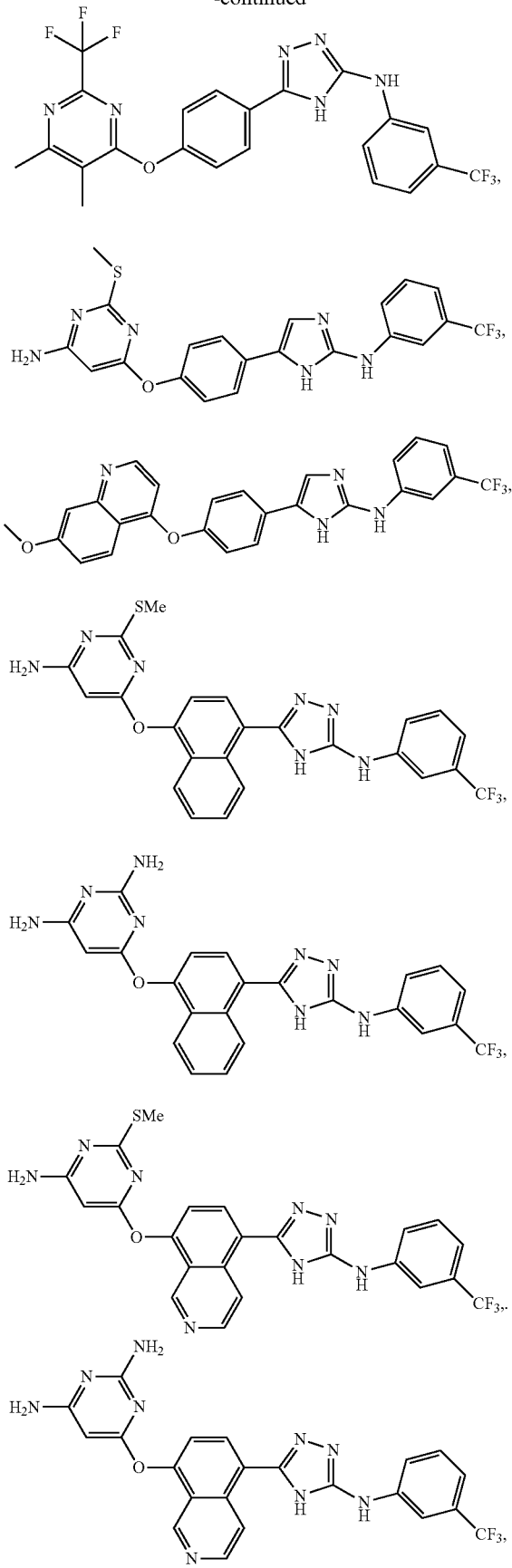

-continued
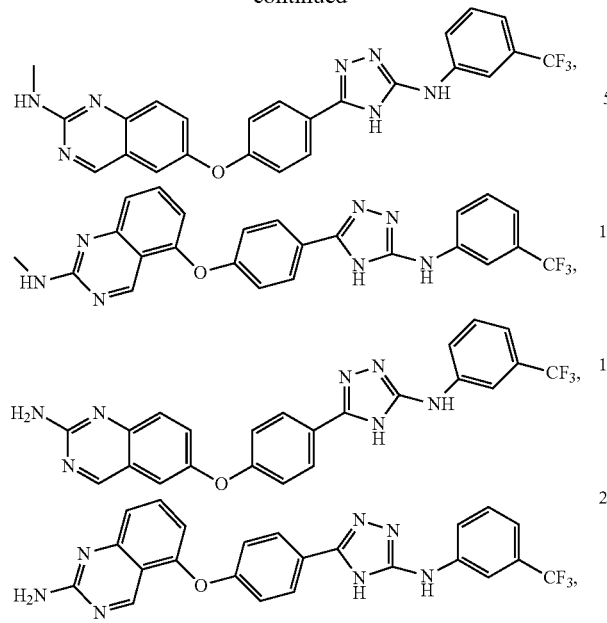
and the like.
In some embodiments, there are provided compounds having structure (I) selected from the group consisting of
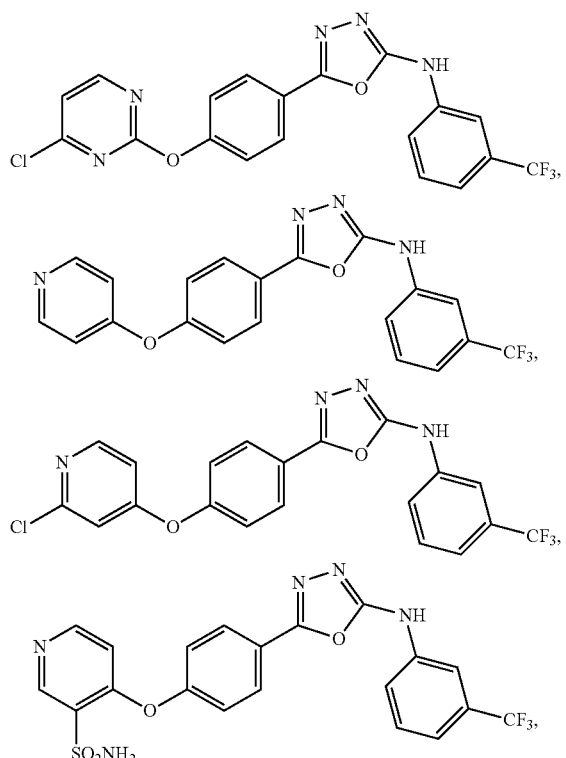
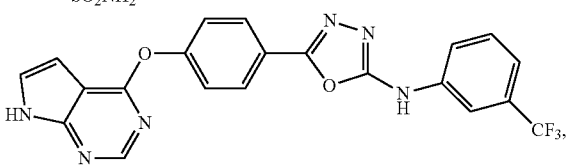
-continued
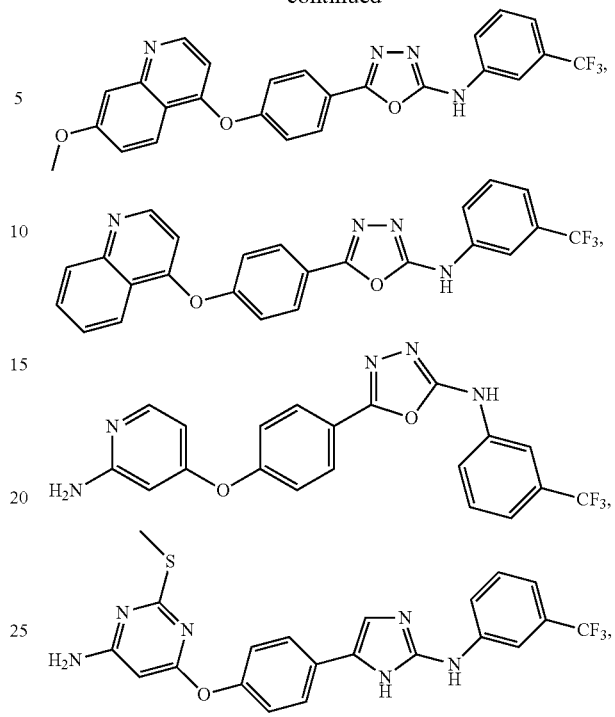
and the like.
In some embodiments, there are provided compounds having structure (I) selected from the group consisting of
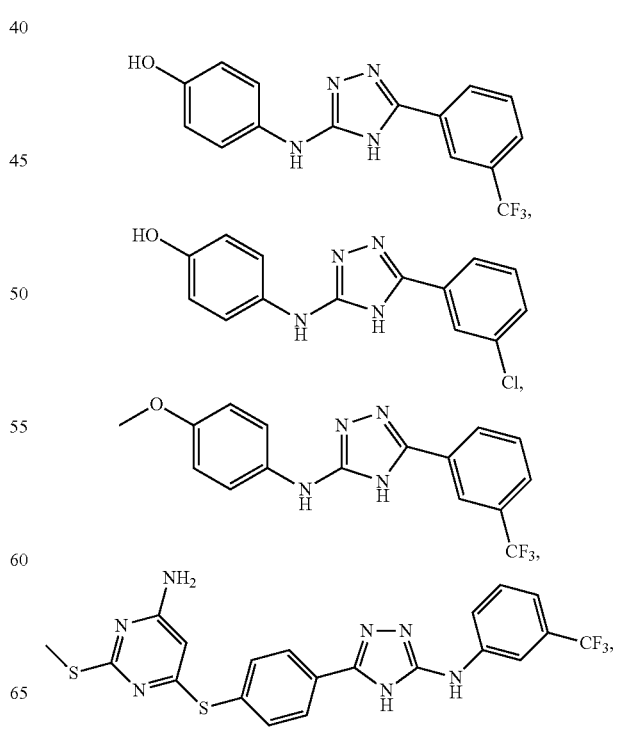

-continued

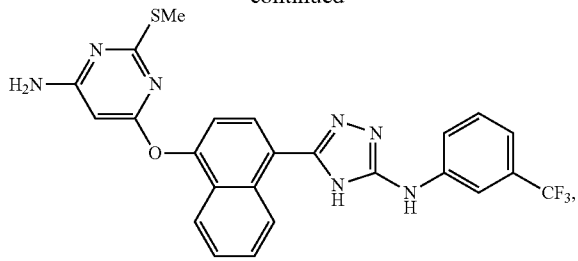

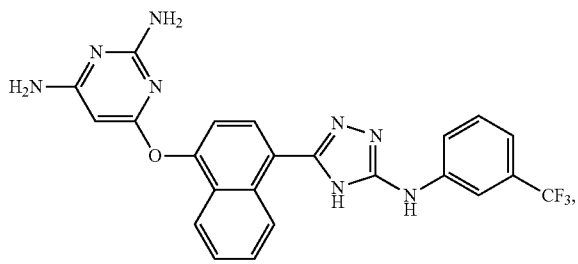

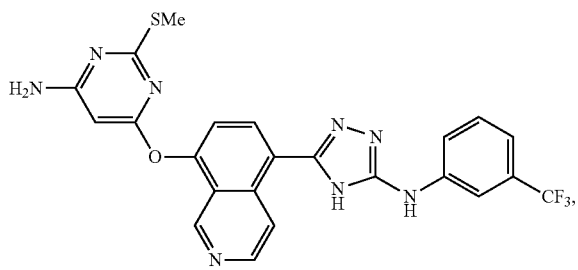

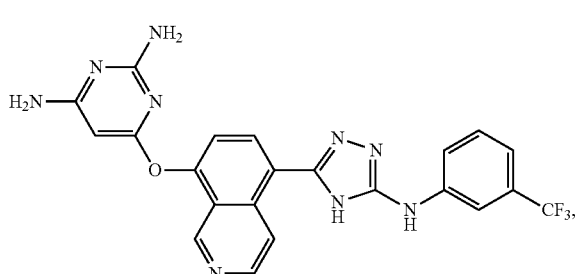

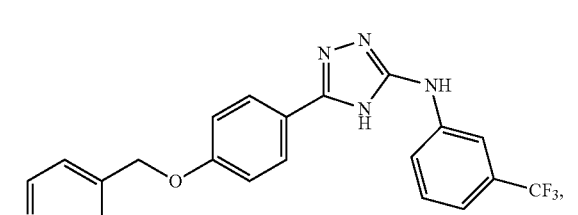

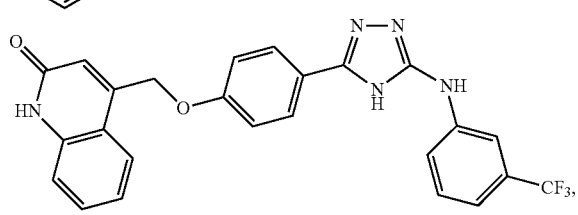

and the like.

In some embodiments, there is provided a compound having the structure (II) or an N-oxide, N,N'-dioxide, N,N',N''-trioxide, or a pharmaceutically acceptable salt thereof:

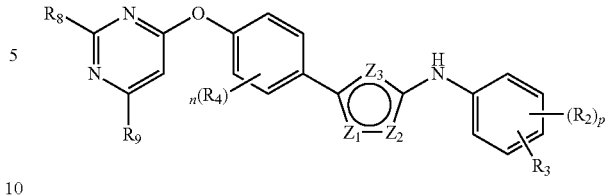

(II)

or an N-oxide, N,N'-dioxide, N,N',N''-trioxide, or a pharmaceutically acceptable salt thereof:
wherein
each of $Z_1$ and $Z_2$ is independently selected from a group consisting of CH, N, and $NR_5$, wherein $R_5$ is hydrogen or lower alkyl;
$Z_3$ is O, S, N, or $NR_5$, wherein $R_5$ is hydrogen or lower alkyl;
each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;
$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NH-$COR_6$, —$NR_6R_7$, —$SR_6$, —$S(O)R_6$, $S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; n is 1 or 2; and
$R_8$ and $R_9$ is independently selected from the group consisting of hydrogen, halogen, optionally substituted $C_1$-$C_6$ alkyl, —$CF_3$, —OH, optionally substituted $C_1$-$C_6$ alkoxy, —$NR_{10}R_{11}$, and —$SO_mR_{12}$, wherein $R_{10}$ and $R_{11}$ are independently selected from a group consisting of hydrogen, optionally substituted $C_1$-$C_6$ alkyl, —$SO_2R_{12}$, —$S(O)R_{12}$, and —$COR_{12}$, and $R_{12}$ is an optionally substituted alkyl or an optional substituted $C_3$-$C_{12}$ heteroaryl having 1-3 heteroatoms and m is 0-2.

In some embodiments, there are provided compounds having structure (II), wherein each $R_2$ and $R_3$ are independently selected from a group consisting of a hydrogen, a $C_1$-$C_6$ alkoxy, an optionally substituted $C_1$-$C_6$ alkyl, —$CF_3$, halogen, —CN, and —$CO_2R'$ wherein R' is hydrogen or $C_1$-$C_6$ alkyl; or, optionally, $R_2$ and $R_3$ are joined to form a five to seven membered carbocycle. In some embodiments, $R_4$ is hydrogen. In some embodiments, $R_8$ and $R_9$ are independently selected from the group consisting of optionally substituted $C_1$-$C_6$ alkoxy, —$NR_{10}R_{11}$, and —$SO_mR_{12}$, and m is 0-2. In certain embodiment, $R_8$ is $C_1$-$C_6$ alkoxy or —$SR_{12}$. In some embodiments, each $R_2$ and $R_3$ are independently selected from a group consisting of a $C_1$-$C_6$ alkyl, —$CF_3$, and halogen wherein p is 0 or 1 or 2; or, optionally, $R_2$ and $R_3$ are joined to form a five to seven membered carbocycle.

Another embodiment provides the compound of structure (II), wherein $R_2$ and $R_3$ are independently selected from a group consisting of a hydrogen, a $C_1$-$C_6$ alkoxy, an optionally substituted $C_1$-$C_6$ alkyl, —$CF_3$, halogen, —CN, and —$CO_2R'$ wherein R' is hydrogen or $C_1$-$C_6$ alkyl.

In certain embodiments, the compound having the structure (II) is selected from the group consisting of
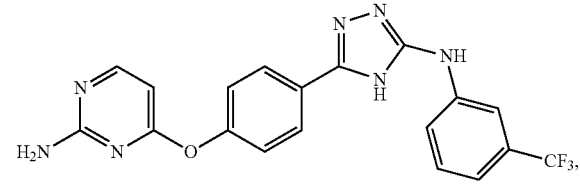
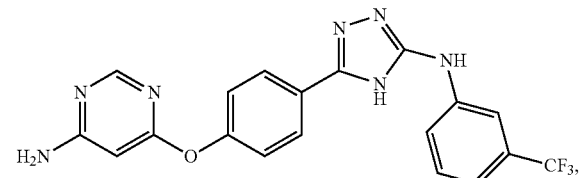
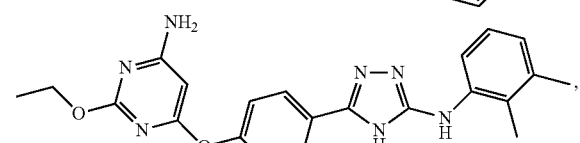
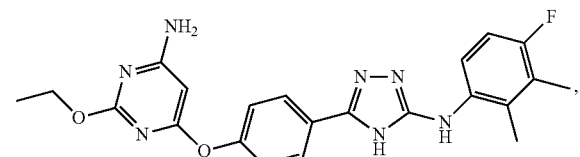
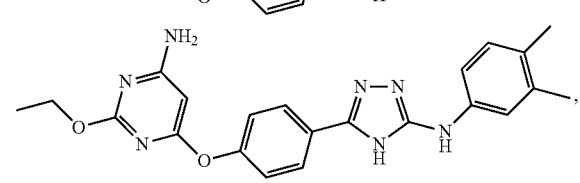
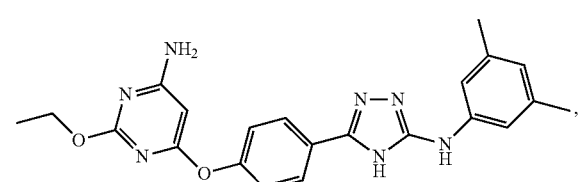
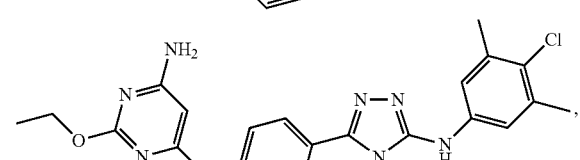
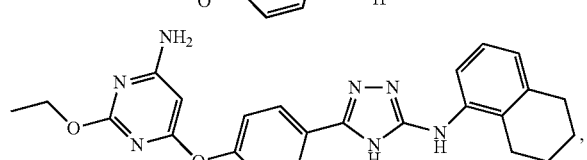
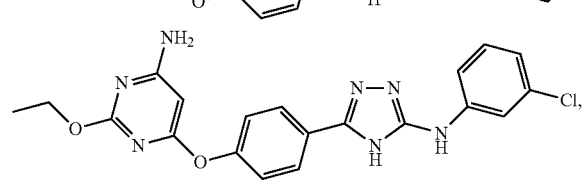
-continued
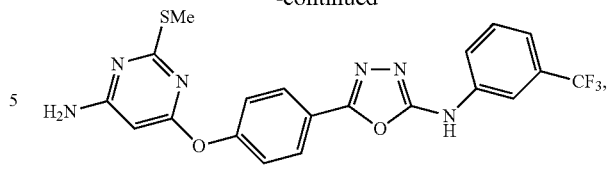
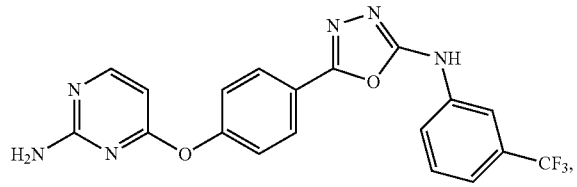
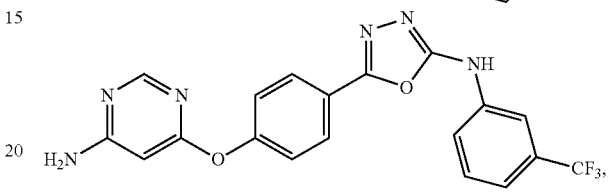
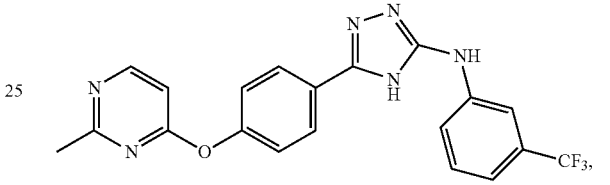
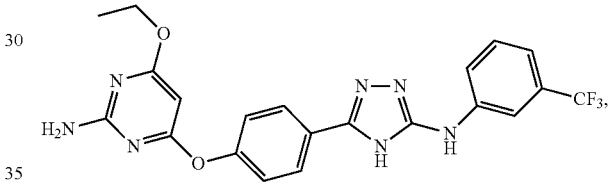
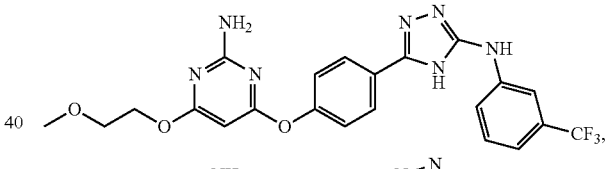
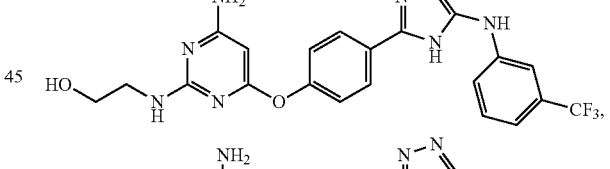
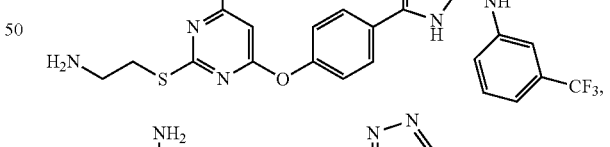
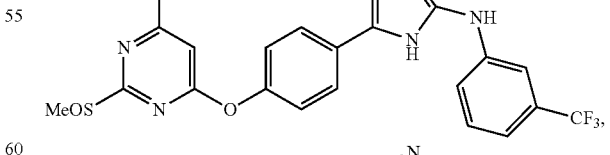
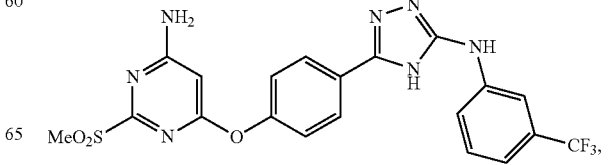

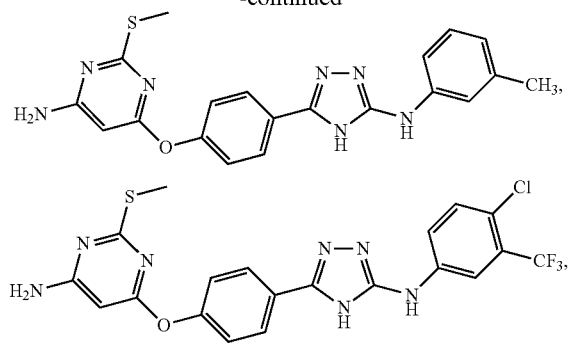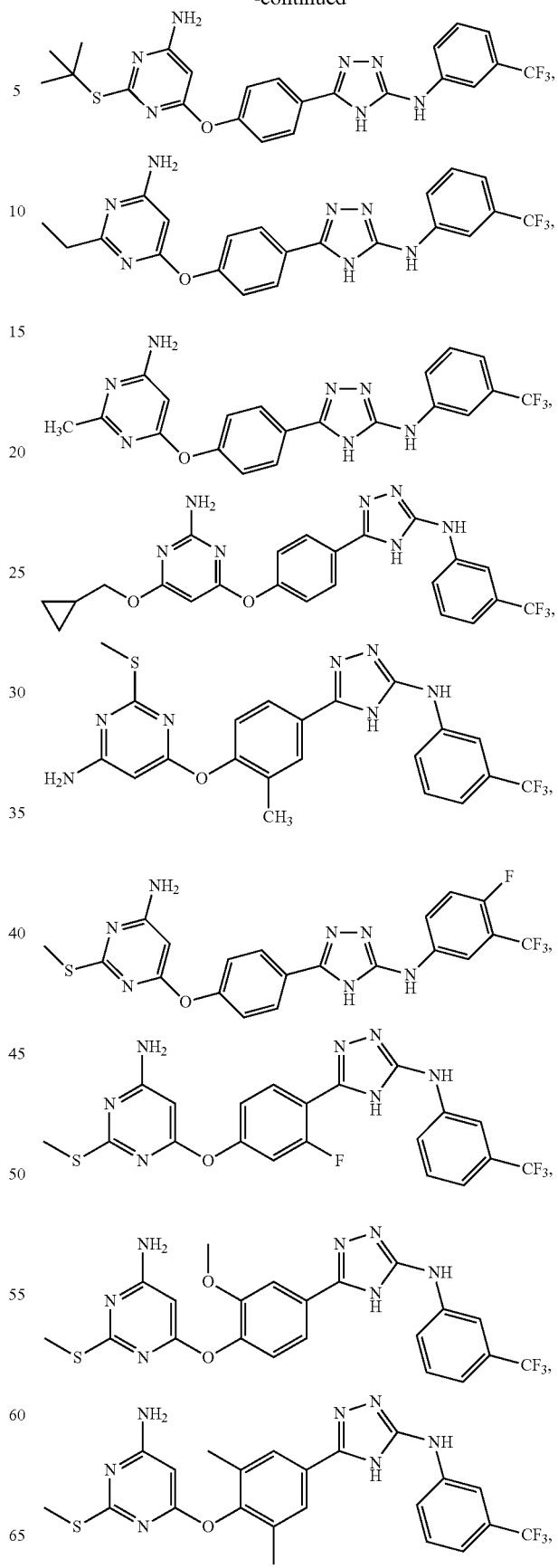

-continued
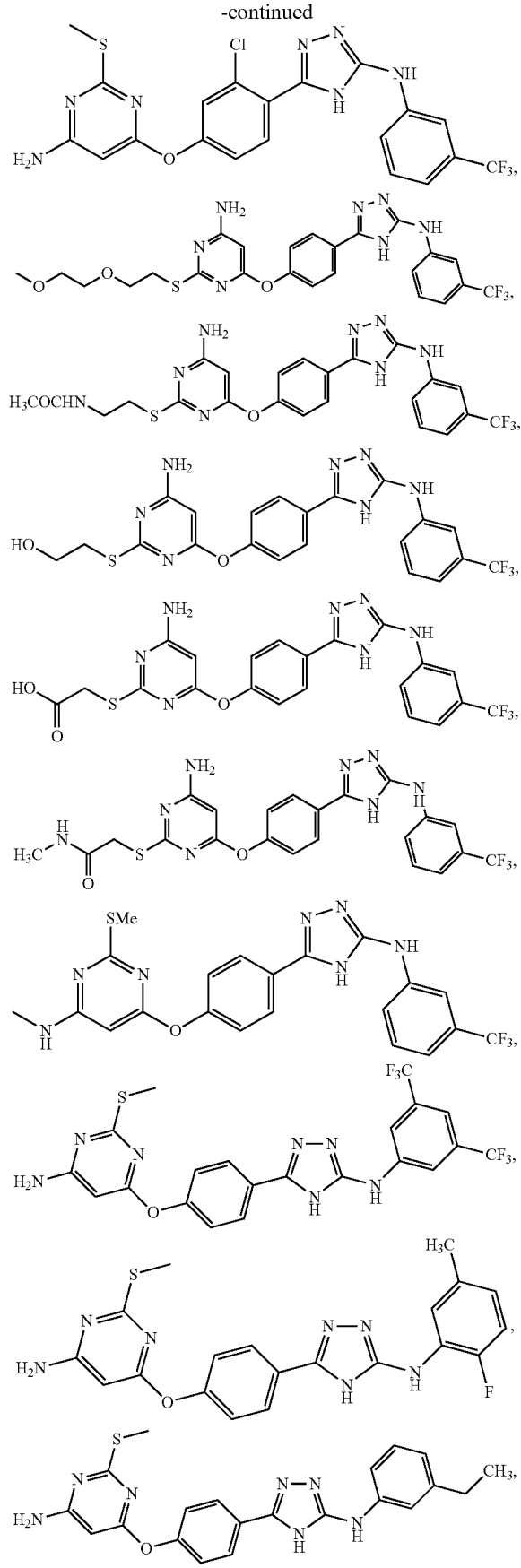
-continued
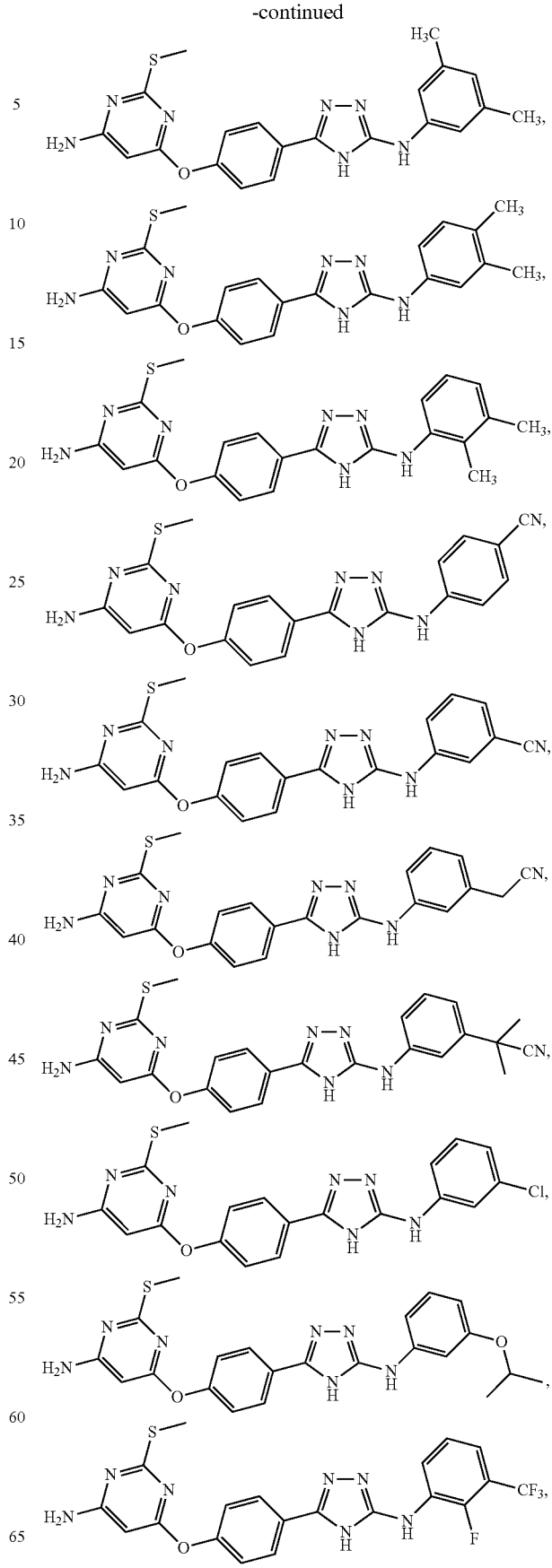

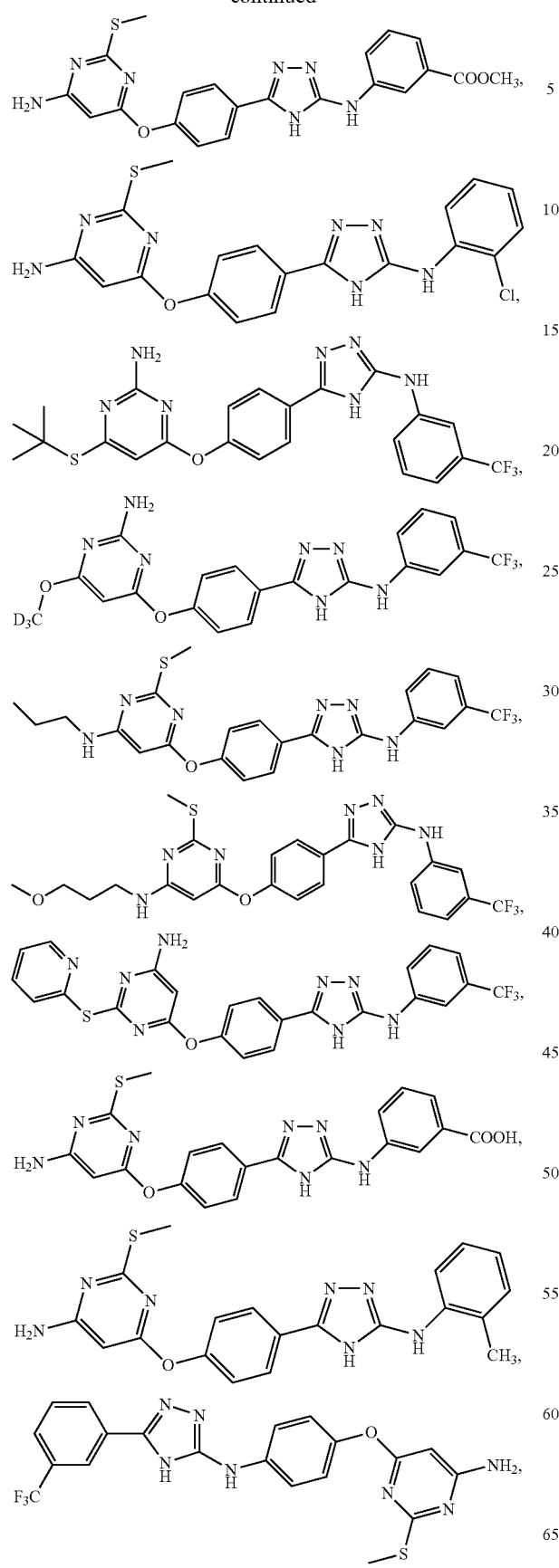
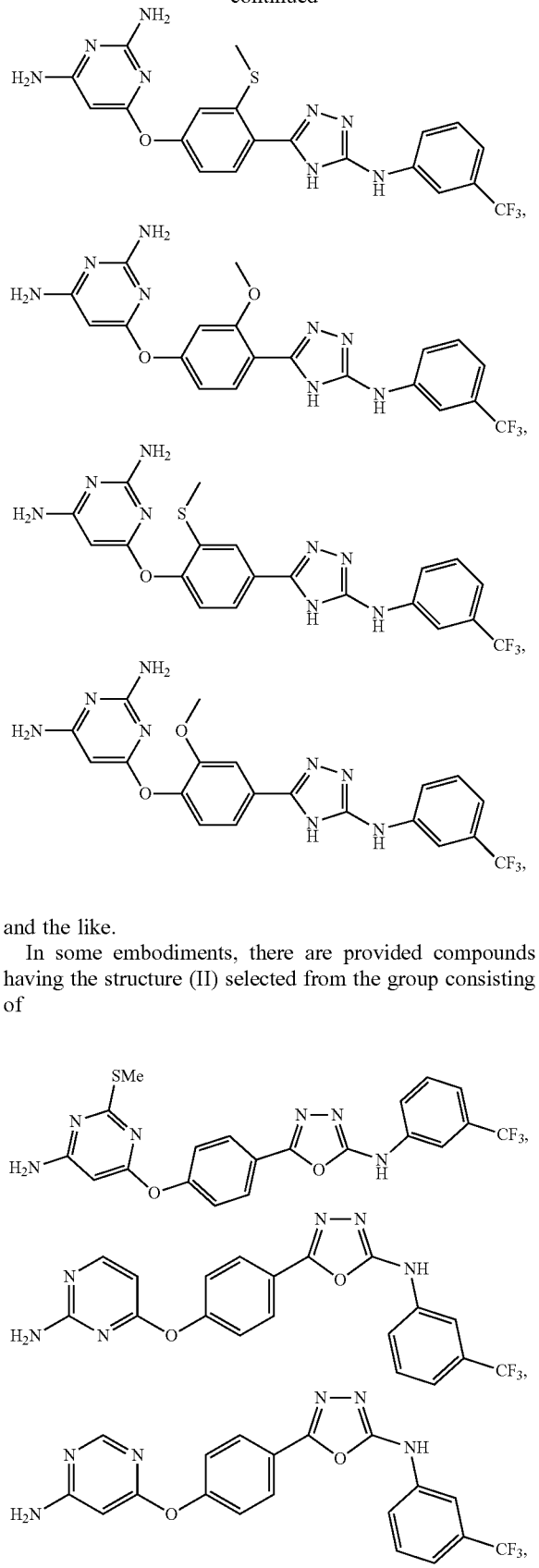
and the like.
In some embodiments, there are provided compounds having the structure (II) selected from the group consisting of
and the like.

In some embodiments, there are provided compounds having the structure (II) selected from the group consisting of

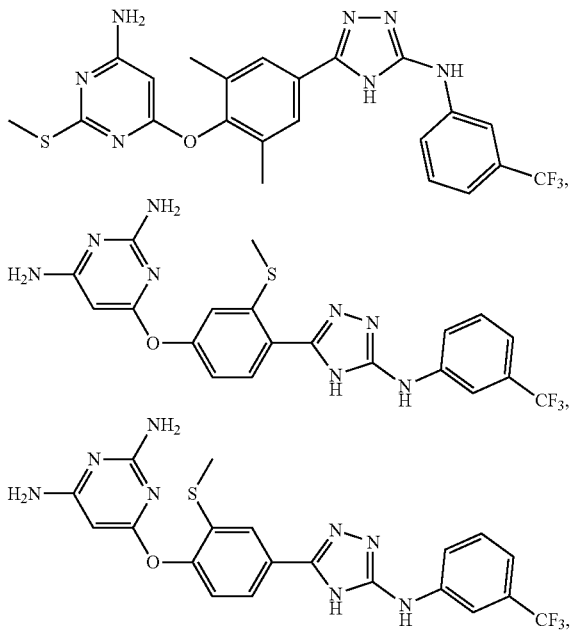

and the like.

In other embodiments, there is provided a compound having the structure (III) or an N-oxide, N,N'-dioxide, N,N',N''-trioxide, or a pharmaceutically acceptable salt thereof:

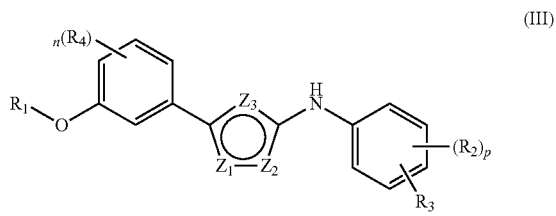

wherein
each of $Z_1$ and $Z_2$ is independently selected from a group consisting of CH, N, and $NR_5$, wherein $R_5$ is hydrogen or lower alkyl; and
$Z_3$ is O, S, N, or $NR_5$, wherein $R_5$ is hydrogen or lower alkyl.
$R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;
each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R' is hydrogen or $C_1$-$C_6$ alkyl; or, optionally, $R_2$ and $R_3$ are joined to form a five to seven membered carbocycle;

$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NHCOR_6, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; p=0-4; and n is 1 or 2.

In some embodiments, the compounds have the structure (III), where $Z_3$ is O or S. In some embodiments, each $R_2$ and $R_3$ are independently selected from a group consisting of a $C_1$-$C_6$ alkyl, —$CF_3$, and halogen wherein p is 0 or 1 or 2; or, optionally, $R_2$ and $R_3$ are joined to form a five to seven membered carbocycle. In some embodiments, $R_1$ is an unsubstituted or a substituted $C_3$-$C_{12}$ heteroaryl having 1-3 heteroatoms. For example, $R_1$ is an unsubstituted or a substituted pyridine. In certain embodiments, $R_1$ is an unsubstituted pyridine or a $C_1$-$C_6$ alkyl substituted pyridine. In other embodiments, $R_1$ is an unsubstituted or a substituted pyrimidine. In some embodiments provide the compound having the structure (III) where $R_4$ is hydrogen.

Another embodiment provides the compound having the structure of formula (III), wherein
$R_2$ and $R_3$ is independently selected from a group consisting of a hydrogen, a $C_1$-$C_6$ alkoxy, an optionally substituted $C_1$-$C_6$ alkyl, —$CF_3$, halogen, —CN, and —$CO_2R'$ wherein R' is hydrogen or $C_1$-$C_6$ alkyl; and
$R_4$ is independently selected from a group consisting of hydrogen, halogen, $C_1$-$C_6$ alkyl, —OH, —$NO_2$, —CN, $C_1$-$C_6$ alkoxy, —$NHCOR_6$, —$NH_2$, —$NR_6R_7$, —$SR_6$, —$S(O)R_6$, —$S(O)_2R_6$, —$CO_2R_6$, and —$CONR_6R_7$, wherein $R_6$ and $R_7$ are independently selected from a group consisting of hydrogen, and an optionally substituted $C_1$-$C_6$ alkyl and n is 1 or 2. In some embodiments, $R_2$ and $R_3$ are independently selected from a group consisting of a hydrogen, a $C_1$-$C_6$ alkoxy, an optionally substituted $C_1$-$C_6$ alkyl, —$CF_3$, halogen, —CN, and —$CO_2R'$ wherein R' is hydrogen or $C_1$-$C_6$ alkyl; and $R_4$ is independently selected from a group consisting of hydrogen, halogen, $C_1$-$C_6$ alkyl, —OH, —$NO_2$, —CN, $C_1$-$C_6$ alkoxy, —$NHCOR_6$, —$NH_2$, —$NR_6R_7$, —$SR_6$, —$S(O)R_6$, $S(O)_2R_6$, —$CO_2R_6$, and —$CONR_6R_7$, wherein $R_6$ and $R_7$ are independently selected from a group consisting of hydrogen and an optionally substituted $C_1$-$C_6$ alkyl.

In certain embodiments, the compound having structure (III) is selected from the group consisting of

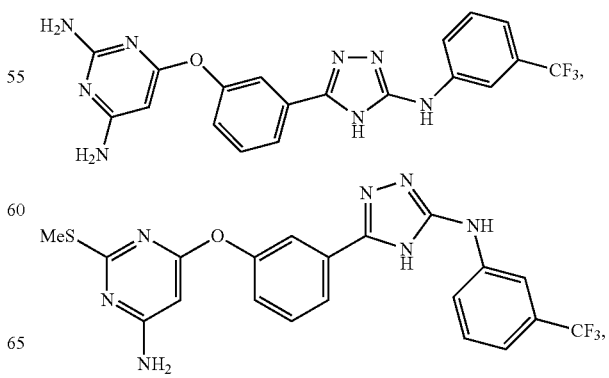

-continued
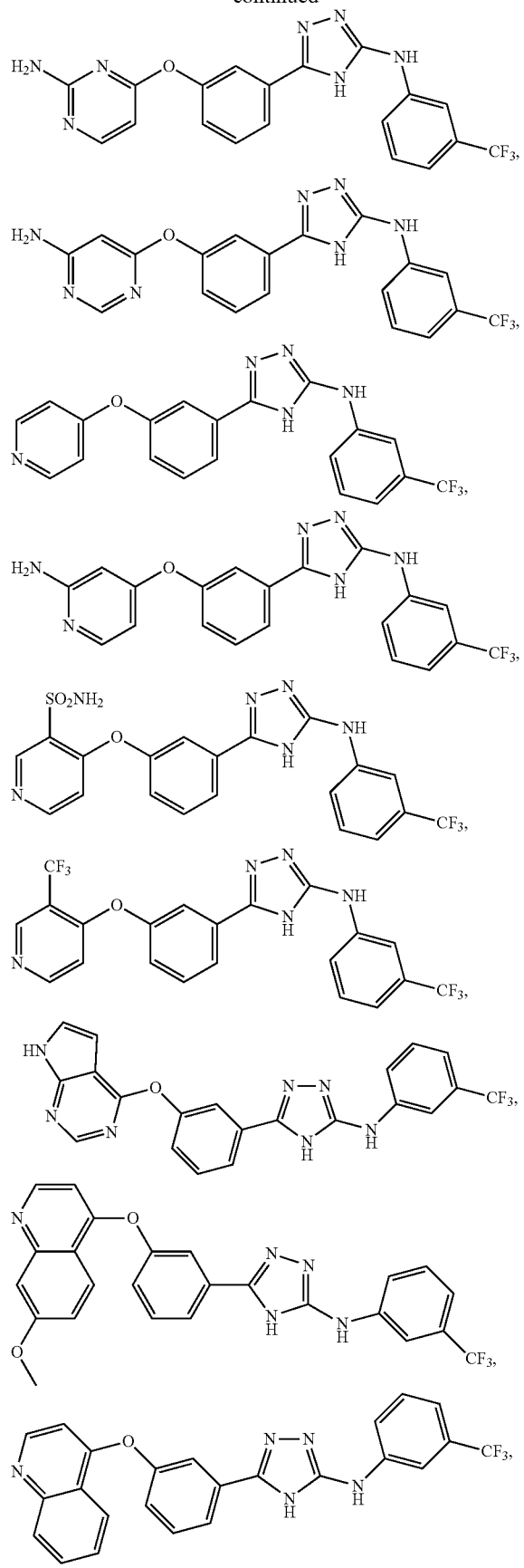
-continued
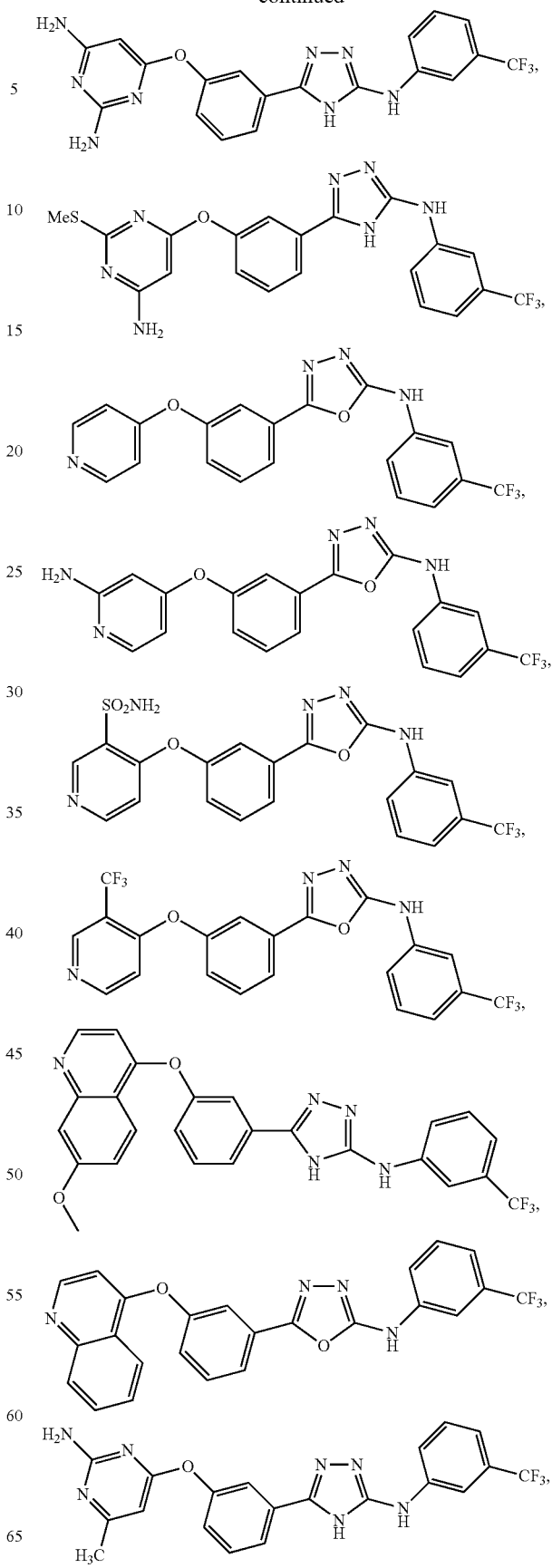

-continued
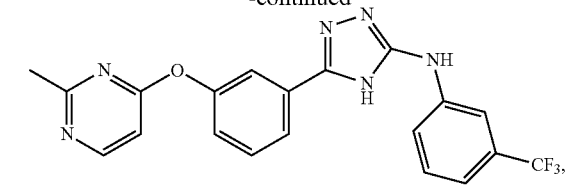
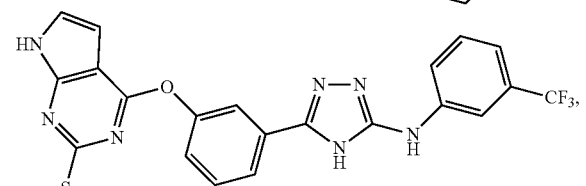
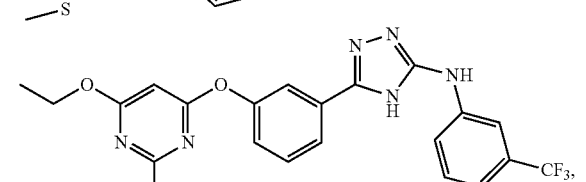
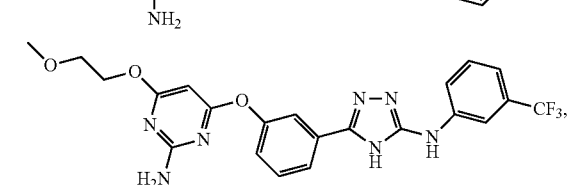
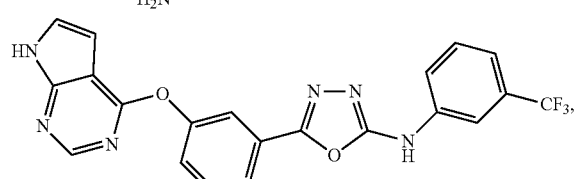
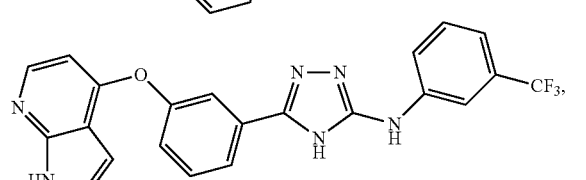
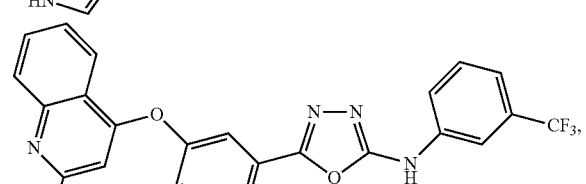
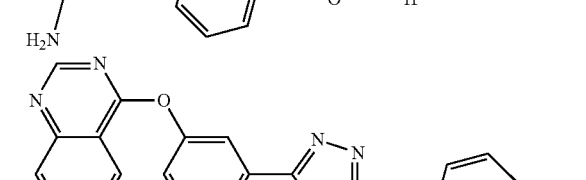
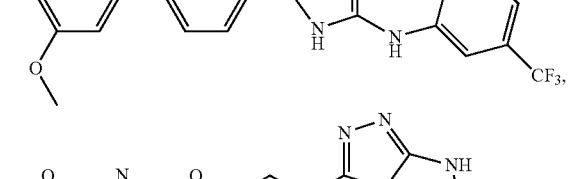
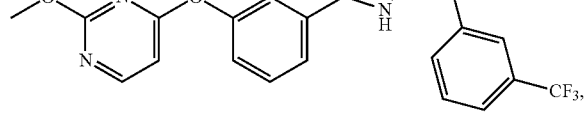
-continued
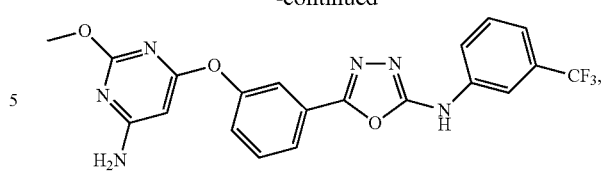
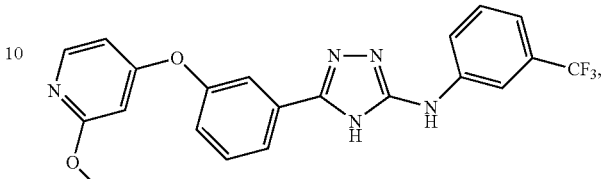
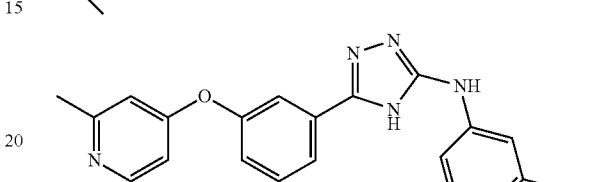
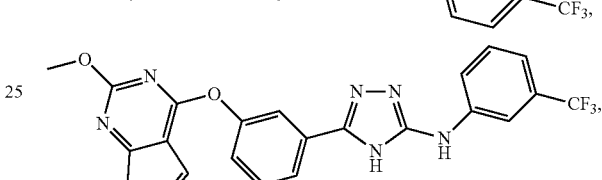
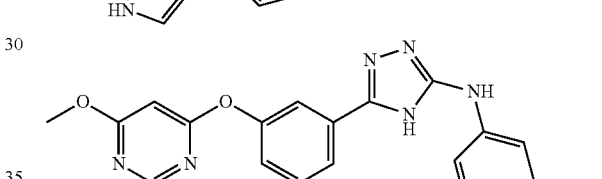
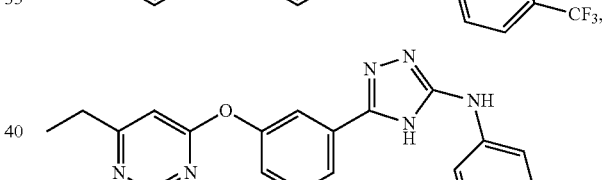
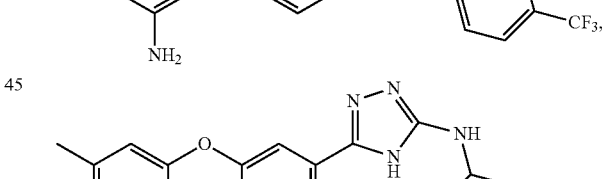
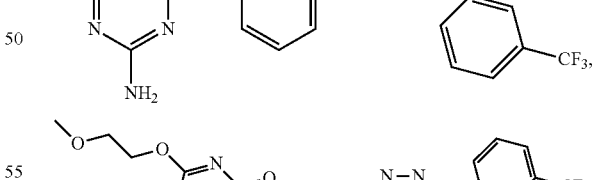
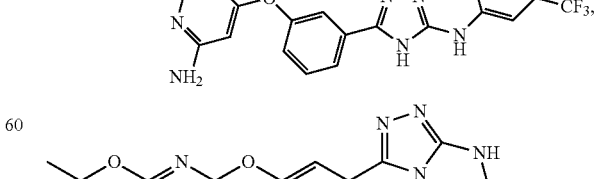
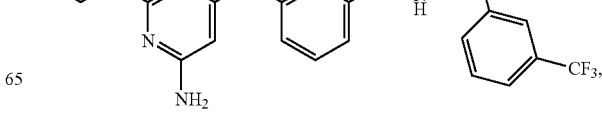

-continued
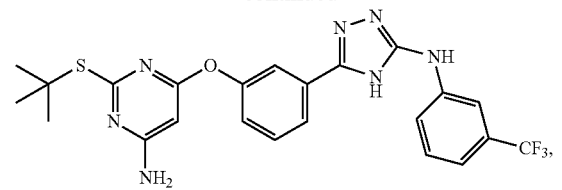
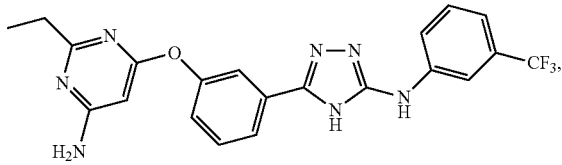
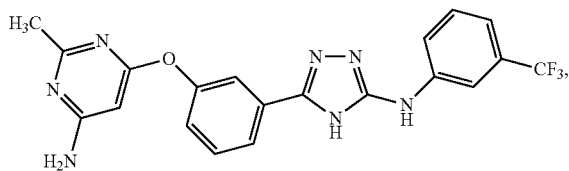
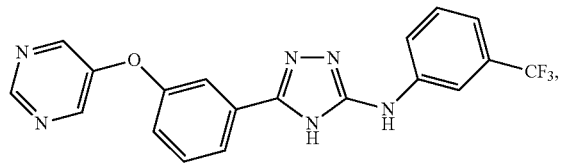
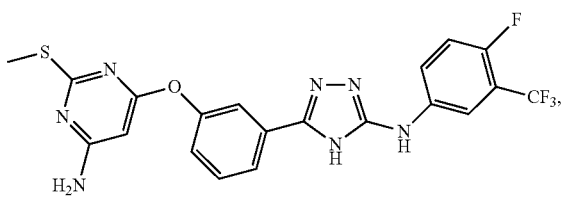
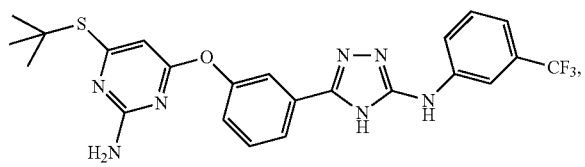
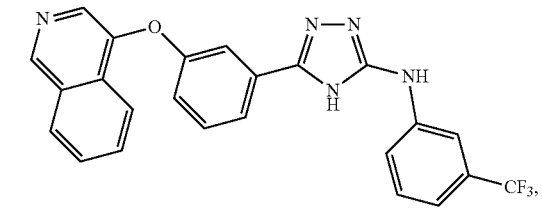
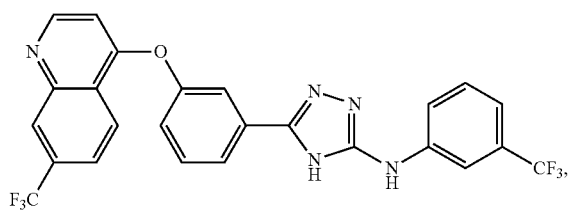
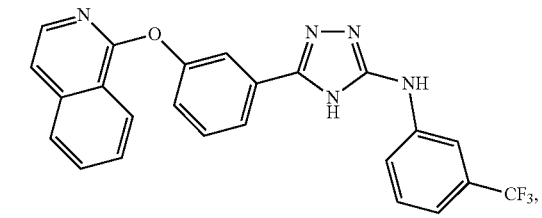
-continued
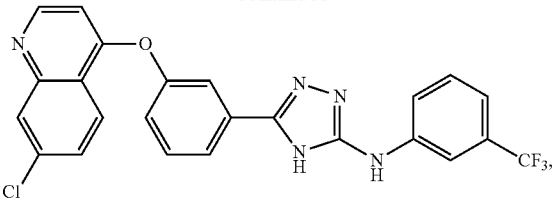
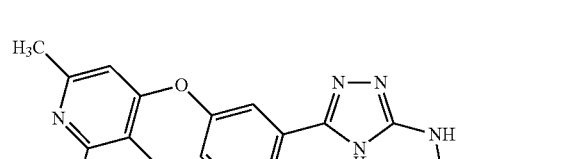
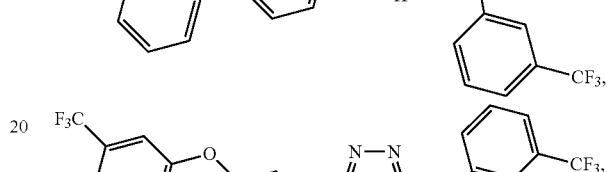
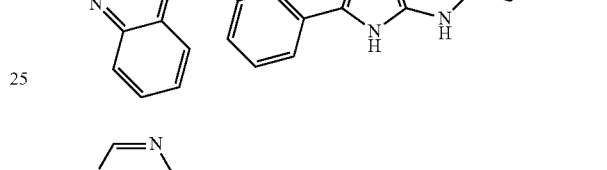
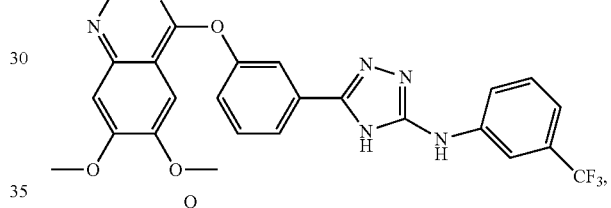
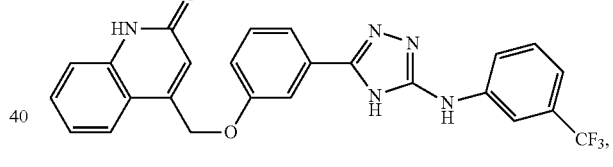
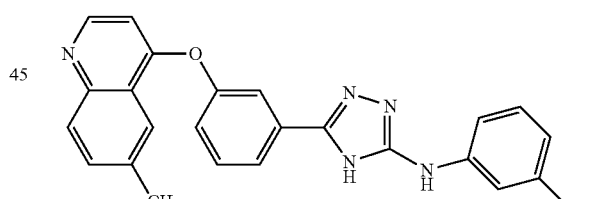
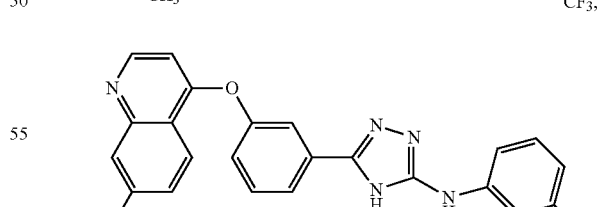
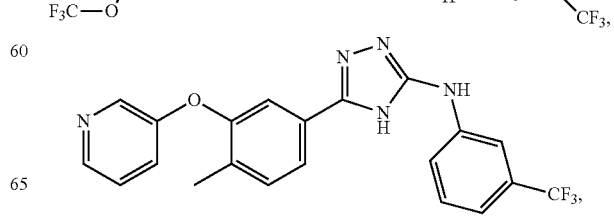

37
-continued
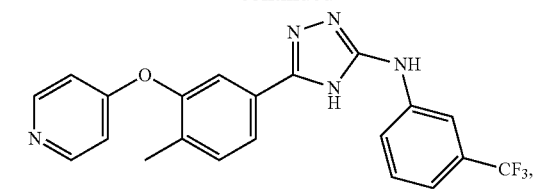
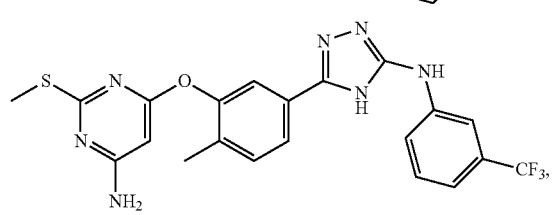
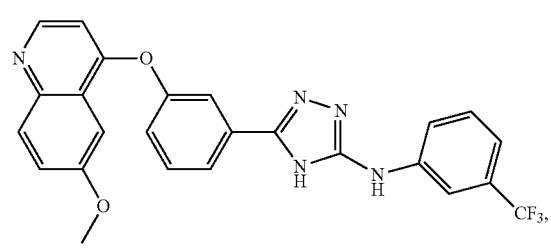
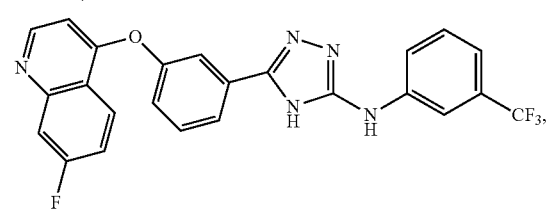
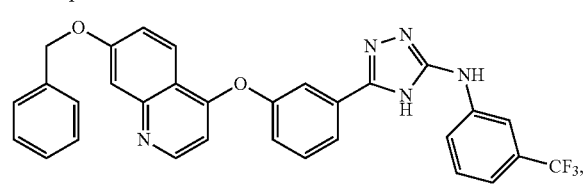
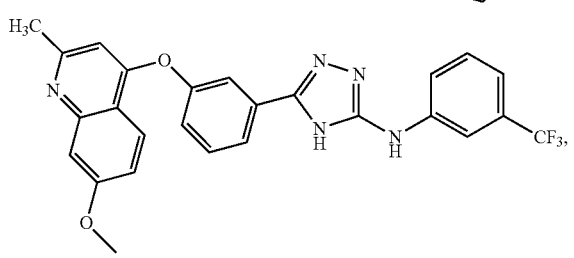
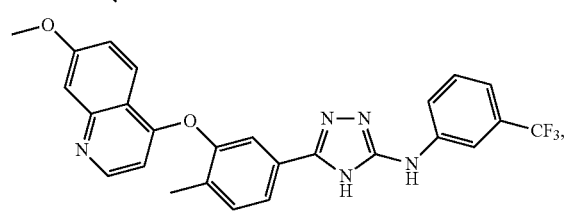
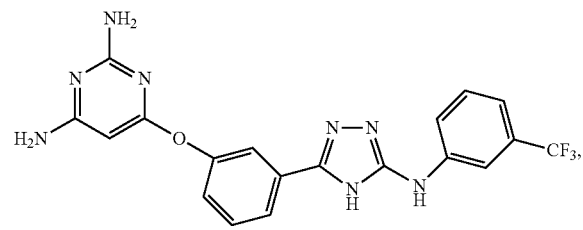
38
-continued
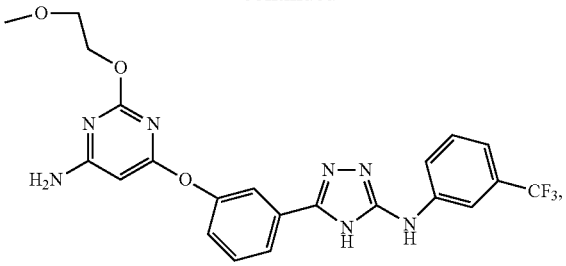
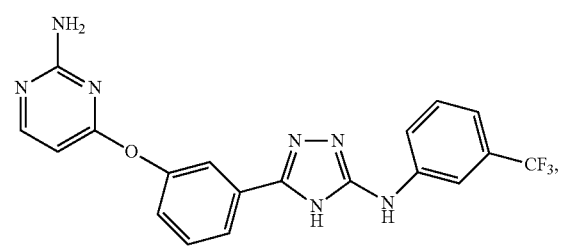
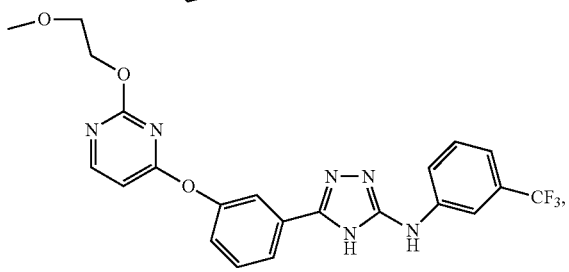
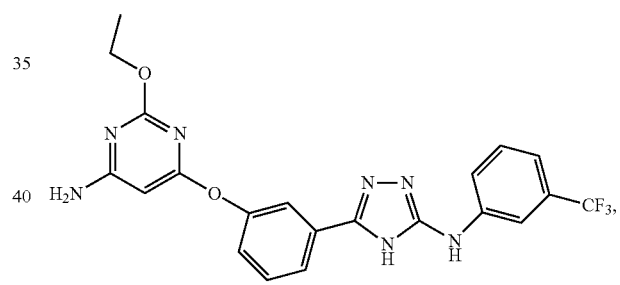
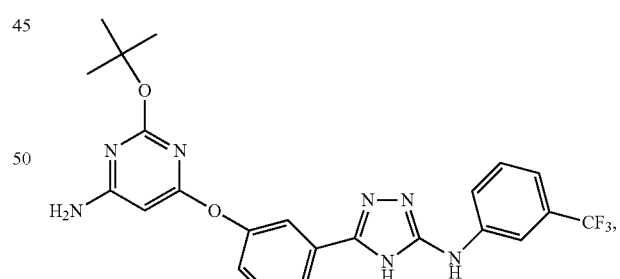
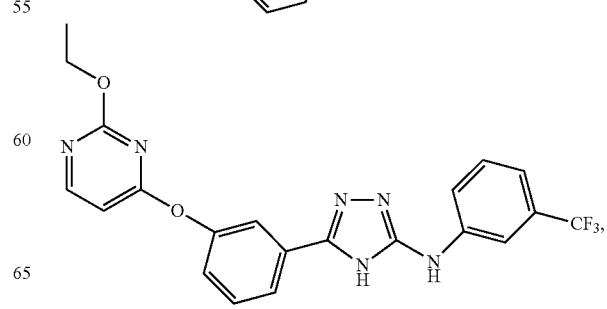

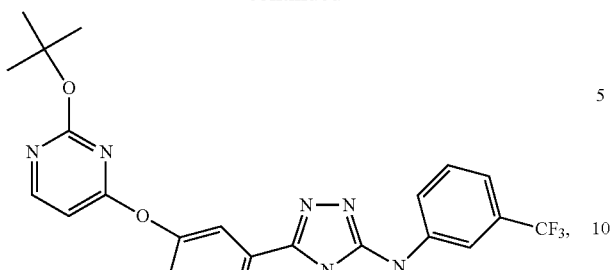
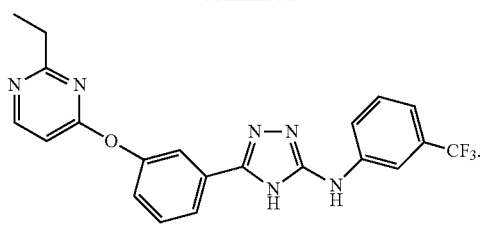
In some embodiments, the compound having the structure (III) is
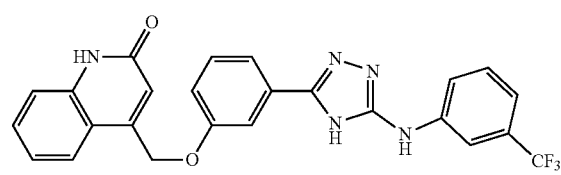
or selected from the group consisting of
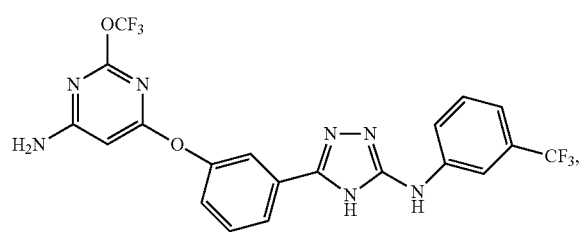
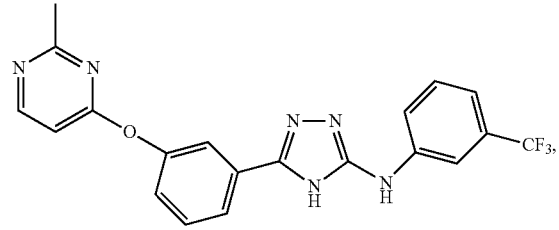
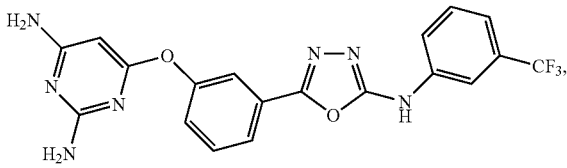
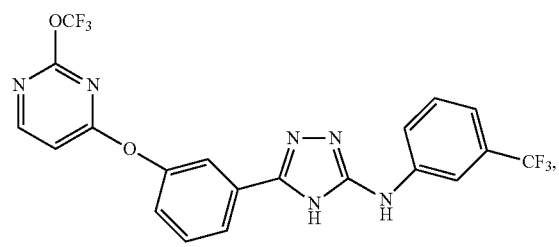
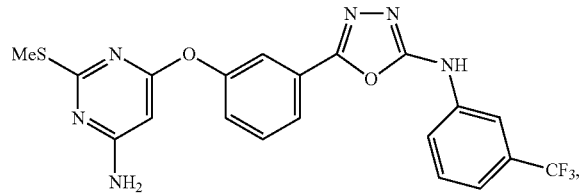
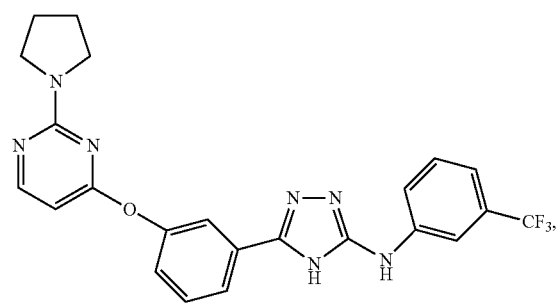
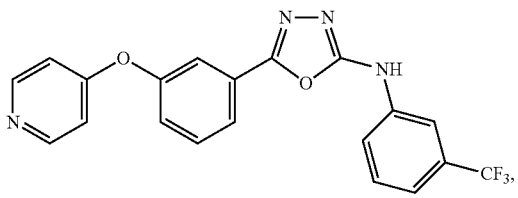
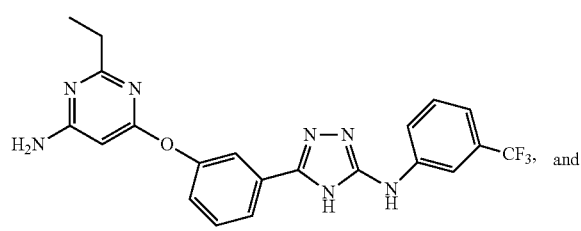
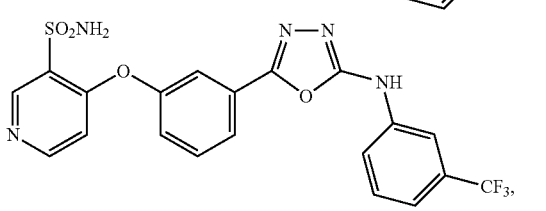

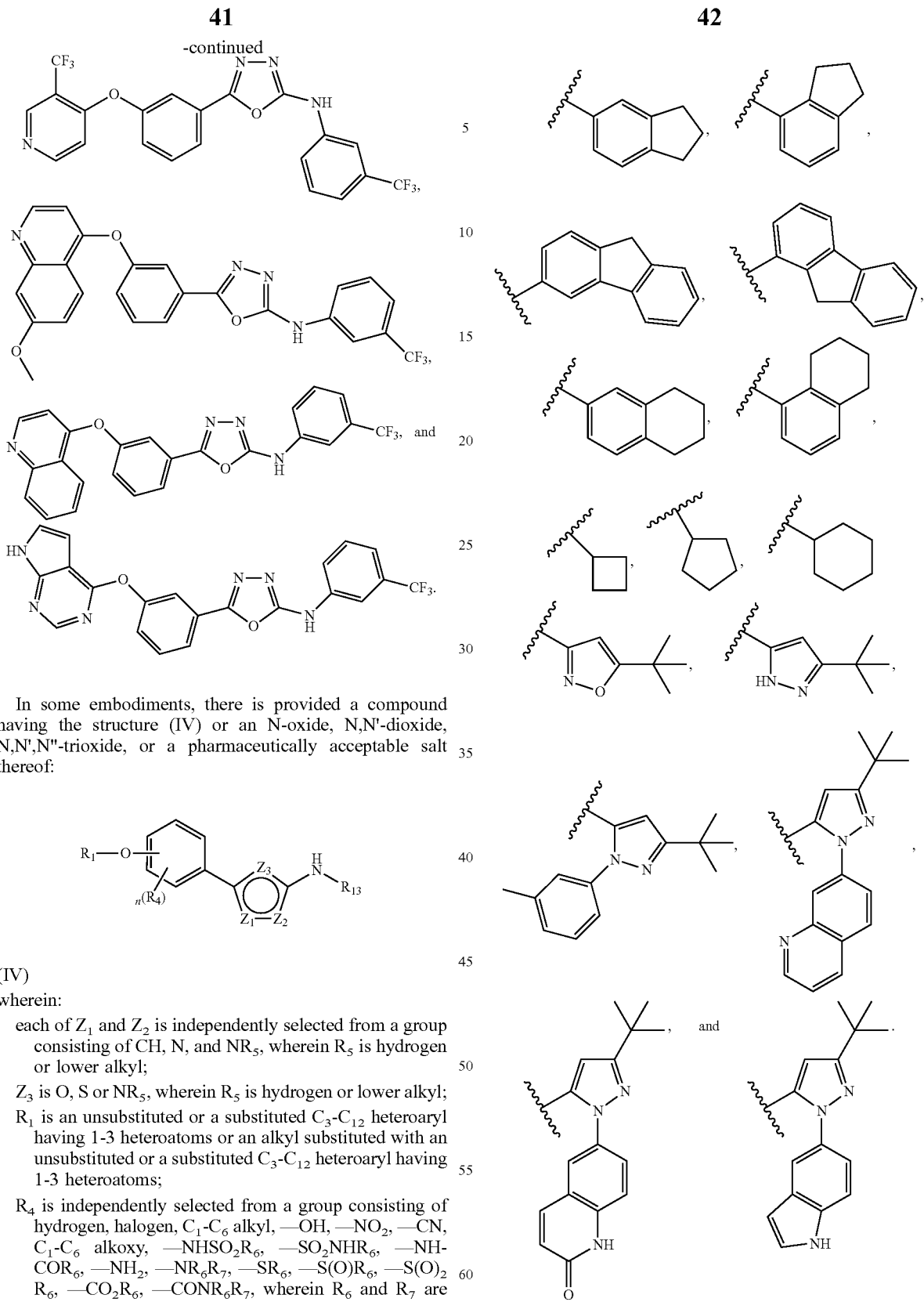

In some embodiments, there is provided a compound having the structure (IV) or an N-oxide, N,N'-dioxide, N,N',N"-trioxide, or a pharmaceutically acceptable salt thereof:

(IV)
wherein:
- each of $Z_1$ and $Z_2$ is independently selected from a group consisting of CH, N, and $NR_5$, wherein $R_5$ is hydrogen or lower alkyl;
- $Z_3$ is O, S or $NR_5$, wherein $R_5$ is hydrogen or lower alkyl;
- $R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;
- $R_4$ is independently selected from a group consisting of hydrogen, halogen, $C_1$-$C_6$ alkyl, —OH, —$NO_2$, —CN, $C_1$-$C_6$ alkoxy, —$NHSO_2R_6$, —$SO_2NHR_6$, —NH-$COR_6$, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl and n is 1 or 2; and
- $R_{13}$ is an optionally substituted —N—($C_1$-$C_6$ alkyl)pyrazolyl or is selected from a group consisting of the following structures:

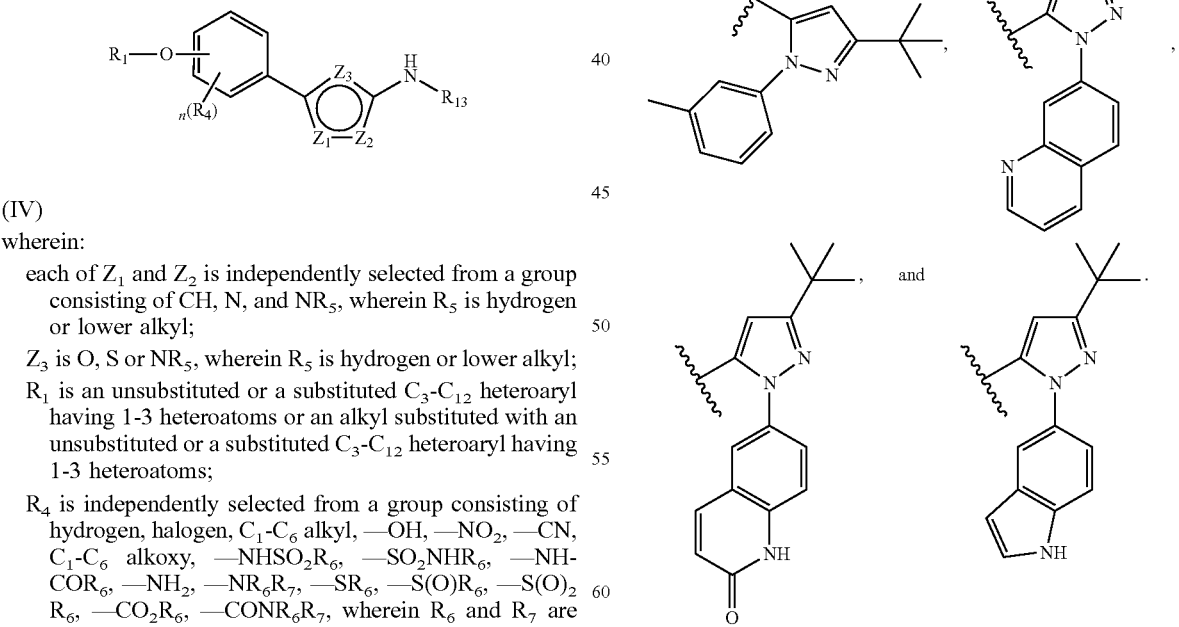

In some embodiments, the compound have structure (IV), where n is 2. In some embodiments, $Z_3$ is O or S. In certain embodiments, the compound having structure (IV) is selected from the group consisting of

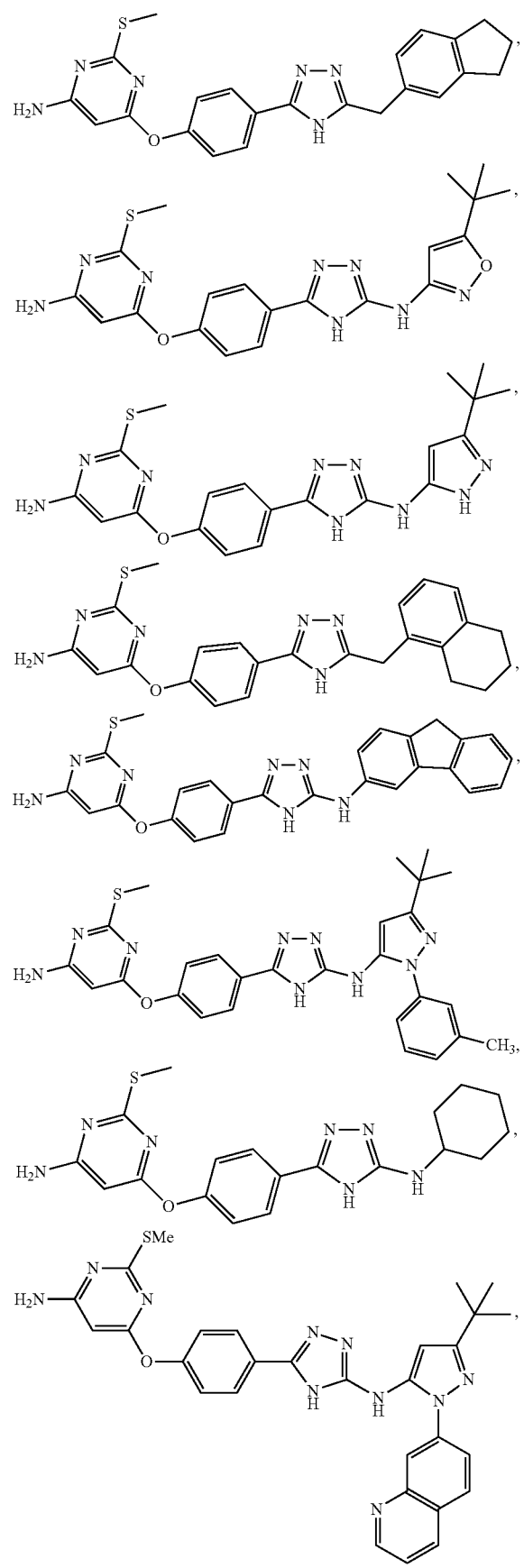

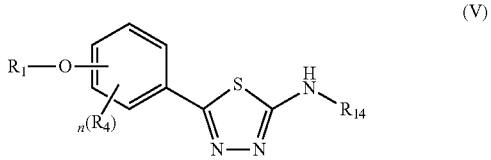

In other embodiments, there is provided a compound having the structure (V) or an N-oxide, N,N'-dioxide, N,N', N"-trioxide, or a pharmaceutically acceptable salt thereof:

(V)

wherein:

$R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;

$R_4$ is independently selected from a group consisting of hydrogen, halogen, $C_1$-$C_6$ alkyl, —OH, —NO$_2$, —CN, $C_1$-$C_6$ alkoxy, —NHSO$_2$R$_6$, —SO$_2$NHR$_6$, —NH-COR$_6$, —NH$_2$, —NR$_6$R$_7$, —SR$_6$, —S(O)R$_6$, —S(O)$_2$ R$_6$, —CO$_2$R$_6$, and —CONR$_6$R$_7$, wherein R$_6$ and R$_7$ are independently selected from a group consisting of hydrogen, and an optionally substituted $C_1$-$C_6$ alkyl; n is 1 or 2; and $R_{14}$ is selected from a group consisting of an optionally substituted $C_1$-$C_{12}$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, and an optional substituted $C_3$-$C_{12}$ heteroaryl having 1-3 heteroatoms.

In certain embodiments, the compound having structure (V) is selected from the group consisting of

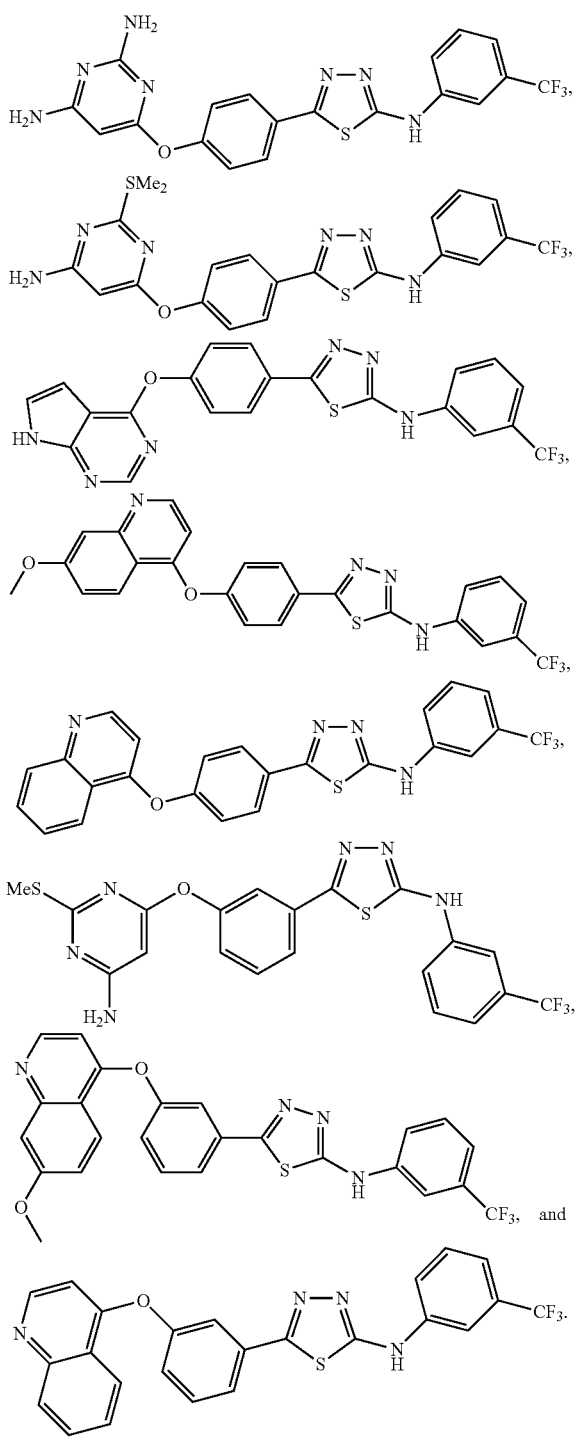

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) is two-fold more massive than hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the Deuterium Kinetic Isotope Effect (DKIE) and can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom, and occurs because transition states involving a proton can sometimes form in the absence of the required activation energy. A deuterium is larger and statistically has a much lower probability of undergoing this phenomenon. Substitution of tritium for hydrogen results in yet a stronger bond than deuterium and gives numerically larger isotope effects.

Deuterium (D or $^2H$) is a stable, non-radioactive isotope of hydrogen and has molecular weight of 2.0144. The natural abundance of deuterium is 0.015%. Thus in all chemical compounds with a H atom, the H atom actually represents a mixture of H and D, with about 0.015% being D. Deuterium-enriched compounds have different molecular weight and/or sizes from their hydrogen counter-parts. Deuteration of pharmaceuticals to improve pharmacokinetics (PK), pharmacodynamics (PD), and toxicity profiles, has been demonstrated previously with some classes of drugs. For example, DKIE was used to decrease the hepatotoxicity of halothane by presumably limiting the production of reactive species such as trifluoroacetyl chloride.

In some embodiments, the invention compounds having the structure (I) to (V) are deuterium-enriched by replacing at least one hydrogen atom with deuterium atom. In another embodiment, the deuterium enrichment is at least about 1%.

In certain embodiments, the invention compounds have the structures Ia-Va or an N-oxide, N,N'-dioxide, N,N',N''-trioxide, or a pharmaceutically acceptable salt thereof:

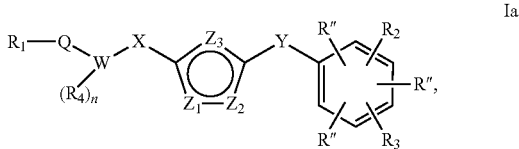

Ia

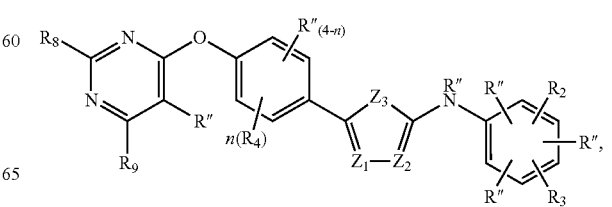

IIa

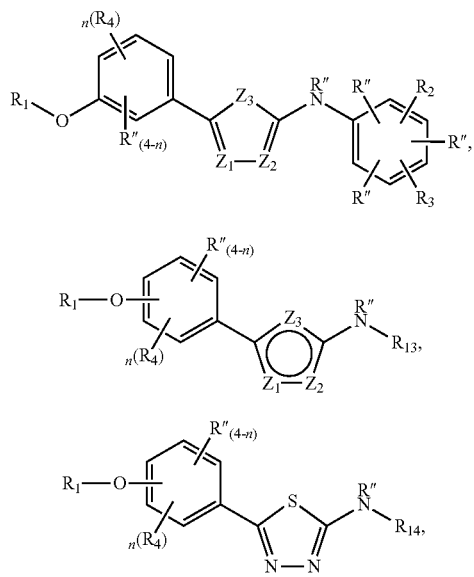

wherein
R″ is a H or D,
Q is O or S;
W is $C_6$-$C_{12}$ aryl or $C_3$-$C_{12}$ heteroaryl having 1-3 heteroatoms;
each of X and Y is independently absent or is NH;
each of $Z_1$ and $Z_2$ is independently selected from a group consisting of CH, N, and $NR_5$, wherein $R_5$ is hydrogen or lower alkyl;
$Z_3$ is O, S or $NR_5$, wherein $R_5$ is hydrogen or lower alkyl;
$R_1$ is an unsubstituted or a substituted $C_3$-$C_{12}$ heteroaryl having 1-3 heteroatoms or an alkyl substituted with an unsubstituted or a substituted $C_3$-$C_{12}$ heteroaryl having 1-3 heteroatoms;
each $R_2$ and $R_3$ are independently selected from a group consisting of a hydrogen, a $C_1$-$C_6$ alkoxy, an optionally substituted $C_1$-$C_6$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, an optional substituted $C_3$-$C_{12}$ heteroaryl having 1-3 heteroatoms, $CF_3$, halogen, CN, $CONHR_6$ and $CO_2R'$ wherein R′ is hydrogen or $C_1$-$C_6$ alkyl; or, optionally, $R_2$ and $R_3$ are joined to form a five to seven membered carbocycle;
$R_4$ is independently selected from a group consisting of hydrogen, halogen, $C_1$-$C_6$ alkyl, —OH, $NO_2$, —CN, $C_1$-$C_6$ alkoxy, —$NHSO_2R_6$, —$SO_2NHR_6$, —NHCOR_6, —$NH_2$, —$NR_6R_7$, —$SR_6$, —$S(O)R_6$, —$S(O)_2R_6$, —$CO_2R_6$, —$CONR_6R_7$, wherein $R_6$ and $R_7$ are independently selected from a group consisting of hydrogen, and an optionally substituted $C_1$-$C_6$ alkyl; and n is 1 or 2;
$R_8$ and $R_9$ are independently selected from the group consisting of hydrogen, halogen, optionally substituted $C_1$-$C_6$ alkyl, —$CF_3$, —OH, optionally substituted $C_1$-$C_6$ alkoxy, —$NR_{10}R_{11}$, and —$SO_mR_{12}$, wherein $R_{10}$ and $R_{11}$ are independently selected from a group consisting of hydrogen, optionally substituted $C_1$-$C_6$ alkyl, —$SO_2R_{12}$, —$S(O)R_{12}$, and —$COR_{12}$, and $R_{12}$ is an optionally substituted alkyl or an optional substituted $C_3$-$C_{12}$ heteroaryl having 1-3 heteroatoms and m is 0-2;
$R_{13}$ is an optionally substituted —N—($C_1$-$C_6$ alkyl)pyrazolyl or is selected from a group consisting of the following structures:

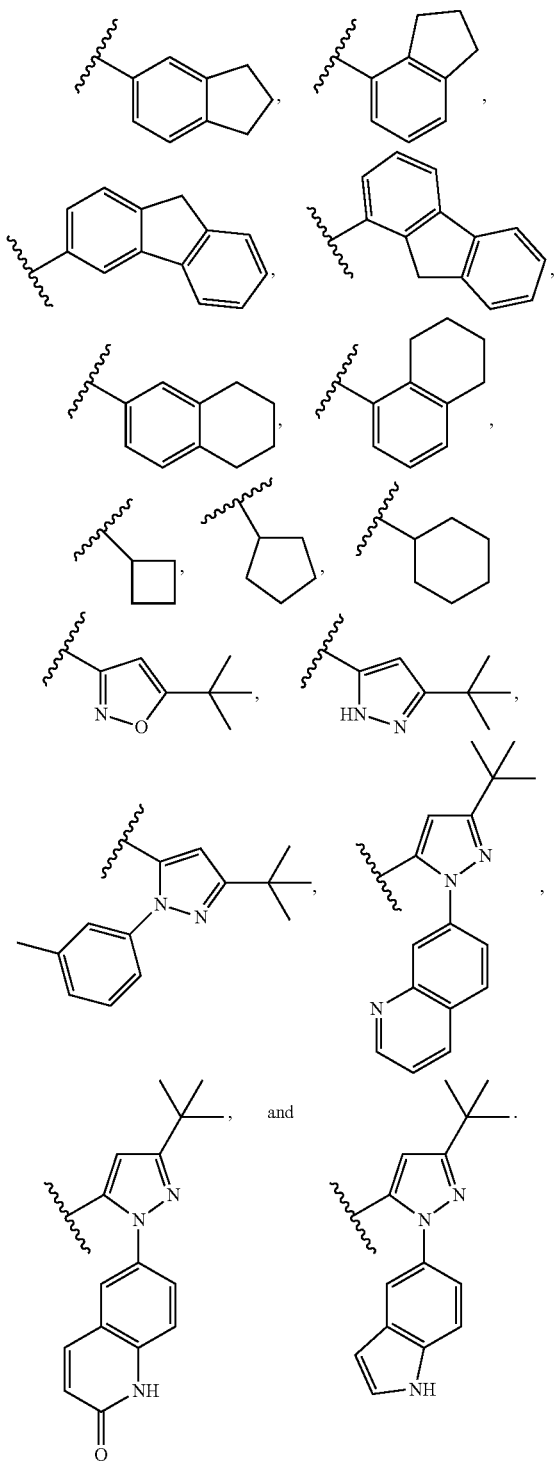

$R_{14}$ is selected from a group consisting of an optionally substituted $C_1$-$C_{12}$ alkyl, an optionally substituted $C_3$-$C_{12}$ cycloalkyl, an optionally substituted $C_3$-$C_{10}$ heterocycle having 1-3 heteroatoms, an optionally substituted $C_6$-$C_{12}$ aryl, and an optional substituted $C_3$-$C_{12}$ heteroaryl having 1-3 heteroatoms; and at least one hydrogen atom of the compound is replaced by deuterium atom.

In certain embodiments, the compound is selected from the group consisting of:

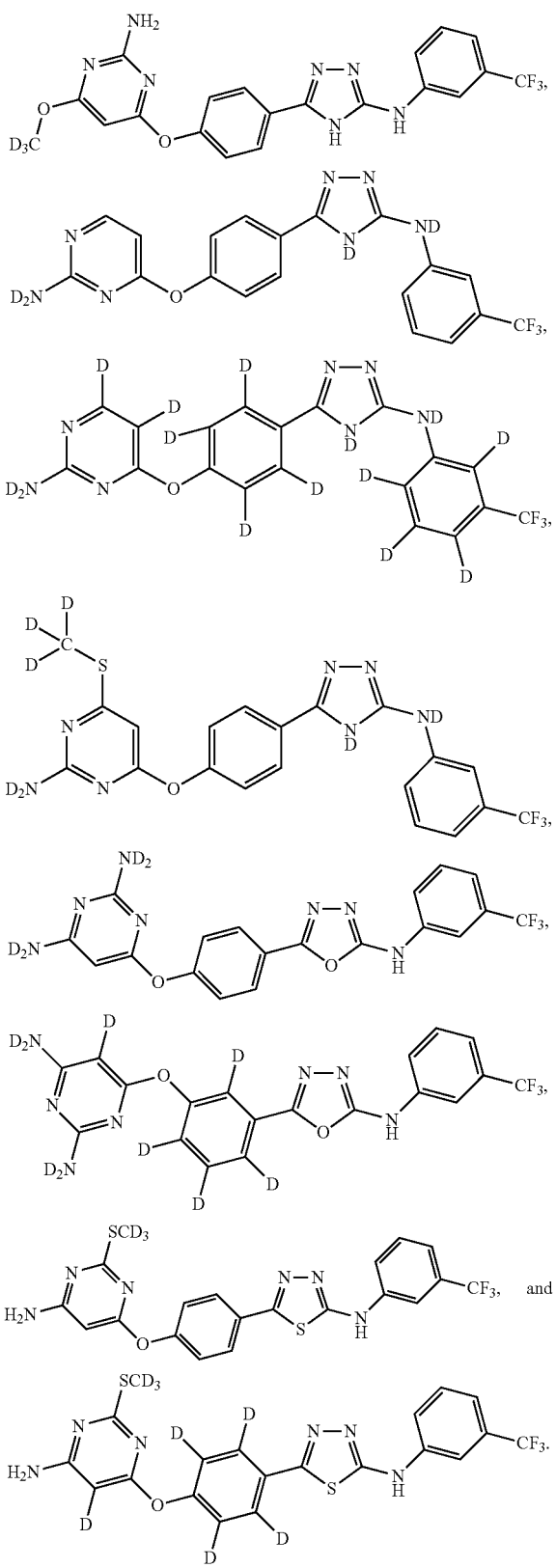

In some embodiments, there are provided pharmaceutical compositions comprising a compound having the structure (I)-(V) or (Ia)-(Va), in a pharmaceutically acceptable carrier.

In other embodiments, there are provided pharmaceutical compositions comprising a compound having the structure (I)-(V) or (Ia)-(Va), and a pharmaceutically acceptable excipient.

In some embodiments, there are provided methods for suppressing, preventing or inhibiting lymphangiogenesis, angiogenesis and/or growth of a tumor. The methods comprise contacting the tumor with a compound of structures I-V, Ia-Va or a pharmaceutical composition comprising the compound of structures I-V or Ia-Va thereof.

Due to the hydrophobic interactions and specific hydrogen bonding required for type II inhibition, the allosteric site adjacent to the kinase active site may be utilized to improve specificity over the type I Inhibitors that interact solely with the active kinase conformation in the highly conserved hinge region. In certain embodiments, the compound provided herein is a selective type II inhibitor of a PDGF receptor or RAF kinase. In certain embodiments, the compound provided herein is an allosteric inhibitor of PDGFRα, PDGFRβ, Flt3, RAF (e.g. A-RAF, B-RAF, C-RAF) and/or c-Kit.

Examples of Methods of Dosing and Treatment Regimens

In one aspect, the compositions containing the compounds of structures I-V or Ia-Va are administered for prophylactic and/or therapeutic treatments. In therapeutic applications, the compositions are administered to a human subject (patient) already suffering from a disease, disorder, or condition, in an amount sufficient to cure or at least partially arrest the symptoms of the disease, disorder, or condition. Amounts effective for this use will depend on the severity and course of the disease, disorder, or condition, previous therapy, the patient's health status, weight, and response to the drugs, and the judgment of the treating physician.

In prophylactic applications, compositions containing the compounds of structures I-V or Ia-Va are administered to a patient susceptible to or otherwise at risk of a particular disease, disorder or condition. Such an amount is defined to be a "prophylactically effective amount or dose." In this use, the precise amounts also depend on the patient's state of health, weight, and the like. In some embodiments, when used in a patient, effective amounts for this use depend on the severity and course of the disease, disorder or condition, previous therapy, the patient's health status and response to the drugs, and the judgment of the treating physician.

In some embodiments, the case wherein the patient's condition does not improve, upon the doctor's discretion the administration of the compounds of structures I-V or Ia-Va are administered chronically, that is, for an extended period of time, including throughout the duration of the patient's life in order to ameliorate or otherwise control or limit the symptoms of the patient's disease, disorder, or condition.

In some embodiments, wherein the patient's status does improve, upon the doctor's discretion the administration of the compounds of structures I-V or Ia-Va are given continuously; alternatively, the dose of drug being administered is temporarily reduced or temporarily suspended for a certain length of time (i.e., a "drug holiday"). In other embodiments, the length of the drug holiday varies between 2 days and 1 year, including by way of example only, about 2 days, about 3 days, about 4 days, about 5 days, about 6 days, about 7 days, about 10 days, about 12 days, about 15 days, about 20 days, about 28 days, about 35 days, about 50 days, about 70 days, about 100 days, about 120 days, about 150 days, about 180 days, about 200 days, about 250 days, about 280 days, about 300 days, about 320 days, about 350 days, or about 365 days. In further embodiments, the dose reduction during a drug holiday is from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's condition has occurred, a maintenance dose is administered if necessary. Subsequently, in other embodiments, the dosage or the frequency of administration, or both, are reduced, as a function of the symptoms, to a level at which the improved disease, disorder or condition is retained. In further embodiments, patients will, however, require intermittent treatment on a long-term basis upon any recurrence of symptoms.

In other embodiments, the amount of a given agent that corresponds to such an amount varies depending upon factors such as the particular compound, disease, disorder, or condition and its severity, the identity (e.g., weight) of the subject or host in need of treatment, but nevertheless is routinely determined in a manner according to the particular circumstances surrounding the case, including, e.g., the specific agent being administered, the route of administration, the condition being treated, and the subject or host being treated. In some embodiments, however, doses employed for adult human treatment are typically in the range of about 0.02 to about 5000 mg per day or about 1 to about 1500 mg per day. In further embodiments, the desired dose is conveniently presented in a single dose or as divided doses administered simultaneously (or over a short period of time) or at appropriate intervals, for example as two, three, four or more sub-doses per day.

In some embodiments, the pharmaceutical compositions described herein are in unit dosage forms suitable for single administration of precise dosages. In unit dosage form, the formulation is divided into unit doses containing appropriate quantities of one or more compound. In other embodiments, the unit dosage is in the form of a package containing discrete quantities of the formulation. Non-limiting examples are packaged tablets or capsules, and powders in vials or ampoules. In another embodiment, aqueous suspension compositions are packaged in single-dose non-reclosable containers. In further embodiments, multiple-dose reclosable containers are used, in which case it is typical to include a preservative in the composition. By way of example only, formulations for parenteral injection are presented in unit dosage form, which include, but are not limited to ampoules, or in multi-dose containers, with an added preservative.

The daily dosages appropriate for the compounds of structures I-V or Ia-Va described herein described herein are from about 0.01 to about 200 mg/kg per body weight. An indicated daily dosage in the larger mammal, including, but not limited to, humans, is in the range from about 0.5 mg to about 2000 mg, conveniently administered in divided doses, including, but not limited to, up to four times a day or in extended release form. Suitable unit dosage forms for oral administration include from about 1 to about 200 mg active ingredient. The foregoing ranges are merely suggestive, as the number of variables in regard to an individual treatment regime is large, and considerable excursions from these recommended values are not uncommon. In further embodiments, such dosages are altered depending on a number of variables, not limited to the activity of the compound used, the disease, disorder, or condition to be treated, the mode of administration, the requirements of the individual subject, the severity of the disease, disorder, or condition being treated, and the judgment of the practitioner.

In yet further embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and in some embodiments is expressed as the ratio between $LD_{50}$ and $ED_{50}$. In other embodiments, the data obtained from cell culture assays and animal studies is used in formulating a range of dosage for use in human. In some embodiments, the dosage of such compounds lies within a range of circulating concentrations that include the $ED_{50}$ with minimal toxicity. In yet further embodiments, the dosage varies within this range depending upon the dosage form employed and the route of administration utilized.

In some embodiments, there are also provided methods and compositions for treating cancer, restenosis, intimal hyperplasia, fibrotic diseases or angiogenesis-dependent disorder in a human subject. The methods comprise administering to a patient in need a compound of structures I-V or Ia-Va or a pharmaceutical composition comprising the compound of structures I-V or Ia-Va thereof. In certain embodiments, the compound is an allosteric inhibitor of PDGFRα, PDGFRβ, Flt3, RAF (e.g., A-RAF, B-RAF, C-RAF) and/or c-Kit. In another embodiment, the compound inhibits the heterodimerization of B-RAF with C-RAF or C-RAF with C-RAF. In certain embodiments, the compound is a selective type II inhibitor of a PDGF receptor or RAF kinase. In some embodiments, the invention compound modulates A-RAF. In some embodiments, the invention compound inhibits the phosphorylation of S338 of C-RAF.

Several structural and sequence homology studies of protein kinase domains have revealed a consensus of what are the common motifs that are required for catalytic activity. In some instances, these comprise residues that are required for nucleotide (ATP) binding, metal ion (Mg2+) binding and residues required for phosphoryl group transfer. There are 518 known human protein kinases, representing the third most common functional domain. Interestingly, about 10% of the kinome appear to lack at least one of the motifs required for catalysis and have been termed pseudokinases.

Several studies show that mutations affecting pseudokinase domains underlie the dysregulation of catalytic activity of several clinically-important kinases, including LKB 1, Raf and Jak2, by their partner pseudokinase regulators, STRAD, KSR and the Jak2 JH2 domain, respectively. These studies provide a link between pseudokiase-mediated dysregulation of signal transduction and a number of diseases including cancers and blood cell malignancies. Exemplary pseudokinases include STRADα, Integrin-linked kinase (ILK), HER3 (in human epidermal growth family), VRK3 (vaccinia related kinase 3), kinase suppressor of Ras (KSR), and the like.

In some embodiments, the methods described here for treating cancer in a human subject comprising administering to a patient in need of the invention compound that binds a pseudokinase. In certain embodiments, the pseudokinase is a kinase suppressor of Ras (KSR).

In some embodiments, there are provided a compound of structures I-V, Ia-Va that binds a pseudokinase. In certain embodiments, the pseudokinase is a kinase suppressor of Ras (KSR).

In certain embodiments, the cancer is resistant, refractory or non-responsive to a type I inhibitor of the protein kinase.

In certain embodiments, the cancer is resistant, refractory or non-responsive to a pan-RAF kinase drug or an ATP-competitive inhibitor. In certain embodiments, the cancer is resistant, refractory or non-responsive to a drug selected from Sorafenib, PLX4032, XL281, RAF265, 885-A, ZM336372, L-779450, AZ628, AAL881, LBT613, MCP110, 17-DMAG, CI1040, AZD6244/ARRY142886, PD0325901, SB590885, DP3346, and DP2514. In certain embodiments, the cancer is resistant, refractory or non-responsive to a VEGF-targeted therapy. In certain embodiments, the cancer is associated with a mutant form of RAF kinase; the mutant form of RAF kinase may be a B-RAF kinase selected from mutant T529I, T529N, G464A, G464E, G464V, G466A, G466E, G466V, G469A, G469E, N581S, E586K, F595L, G596R, L597V, L597R, T599I, V600E, and K601E; alternatively, the mutant form of RAF kinase is C-RAF gatekeeper mutant selected from T421N, and T421I. In certain embodiments, the cancer is selected from melanoma, breast cancer, colon cancer, pancreatic cancer, lung cancer, kidney cancer, and colon cancer. The cancer may be characterized by stroma rich tumors. In certain embodiments, the cancer has a mutant or aberration selected from N-RAS, H-RAS, K-RAS, B-RAF(V600E), B-RAF/Ras, HER1, p53, PTEN, and PI3K. In certain embodiments, the cancer exhibits up-regulation of the RAF-MEK-ERK pathway. In another embodiment, the compound of structures I-V or Ia-Va is administered orally to the patient in need. In another embodiment, the human subject is also provided with a therapy selected from anti-angiogenic therapy, a molucularyly-targeted therapy (such as those directed to other kinases (e.g. EGFR, HER2, HER4, MEK, VEGFR, c-MET, PI3K, AKT, etc.)) chemotherapy or radiation therapy. In another embodiment, the response of the human subject to the compound is monitored by inhibition of the phosphorylation of S338 of C-RAF.

In some embodiments, cancers that are treated by the methods provided herein include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, non-small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma, stromal), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastom, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia)! ovaries (ovarian carcinoma [serous cystadenocarcinoma, mucinous cystadenocarcinoma, endometrioid tumors, celioblastoma, clear cell carcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles, dysplastic nevi, lipoma, angioma, dermatofibroma, keloids, psoriasis; and Adrenal glands: neuroblastoma.

In some embodiments, acute myelocytic leukemia (AML) and/or acute lymphocytic leukemia (ALL) are treated using compounds of structures I-V or Ia-Va in monotherapy or combination therapy.

Restenosis literally means the reoccurrence of stenosis, a narrowing of a blood vessel, leading to restricted blood flow. Restenosis usually refers to an artery or other large blood vessel that has become narrowed, received treatment to clear the blockage and subsequently become renarrowed. This is usually restenosis of an artery, or other blood vessel, or possibly a vessel within an organ. Restenosis commonly results from balloon angioplasty and/or stent placement resulting in eventual occlusion of arteries by a process described as neointimal hyperplasia (NIH). After arterial injury, an over-proliferation of vascular smooth muscle cells occurs which has previously been shown to be dependent on both PDGFRα/β (Englesbe, et al. (2004) *J Vasc Surg* 39, 440-6) and MAPK pathway activation (Li, et al. (2005) *Circulation* 111, 1672-8; Pintucci, et al. (2006) *Faseb J* 20, 398-400). Therefore, the combination of PDGFRβ/RAF (e.g. B-RAF) inhibition would be an ideal treatment for NIH. Provided herein compounds of structures I-V or Ia-Va may be selected PDGFRβ/RAF (e.g. B-RAF) inhibitors. In certain embodiments, the restenosis in accordance with the invention methods is intimal hyperplasia-driven restenosis after vascular injury.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and Other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease. In certain embodiments, the fibrosis in accordance with the invention methods is pulmonary fibrosis or liver fibrosis.

In one embodiment, compounds of structures I-V or Ia-Va are administered to a human subject with fibrosis of an organ or tissue or with a predisposition of developing fibrosis of an organ or tissue with one or more other agents that are used to treat fibrosis. In one aspect, the one or more agents include corticosteroids. In another aspect, the one or more agents include immunosuppresants. In one aspect, the one or more agents include B-cell antagonists. In another aspect, the one or more agents include uteroglobin.

In certain embodiments, there are provided methods for preventing inhibition of ASK1-mediated apoptosis in a cell, sensitizing a cell to an extrinsic stress or inhibiting MEK1/2- and/or ERK1/2-mediated cellular proliferation or migration. The methods comprise contacting the tumor with a compound of structures I-V or Ia-Va or a pharmaceutical composition comprising the compound of structures I-V or Ia-Va thereof.

RAF kinase is an important convergent point downstream of FGFR and VEGFR2 signaling in endothelial cells and plays a critical role in endothelial cell survival during angiogenesis. The stromal compartment is a major contributor to angiogenesis and tumor growth. This includes pericytes associated with the newly forming endothelium, which stabilize the vasculature and promote vascularization. PDGFRβ is a receptor tyrosine kinase (RTK) that is essential for promoting proper pericyte function, which stabilizes blood vessels and enables vessel maturation. PDGFRβ signaling potentiates pericyte recruitment to newly forming vessels and the secretion of pro-angiogenic molecules such as VEGFA, FGF2, and Ang1 in the local microenvironment. This promotes vessel stabilization and remodeling of the immature vascular network to a highly ordered network. Maintenance of the vascular compartment is dependent upon paracrine loops such as the secretion of PDGF-BB and FGF2, which lead to increased expression of FGFR1 on VSMCs and PDGFRα/β on ECs, respectively. Therefore, the homeostasis of the mural and vascular compartments is critical for efficient angiogenesis. Thus inhibiting these two compartments simultaneously would initiate a potent inhibition of angiogenesis.

In certain embodiments, the compound is an allosteric inhibitor of PDGFRα, PDGFRβ, Flt3, RAF (e.g., A-RAF, B-RAF, C-RAF) and/or c-Kit. In another embodiment, the compound inhibits the heterodimerization of B-RAF with C-RAF or C-RAF with C-RAF. In certain embodiments, the compound is a selective type II inhibitor of a PDGF receptor or RAF kinase (e.g. B-RAF kinase). In certain embodiments, the extrinsic stress is selected from hypoxia, chemotherapy, radiotherapy or glucose/nutrient starvation. In certain embodiments, the compound of structures I-V or Ia-Va in accordance with the invention methods blocks VEGF- and/or FGF-stimulated endothelial responses in tumor angiogenesis.

In some embodiments, there are provided methods of inhibiting a protein kinase comprising contacting the protein kinase with an inhibitory concentration of a compound of structures I-V or Ia-Va or a pharmaceutical composition comprising the compound of structures I-V or Ia-Va thereof.

Certain Pharmaceutical and Medical Terminology

The term "acceptable" with respect to a formulation, composition or ingredient, as used herein, means having no persistent detrimental effect on the general health of the subject being treated.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Allosteric inhibitors (also known as non-competitive antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymhatic tissue (lymphoma), ovary, pancreas or other endocrine organ (thyroid), prostate, skin (melanoma) or hematological malignancies (such as the leukemias).

The term "carrier," as used herein, refers to relatively nontoxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different route of administration or at the same or different time.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of structures I-V or Ia-Va and a co-agent, are both administered to a patient simultaneously in the form of a single entity or dosage. The term "non-fixed combination" means that the active ingredients, e.g. a compound of structures I-V or Ia-Va and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound (i.e., a compound of structures I-V or Ia-Va described herein) with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Composition/Formulation

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins1999).

Provided herein are pharmaceutical compositions comprising a compound (i.e., a compound of structures I-V or Ia-Va described herein) and a pharmaceutically acceptable diluent(s), excipient(s), or carrier(s). In certain embodiments, the compounds described are administered as pharmaceutical compositions in which a compound (i.e., a compound of structures I-V or Ia-Va described herein) is mixed with other active ingredients, as in combination therapy. Encompassed herein are all combinations of actives set forth in the combination therapies section below and throughout this disclosure. In specific embodiments, the pharmaceutical compositions include one or more compounds (i.e., a compound of structures I-V or Ia-Va described herein).

A pharmaceutical composition, as used herein, refers to a mixture of a compound (i.e., a compound of structures I-V or Ia-Va described herein) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds (i.e., compounds of structures I-V or Ia-Va described herein) are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, a compound (i.e., a compound of structures I-V or Ia-Va described herein) is formulated in an aqueous solution. In specific embodiments, the aqueous solution is selected from, by way of example only, a physiologically compatible buffer, such as Hank's solution, Ringer's solution, or physiological saline buffer. In other embodiments, a compound (i.e., a compound of structures I-V or Ia-Va described herein) is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions. In specific embodiments, such solutions include physiologically compatible buffers and/or excipients.

In another embodiment, compounds described herein are formulated for oral administration. Compounds described herein, including a compound (i.e., a compound of structures I-V or Ia-Va described herein), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions of a compound (i.e., a compound of structures I-V or Ia-Va described herein) are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In one aspect, compounds (i.e., compounds of structures I-V or Ia-Va described herein) are prepared as solutions for parenteral injection as described herein or known in the art and administered with an automatic injector. Automatic injectors, such as those disclosed in U.S. Pat. Nos. 4,031,893, 5,358,489; 5,540,664; 5,665,071, 5,695,472 and WO/2005/087297 (each of which are incorporated herein by reference for such disclosure) are known. In general, all automatic injectors contain a volume of solution that includes a compound (i.e., a compound of structures I-V or Ia-Va described herein) to be injected. In general, automatic injectors include a reservoir for holding the solution, which is in fluid communication with a needle for delivering the drug, as well as a mechanism for automatically deploying the needle, inserting the needle into the patient and delivering the dose into the patient. Exemplary injectors provide about 0.3 mL of solution at about a concentration of 0.5 mg to 10 mg of a compound (i.e., a compound of structures I-V or Ia-Va described herein) per 1 mL of solution. Each injector is capable of delivering only one dose of the compound.

In still other embodiments, the compounds (i.e., a compound of structures I-V or Ia-Va described herein) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds (i.e., compounds of structures I-V or Ia-Va described herein) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of a compound (i.e., compounds of structures I-V or Ia-Va described herein) is accomplished by means of iontophoretic patches and the like. In certain embodiments, transdermal patches provide controlled delivery of a compound (i.e., a compound of structures I-V or Ia-Va described herein). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound (i.e., a compound of structures I-V or Ia-Va described herein); (2) a penetration enhancer; and (3) an aqueous adjuvant. In addition, transdermal formulations can include additional components such as, but not limited to, gelling agents, creams and ointment bases, and the like. In some embodiments, the transdermal formulation further include a woven or non-woven backing material to enhance absorption and prevent the removal of the transdermal formulation from the skin. In other embodiments, the transdermal formulations described herein maintain a saturated or supersaturated state to promote diffusion into the skin.

In other embodiments, the compounds of structures I-V or Ia-Va are formulated for administration by inhalation. Various forms suitable for administration by inhalation include, but are not limited to, aerosols, mists or powders. Pharmaceutical compositions of a compound (i.e., allosteric kinase inhibitors described herein) are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

Intranasal formulations are known in the art and are described in, for example, U.S. Pat. Nos. 4,476,116, 5,116,817 and 6,391,452, each of which is specifically incorporated by reference. Formulations, which include a compound (i.e. a compound of structures I-V or Ia-Va described herein), which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are found in sources such as REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein, may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

In still other embodiments, the compounds of structures I-V or Ia-Va are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound (i.e., allosteric kinase inhibitors described herein) may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound (i.e., a compound of structures I-V or Ia-Va described herein) described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least compound (i.e., a compound of structures I-V or Ia-Va described herein) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound (i.e., a compound of structures I-V or Ia-Va described herein). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity.

Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

Unless defined otherwise, all technical and scientific terms used herein have the standard meaning pertaining to the claimed subject matter belongs. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless otherwise indicated, conventional methods of mass spectroscopy, NMR, HPLC, protein chemistry, biochemistry, recombinant DNA techniques and pharmacology are employed. Unless specific definitions are provided, the standard nomenclature employed in connection with, and the standard laboratory procedures and techniques of, analytical chemistry, synthetic organic chemistry, and medicinal and pharmaceutical chemistry are employed. In certain instances, standard techniques are used for chemical syntheses, chemical analyses, pharmaceutical preparation, formulation, and delivery, and treatment of patients. In certain embodiments, standard techniques are used for recombinant DNA, oligonucleotide synthesis, and tissue culture and transformation (e.g., electroporation, lipofection). In some embodiments, reactions and purification techniques are performed e.g., using kits of manufacturer's specifications or as commonly accomplished or as described herein.

As used throughout this application and the appended claims, the following terms have the following meanings:

The term "alkenyl" as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Illustrative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-cecenyl.

The term "alkoxy" as used herein, means an alkyl group, as defined herein, appended to the parent molecular moiety through an oxygen atom. Illustrative examples of alkoxy include, but are not limited to, methoxy, ethoxy, propoxy, 2-propoxy, butoxy, tert-butoxy, pentyloxy, and hexyloxy.

The term "alkyl" as used herein, means a straight, branched chain, or cyclic (in this case, it would also be known as "cycloalkyl") hydrocarbon containing from 1-10 carbon atoms. Lower alkyl refers to an alkyl containing from 1-6 carbon atoms. Illustrative examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

The term "$C_1$-$C_6$-alkyl" as used herein, means a straight, branched chain, or cyclic (in this case, it would also be known as "cycloalkyl") hydrocarbon containing from 1-6 carbon atoms. Representative examples of alkyl include, but are not limited to, methyl, ethyl, n-propyl, iso-propyl, cyclopyl, n-butyl, sec-butyl, tert-butyl, cyclobutyl, n-pentyl, isopentyl, neopentyl, cyclopentyl, and n-hexyl.

The term "cycloalkyl" as used herein, means a monocyclic or polycyclic radical that contains only carbon and hydrogen, and includes those that are saturated, partially unsaturated, or fully unsaturated. Cycloalkyl groups include groups having from 3 to 10 ring atoms. Representative examples of cyclic include but are not limited to, the following moieties:

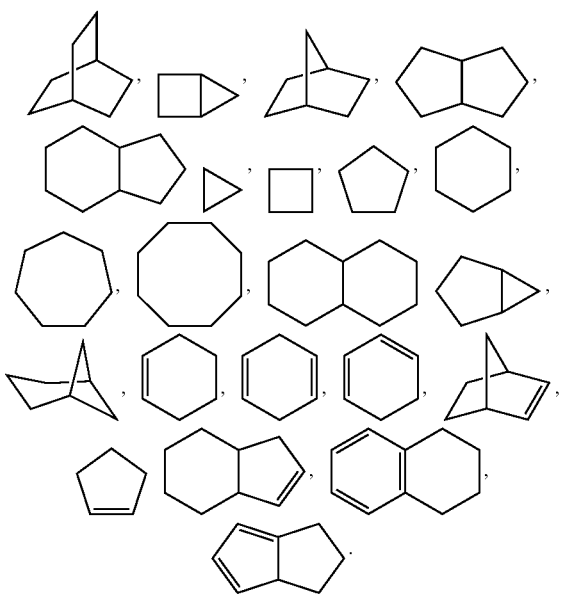

In some embodiments, depending on the structure, a cycloalkyl group is a monoradical or a diradical (e.g., a cycloalkylene group).

The term "cycloalkyl groups" as used herein refers to groups which are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxyl, hydroxyalkylene, mercapto, oxo, —NR$_A$R$_A$, and (NR$_A$R$_B$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "carbocyclic" as used herein, refers to a compound which contains one or more covalently closed ring structures, and that the atoms forming the backbone of the ring are all carbon atoms The term "carbocycle" as used herein, refers to a ring, wherein each of the atoms forming the ring is a carbon atom. Carbocylic rings include those formed by three, four, five, six, seven, eight, nine, or more than nine carbon atoms. Carbocycles are optionally substituted.

The term "alkoxyalkyl" as used herein, means at least one alkoxy group, as defined herein, appended to the parent molecular moiety through an alkyl group, as defined herein. Illustrative examples of alkoxyalkyl include, but are not limited to, 2-methoxyethyl, 2-ethoxyethyl, tert-butoxyethyl and methoxymethyl.

The term "alkoxycarbonyl" as used herein, means an alkoxy group, as defined herein, appended to the parent molecular moiety through a carbonyl group, as defined herein. Illustrative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkylcarbonyl" as used herein, means an alkyl group, as defined herein, appended to the parent molecular moiety through a carbonyl group, as defined herein. Illustrative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Illustrative examples of alkylcarbonyloxy include, but are not limited to, acetyloxy, ethylcarbonyloxy, and tert-butylcarbonyloxy.

The term "alkylthio" or "thioalkoxy" as used herein, means an alkyl group, as defined herein, appended to the parent molecular moiety through a sulfur atom. Illustrative examples of alkylthio include, but are not limited to, methylthio, ethylthio, butylthio, tert-butylthio, and hexylthio.

The term "alkylthioalkyl" as used herein, means an alkylthio group, as defined herein, appended to the parent molecular moiety through an alkyl group, as defined herein. Illustrative examples of alkylthioalkyl include, but are not limited to, methylthiomethyl, 2-(ethylthio)ethyl, butylthiomethyl, and hexylthioethyl.

The term "alkynyl" as used herein, means a straight, branched chain hydrocarbon containing from 2-10 carbons and containing at least one carbon-carbon triple bond. In some embodiments, alkynyl groups are optionally substituted. Illustrative examples of alkynyl include, but are not limited to, acetylenyl, 1-propynyl, 2-propynyl, 3-butynyl, 2-pentynyl, and 1-butynyl.

The term "aromatic" as used herein, refers to a planar ring having a delocalized π-electron system containing 4n+2π electrons, where n is an integer. In some embodiments, aromatic rings are formed by five, six, seven, eight, nine, or more than nine atoms. In other embodiments, aromatics are optionally substituted. The term includes monocyclic or fused-ring polycyclic (i.e., rings which share adjacent pairs of carbon atoms) groups.

The term "aryl" as used herein, refers to an aromatic ring wherein each of the atoms forming the ring is a carbon atom. In some embodiments, aryl rings are formed by five, six, seven, eight, nine, or more than nine carbon atoms. Examples of aryl groups include, but are not limited to phenyl, naphthalenyl, phenanthrenyl, anthracenyl, fluorenyl, and indenyl.

In some embodiments, the term "aryl" as used herein means an aryl group that is optionally substituted with one, two, three, four or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carbonyl, cyano, formyl, haloalkoxy, haloalkyl, halogen, hydroxyl, hydroxyalkylene, mercapto, nitro, —NR$_A$R$_A$, and (NR$_A$R$_B$)carbonyl.

The term "arylalkyl" as used herein, means an aryl group, as defined herein, appended to the parent molecular moiety through an alkyl group, as defined herein. Illustrative examples of arylalkyl include, but are not limited to benzyl, 2-phenylethyl, -phenylpropyl, 1-methyl-3-phenylpropyl, and 2-naphth-2-ylethyl.

The term "carbonyl" as used herein, means a —C(O)— group.

The term "carboxy" as used herein, means a —COOH group.

The term "cyano" as used herein, means a —CN group.

The term "formyl" as used herein, means a —C(O)H group.

The term "halo" or "halogen" as used herein, means a —Cl, —Br, —I or —F.

The term "mercapto" as used herein, means a —SH group.

The term "nitro" as used herein, means a —NO$_2$ group.

The term "hydroxy" as used herein, means a —OH group.

The term "oxo" as used herein, means a =O group.

The term "bond" or "single bond" as used herein, refers to a chemical bond between two atoms, or two moieties when the atoms joined by the bond are considered to be part of larger substructure.

The terms "haloalkyl," "haloalkenyl," "haloalkynyl" and "haloalkoxy" as used herein, include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

The term "alkylamine" refers to the —N(alkyl)$_x$H$_y$ group, where x and y are selected from among x=1, y=1 and x=2, y=0. In some embodiments, when x=2, the alkyl groups, taken together with the N atom to which they are attached, optionally form a cyclic ring system.

The term "amide" as used herein, is a chemical moiety with the formula —C(O)NHR or —NHC(O)R, where R is selected from among hydrogen, alkyl, cycloalkyl, aryl, heteroaryl (bonded through a ring carbon) and heterocycloalkyl (bonded through a ring carbon). In some embodiments, an amide moiety forms a linkage between an amino acid or a peptide molecule and a compound described herein, thereby forming a prodrug. In some embodiments, any amine, or carboxyl side chain on the compounds described herein is amidified.

The term "ester" refers to a chemical moiety with formula —COOR, where R is selected from among alkyl, cycloalkyl, aryl, heteroaryl (bonded through a ring carbon) and heterocycloalkyl (bonded through a ring carbon). In some embodiments, any hydroxy, or carboxyl side chain on the compounds described herein is esterified.

The terms "heteroalkyl" "heteroalkenyl" and "heteroalkynyl" as used herein, include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" as used herein refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms are all the same as one another, or some or all of the two or more heteroatoms are each different from the others.

The term "ring" as used herein, refers to any covalently closed structure. Rings include, for example, carbocycles (e.g., aryls and cycloalkyls), heterocycles (e.g., heteroaryls and heterocycloalkyls), aromatics (e.g. aryls and heteroaryls), and non-aromatics (e.g., cycloalkyls and heterocycloalkyls). In some embodiments, rings are optionally substituted. In some embodiments, rings form part of a ring system.

As used herein, the term "ring system" refers to two or more rings, wherein two or more of the rings are fused. The term "fused" refers to structures in which two or more rings share one or more bonds.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In some embodiments, the polycyclic heteroaryl group is fused or non-fused. Illustrative of heteroaryl groups include, but are not limited to, the following moieties:

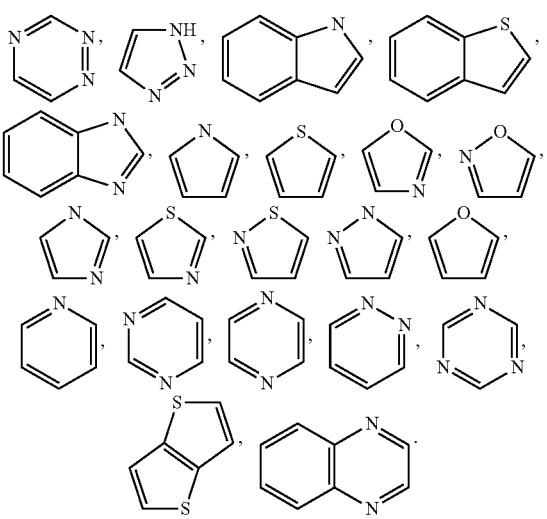

In some embodiments, depending on the structure, a heteroaryl group is a monoradical or a diradical (i.e., a heteroarylene group).

The term "unsubstituted or substituted heteroaryl" means heteroaryl groups that are substituted with 0, 1, 2, 3, 4 or 5 substituents independently selected from, for example, alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, sulfinyl, sulfonyl, nitro, amino, amido and other suitable moiety. In some embodiments, substituents are independently selected from halogen, $C_1$-$C_6$ alkyl, $C_1$-$C_6$ haloalkyl (e.g. $CF_3$), OH, $NO_2$, CN, $C_1$-$C_6$ alkoxy, $C_1$-$C_6$ haloalkoxy, —NHSO$_2$R$_6$, —SO$_2$NHR$_6$, —NHCOR$_6$, —NH$_2$, —NR$_6$R$_7$, —SR$_6$, —S(O)R$_6$, —S(O)$_2$R$_6$, —CO$_2$R$_6$, —CONR$_6$R$_7$, wherein R$_6$ and R$_7$ are independently selected from a group consisting of hydrogen, and an optionally substituted $C_1$-$C_6$ alkyl.

The term "heteroarylalkyl" as used herein, means a heteroaryl, as defined herein, appended to the parent molecular moiety through an alkyl group, as defined herein. Illustrative examples of heteroarylalkyl include, but are not limited to, pyridinylmethyl.

The term "heterocycloalkyl" or "non-aromatic heterocycle" as used herein, refers to a non-aromatic ring wherein one or more atoms forming the ring is a heteroatom. A "heterocycloalkyl" or "non-aromatic heterocycle" group refers to a cycloalkyl group that includes at least one heteroatom selected from nitrogen, oxygen and sulfur. In some embodiments, the radicals are fused with an aryl or heteroaryl. In some embodiments, heterocycloalkyl rings are formed by three, four, five, six, seven, eight, nine, or more than nine atoms. In some embodiments, heterocycloalkyl rings are optionally substituted. In certain embodiments, heterocycloalkyls contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include, but are not limited to

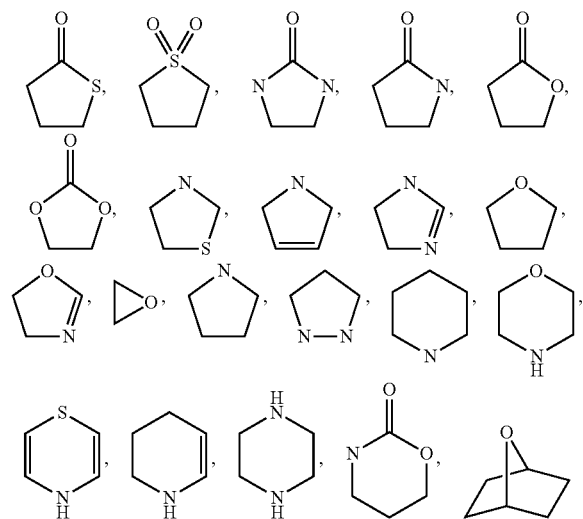

The term heterocycloalkyl also includes all ring forms of the carbohydrates, including but not limited to the monosaccharides, the disaccharides and the oligosaccharides.

The term "heterocycle" refers to heteroaryl and heterocycloalkyl used herein, refers to groups containing one to four heteroatoms each selected from O, S and N, wherein each heterocycle group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. In some embodiments, it is understood that the heterocycle ring has additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In some embodiments, in heterocycles that have two or more heteroatoms, those two or more heteroatoms are the same or different from one another. In some embodiments, heterocycles are optionally substituted. In some embodiments, binding to a heterocycle is at a heteroatom or via a carbon atom. Heterocycloalkyl groups include groups having only 4 atoms in their ring system, but heteroaryl groups must have at least 5 atoms in their ring system. The heterocycle groups include benzo-fused ring systems. An example of a 4-membered heterocycle group is azetidinyl (derived from azetidine). An example of a 5-membered heterocycle group is thiazolyl. An example of a 6-membered heterocycle group is pyridyl, and an example of a 10-membered heterocycle group is quinolinyl. Examples of heterocycloalkyl groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. In some embodiments, the foregoing groups, as derived from the groups listed above, are C-attached or N-attached where such is possible. For instance, in some embodiments, a group derived from pyrrole is pyrrol-1-yl (N-attached) or pyrrol-3-yl (C-attached). Further, in some embodiments, a group derived from imidazole is imidazol-1-yl or imidazol-3-yl (both N-attached) or imidazol-2-yl, imidazol-4-yl or imidazol-5-yl (all C-attached). The heterocycle groups include benzo-fused ring systems and ring systems substituted with one or two oxo (═O) moieties such as pyrrolidin-2-one. In some embodiments, depending on the structure, a heterocycle group is a monoradical or a diradical (i.e., a heterocyclene group).

The heterocycles described herein are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alynyl, carboxy, cyano, formyl, haloalkoxy, haloalkyl, halogen, hydroxyl, hydroxyalkylene, mercapto, nitro, amino, and amido moieties.

The term "heterocycloalkoxy" refers to a heterocycloalkyl group, as defined herein, appended to the parent molecular moiety through an alkoxy group.

The term "heterocycloalkylthio" refers to a heterocycloalkyl group, as defined herein, appended to the parent molecular moiety through an alkylthio group.

The term "heterocyclooxy" refers to a heterocycloalkyl group, as defined herein, appended to the parent molecular moiety through an oxygen atom.

The term "heterocyclothio" refers to a heterocycloalkyl group, as defined herein, appended to the parent molecular moiety through a sulfur atom.

The term "heteroarylalkoxy" refers to a heteroaryl group, as defined herein, appended to the parent molecular moiety through an alkoxy group.

The term "heteroarylalkylthio" refers to a heteroaryl group, as defined herein, appended to the parent molecular moiety through an alkylthio group.

The term "heteroaryloxy" refers to a heteroaryl group, as defined herein, appended to the parent molecular moiety through an oxygen atom.

The term "heteroarylthio" refers to a heteroaryl group, as defined herein, appended to the parent molecular moiety through a sulfur atom.

In some embodiments, the term "membered ring" embraces any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "non-aromatic 5, 6, 7, 8, 9, 10, 11 or 12-bicyclic heterocycle" as used herein, means a heterocycloalkyl, as defined herein, consisting of two carbocyclic rings, fused together at the same carbon atom (forming a spiro structure) or different carbon atoms (in which two rings share one or more bonds), having 5 to 12 atoms in its overall ring system, wherein one or more atoms forming the ring is a heteroatom. Illustrative examples of non-aromatic 5, 6, 7, 8, 9, 10, 11, or 12-bicyclic heterocycle ring include, but are not limited to, 2-azabicyclo[2.2.1]heptanyl, 7-azabicyclo[2.2.1]heptanyl, 2-azabicyclo[3.2.0]heptanyl, 3-azabicyclo[3.2.0]heptanyl, 4-azaspiro[2.4]heptanyl, 5-azaspiro[2.4]heptanyl, 2-oxa-5-azabicyclo[2.2.1]heptanyl, 4-azaspiro[2.5]octanyl, 5-azaspiro[2.5]octanyl, 5-azaspiro[3.4]octanyl, 6-azaspiro[3.4]octanyl, 4-oxa-7-azaspiro[2.5]octanyl, 2-azabicyclo[2.2.2]octanyl, 1,3-diazabicyclo[2.2.2]octanyl, 5-azaspiro[3.5]nonanyl, 6-azaspiro[3.5]nonanyl, 5-oxo-8-azaspiro[3.5]nonanyl, octahydrocyclopenta[c]pyrrolyl, octahydro-1H-quinolizinyl, 2,3,4,6,7,9a-hexahydro-1H-quinolizinyl, decahydropyrido[1,2-a]azepinyl, decahydro-1H-pyrido[1,2-a]azocinyl, 1-azabicyclo[2.2.1]heptanyl, 1-azabicyclo[3.3.1]nonanyl, quinuclidinyl, and 1-azabicyclo[4.4.0]decanyl.

The term hydroxyalkylene" as used herein, means at least one hydroxyl group, as defined herein, is appended to the parent molecular moiety through an alkylene group, as defined herein. Illustrative examples of hydroxyalkylene include, but not limited to hydroxymethylene, 2-hydroxyethylene, 3-hydroxypropylene and 4-hydroxyheptylene.

The term "$NR_ANR_B$" as used herein, means two group, $R_A$ and $R_B$, which are appended to the parent molecular moiety through a nitrogen atom. $R_A$ and $R_B$ are each independently hydrogen, alkyl, and alkylcarbonyl. Illustrative examples of $NR_AR_B$ include, but are not limited to, amino, methylamino, acetylamino, and acetylmethylamino.

The term "$(NR_ANR_B)$carbonyl" as used herein, means a $R_AR_B$, group, as defined herein, appended to the parent molecular moiety through a carbonyl group, as defined herein. Illustrative examples of $(NR_AR_B)$carbonyl include, but are not limited to, aminocarbonyl, (methylamino)carbonyl, (dimethylamino)carbonyl, and (ethylmethylamino)carbonyl.

The term "$NR_CNR_D$" as used herein, means two group, $R_C$ and $R_D$, which are appended to the parent molecular moiety through a nitrogen atom. $R_C$ and $R_D$ are each independently hydrogen, alkyl, and alkylcarbonyl. Illustrative examples of $NR_CR_D$ include, but are not limited to, amino, methylamino, acetylamino, and acetylmethylamino.

The term "$(NR_CNR_D)$carbonyl" as used herein, means a $R_CR_D$, group, as defined herein, appended to the parent molecular moiety through a carbonyl group, as defined herein. Illustrative examples of $(NR_CR_D)$carbonyl include, but are not limited to, aminocarbonyl, (methylamino)carbonyl, (dimethylamino)carbonyl, and (ethylmethylamino)carbonyl.

As used herein, the term "mercaptyl" refers to a (alkyl)S— group.

As used herein, the term "moiety" refers to a specific segment or functional group of a molecule. Chemical moieties are often recognized chemical entities embedded in or appended to a molecule.

As used herein, the term "sulfinyl" refers to a —S(=O)—R, where R is selected from the group consisting of alkyl, cycloalkyl, aryl, heteroaryl (bonded through a ring carbon) and heterocycloalkyl (bonded through a ring carbon).

As used herein, the term "sulfonyl" refers to a —S(=O)$_2$—R, where R is selected from the group consisting of alkyl, cycloalkyl, aryl, heteroaryl (bonded through a ring carbon) and heterocycloalkyl (bonded through a ring carbon).

As used herein, the term "O carboxy" refers to a group of formula RC(=O)O—.

As used herein, the term "C carboxy" refers to a group of formula —C(=O)OR.

As used herein, the term "acetyl" refers to a group of formula —C(=O)CH$_3$.

As used herein, the term "trihalomethanesulfonyl" refers to a group of formula X$_3$CS(=O)$_2$— where X is a halogen.

As used herein, the term "isocyanato" refers to a group of formula —NCO.

As used herein, the term "thiocyanato" refers to a group of formula —CNS.

As used herein, the term "isothiocyanato" refers to a group of formula —NCS.

As used herein, the term "S sulfonamido" refers to a group of formula —S(=O)$_2$NR$_2$.

As used herein, the term "N sulfonamido" refers to a group of formula RS(=O)$_2$NH—.

As used herein, the term "trihalomethanesulfonamido" refers to a group of formula X$_3$CS(=O)$_2$NR—.

As used herein, the term "O carbamyl" refers to a group of formula —OC(=O)NR$_2$.

As used herein, the term "N carbamyl" refers to a group of formula ROC(=O)NH—.

As used herein, the term "O thiocarbamyl" refers to a group of formula —OC(=S)NR$_2$.

As used herein, the term "N thiocarbamyl" refers to a group of formula ROC(=S)NH—.

As used herein, the term "C amido" refers to a group of formula —C(=O)NR$_2$.

As used herein, the term "N amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

The term "substituted" means that the referenced group is optionally substituted (substituted or unsubstituted) with one or more additional group(s) individually and independently selected from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, haloalkyl, haloalkoxy, perhaloalkyl, perfluoroalkyl, silyl, amido, urea, thiourea, and amino, including mono- and di-substituted amino groups, and the protected derivatives thereof. By way of example an optional substituents is $L_sR_s$ wherein each $L_s$, is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R$_S$ is independently selected from H, (substituted or unsubstituted lower alkyl), (substituted or unsubstituted lower cycloalkyl), heteroaryl, or heteroalkyl.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

The term "optionally substituted" as defined herein, means the referenced group is substituted with zero, one or more substituents as defined herein.

The term "protected-hydroxy" refers to a hydroxy group protected with a hydroxy protecting group, as defined above.

In some embodiments, compounds of the described herein exist as stereoisomers, wherein asymmetric or chiral centers are present. Stereoisomers are designated (R) or (S) depending on the configuration of substituents around the chiral carbon atom. The term (R) and (S) used herein are configurations as defined in IUPAC 1974 Recommendations for Section E, Fundamental Stereochemistry, Pure Appl. Chem., (1976), 45:13-30, hereby incorporated by reference. The embodiments described herein specifically includes the various stereoisomers and mixtures thereof. Stereoisomers include enantiomers, diastereomers, and mixtures of enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In some embodiments, the compounds described herein exist in unsolvated as well as solvated forms with pharmaceutically acceptable solvents such as water, ethanol, and the like. The solvated forms of the compounds presented herein are also considered to be disclosed herein.

Throughout the specification, groups and substituents thereof are chosen, in certain embodiments, to provide stable moieties and compounds.

EXAMPLE

Even though all three tautomeric structures can exist, all the generic structures and all the examples having 1,2,4-triazole moiety are shown only in one tautomeric form, such as 4H-1,2,4-triazole for simplicity and for the comparison with its direct analogues, such as examples containing 1,3,4-oxadiazole moiety. The prevailing tautomeric structure depends on the substituents on the triazole moiety and on the reaction conditions. As has been shown in the literature, 1H-1,2,4-triazole is usually the most common tautomeric form, especially if an amino substituent is attached to the ring. Using only 4H-tautomeric form to draw the structures for the sake of simplicity, does not imply that the compounds of the examples that follow necessarily exist in that particular tautomeric form. Using this approach, the IUPAC names for the examples below are provided for 4H-tautomeric form only, however it is understood, that upon the elucidation of the exact tautomeric structure the numbering of the substituents may differ from the one that is provided.

Example 1

Synthesis of the 1,2,4-Triazole Cores

Synthesis of the 1,2,4-triazole cores was carried out as shown in the scheme below. Detailed experimental procedures and analytical data follow.

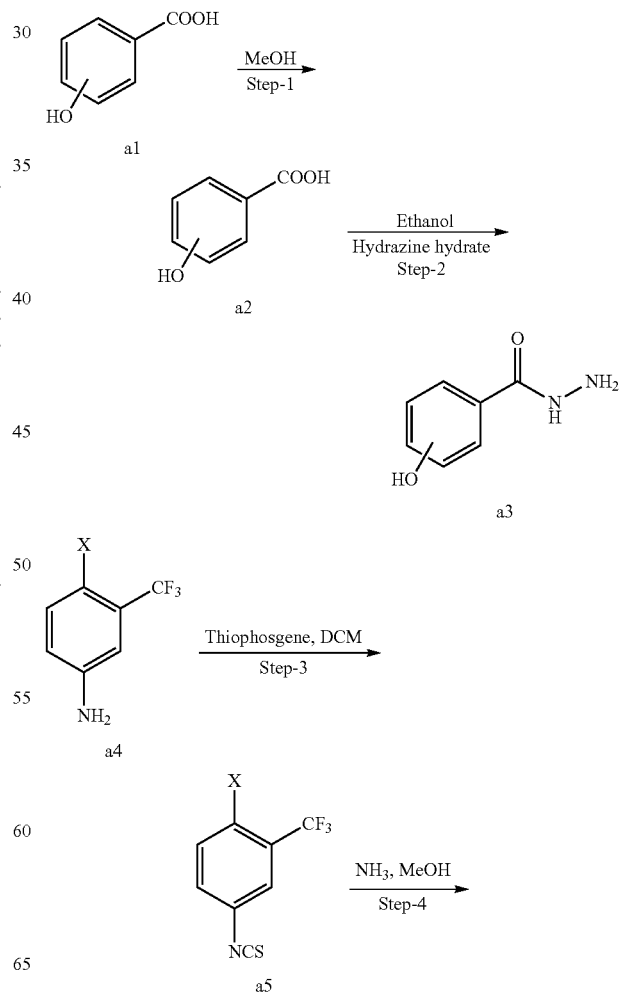

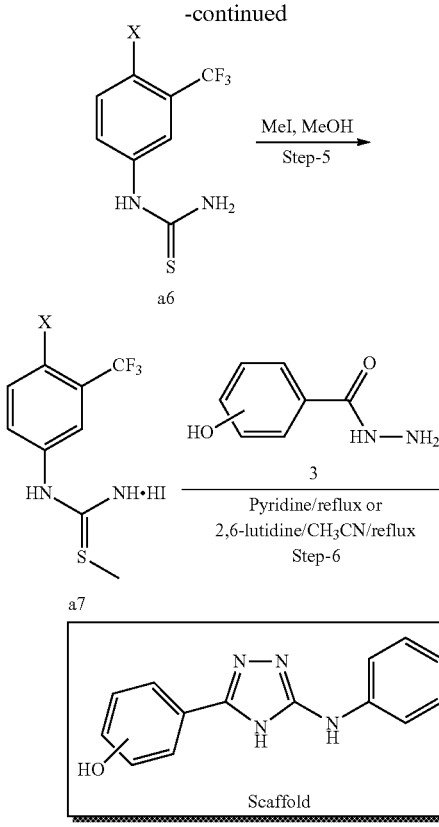

Experimental Procedures

Step-2: Preparation of Hydroxy Benzohydrazide

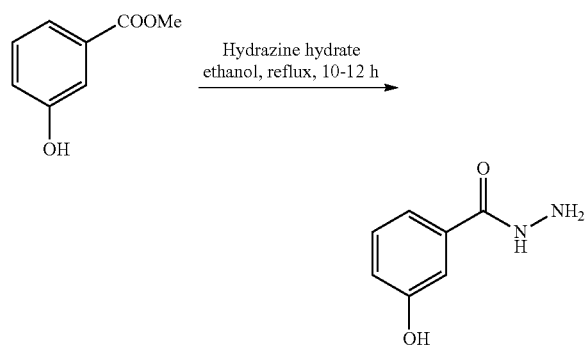

| S. No. | Chemical | Mol. Wt. | Amount | mmol | Molar Ratio |
|---|---|---|---|---|---|
| 1 | Methyl 3-hydroxy benzoate | 152 | 7 g | 46.05 | 1 |
| 2 | Hydrazine hydrate | 50 | 23 g | 460.4 | 10 |
| 3 | Ethanol | | 150 mL | | |

To a stirred solution of methyl 3-hydroxy benzoate (7 g, 46.05 mmol) in ethanol (150 mL) was added hydrazine hydrate (23 g, 460.5 mmol) at room temperature and the reaction mixture was refluxed for 10-12 hrs. The reaction was monitored by TLC; upon disappearance of the starting material, the reaction mass was cooled to room temperature and the ethanol was distilled out to get the crude product. To this crude product was added acetone (20 mL) at 10-15° C. and this was stirred in n-hexane (100 mL) for 30 min. The white solid that precipitated out was filtered and dried under vacuum at 55° C. to obtain the pure product (Yield: 6.9 g, 85.71% of theoretical).

Yield: 95.71%
HPLC Purity: 98.7%
$^1$H NMR: Consistent with the structure.
LCMS: m/z=153 (MH+)

Step-3: Preparation of 3-(Trifluoromethyl)Phenyl Isothiocyanate

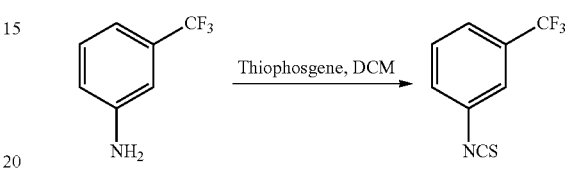

| S. No. | Chemical | Mol. Wt. | Amount | mmol | Molar Ratio |
|---|---|---|---|---|---|
| 1 | 3-(Trifluoromethyl)aniline | 161 | 20 g | 124.2 | 1 |
| 2 | Thiophosgene | 114 | 21.24 | 186.4 | 1.5 |
| 3 | DCM | | 100 mL | | 5 Vol. |

To a stirred solution of 3-(trifluoromethyl)aniline (20 g, 124.2 mmol) in DCM (100 mL) was added thiophosgene (21.24 g, 186.4 mmol) at 5-10° C. and the reaction mixture was stirred at room temperature for 1-2 h. The reaction was monitored by TLC (mobile phase-40% ethyl acetate in n-Hexane, Rf. S.M.-0.25, product-0.5). Upon disappearance of the starting material, the reaction mass was diluted with DCM, the oranic layer was washed with 10% NaHCO$_3$, water and brine. The organic layer was dried and concentrated in vacuo at a temperature lower than 45° C. to afford the product as a yellow oil (Yield: 19.2 g, 76.19% of theoretical).

Yield: 76.19%
$^1$H NMR: Consistent with the structure

Step-4: Preparation of (3-Trifluoromethyl)Phenyl Thiourea

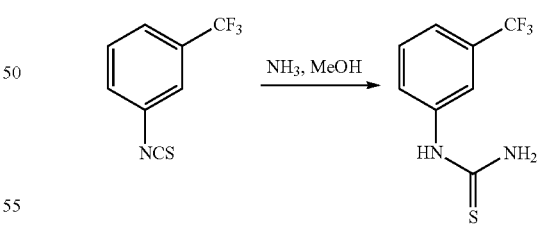

| S. No. | Chemical | Mol. Wt. | Amount | mmol | Molar Ratio |
|---|---|---|---|---|---|
| 1 | 1-Isothiocyanato-3-(trifluoromethyl)benzene | 203 | 10 g | 49.26 | 1 |
| 2 | Aq. Ammonia (25%) | 17 | 10.05 g ~35 mL | 591 | 12 |
| 3 | Methanol | | 100 mL | | 10 Vol |

To a stirred solution of 1-isothiocyanato-3-(trifluoromethyl)benzene (10 g, 49.26 mmol) in Methanol (100 mL) was added aq.ammonia (6.69 g, 394 mmol) dropwise at 5° C.-10° C. After complete addition of ammonia, the reaction mixture was stirred at room temperature for 2-3 h. When TLC (mobile phase-40% ethyl acetate in n-Hexane, Rf. S.M.-0.80, product-0.2) showed absence of starting material and formation of product, methanol was concentrated, water was added and extracted with ethyl acetate. The organic layer was washed with brine, dried over $Na_2SO_4$ and concentrated to give the pure product as an off-white solid (Yield: 9.2 g, 84.94% of theoretical).
Yield: 84.94%
HPLC Purity: 99.75%
1H NMR: Consistent with structure
LCMS: MH+: 221 (Mol. Wt. 220)

Step-5: Preparation of the S-Methylisothiourea Hydroiodide Salt

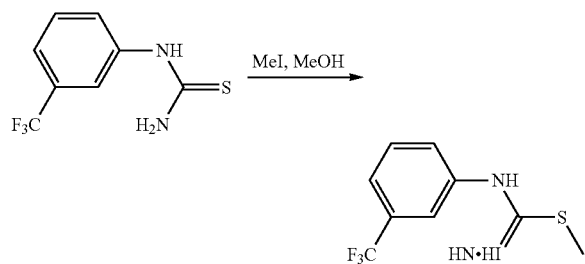

| S. No. | Chemical | Mol. Wt. | Amount | mmol | Molar Ratio |
|---|---|---|---|---|---|
| 1 | 1-(3-(Trifluoromethyl)phenyl) thiourea | 220 | 15 g | 68 | 1 |
| 2 | Methyl Iodide | 148 | 15.13 g | 102 | 1.5 |
| 3 | Methanol | | 150 mL | | 10 Vol |

To a solution of 1-(3-(trifluoromethyl)phenyl) thiourea (15 g, 68 mmol) in methanol (150 mL) was added methyl iodide (15.13 g, 102 mmol) dropwise at room temperature. The reaction mixture was stirred at 50° C. for 7-8 hrs. When TLC (mobile phase-5% methanol in chloroform, Rf. S.M.-0.30, product-0.2) showed absence of starting material and formation of product, methanol was concentrated to get the pure product as an off white solid (Yield: 22 g, 89.39% of theoretical).
Yield: 89.39%
HPLC Purity: 95.84%,
1H NMR: Consistent with structure
LCMS: MH+: 235 (Mol. Wt. 234)

Step-6: Preparation of the Scaffold—Method 1

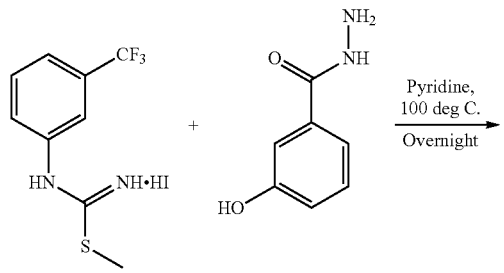

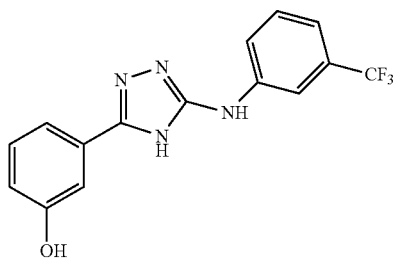

| S. No. | Chemical | Mol. Wt. | Amount | mmol | Molar Ratio |
|---|---|---|---|---|---|
| 1 | S-Methyl-3-(trifluoromethyl)phenyl isothiourea hydroiodide | 362 | 5 g | 13.81 | 1 |
| 2 | 3-Hydroxy benzohydrazide | 152 | 2.32 g | 15.26 | 1.1 |
| 3 | Pyridine (anhyd.) | | 30 mL | | 6 Vol |

To a suspension of methyl S-Methyl-3-(trifluoromethyl) phenylisothiourea hydroiodide (5 g, 13.81 mmol) in anhydrous pyridine (30 mL) was added 3-hydroxy benzohydrazide (2.32 g, 15.26 mmol) under $N_2$ atmosphere. After complete addition of hydrazide, the reaction mixture was stirred at 100° C. for 10-12 h. When TLC (mobile phase-10% methanol in chloroform, Rf. S.M.-0.20, product-0.4) showed absence of starting material, the reaction mixture was cooled to room temperature and the pyridine was concentrated under vacuum to get the crude product (yellow oil). This was purified by column chromatography to afford the desired scaffold in a pure form.
Yield: 42.35%
HPLC Purity: 98.08%
1H NMR: Consistent with structure
LCMS: MH+321 (Mol. Wt 320)

Step-6: Preparation of the Scaffold—Method 2

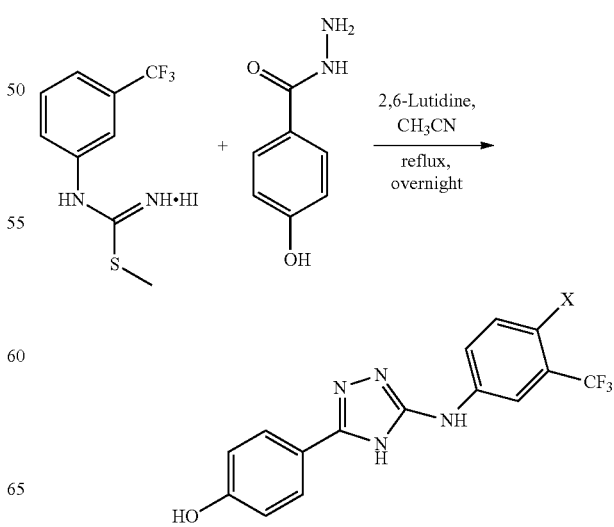

| S. No. | Chemical | Mol. Wt. | Amount | mmol | Molar Ratio |
|---|---|---|---|---|---|
| 1 | S-Methyl-3-(trifluoromethyl)phenyl isothiourea hydroiodide | 362 | 6 g | 16.57 | 1 |
| 2 | 4-hydroxy benzohydrazide | 152 | 3.02 g | 19.8 | 1.2 |
| 3 | 2,6-Lutidine | 107 | 3.53 g | 33 | 2 |
| 4 | CH$_3$CN | | 60 mL | | 10 Vol |

To a suspension of methyl S-Methyl-3-(trifluoromethyl) phenylisothiourea hydroiodide (6 g, 16.57 mmole) in Acetonitrile (60 mL) was added 2,6-lutidine (3.53 g, 33 mmol) under N$_2$↑ atmosphere at room temperature followed by 4-hydroxy benzohydrazide (3.02 g, 19.8 mmol) and stirred at room temperature for 15 min. After complete addition of hydrazide reaction mixture was stirred at 80° C. for 18-20 hrs. When TLC (mobile phase-10% methanol in chloroform, Rf. S.M.-0.20, product-0.5) showed absence of starting material and formation of product, the mixture was cooled to room temperature and acetonitrile was removed under vacuum. The residue was taken in ethyl acetate and the organic layer was washed with water (2×), followed by 10% citric acid solution (2×) and finally with brine. Organic layer was separated and dried over Na$_2$SO$_4$ (solid) and concentrated to give crude product. The crude product was purified by column chromatography to afford desired product (3.1 g).

Yield: 58.84%

HPLC Purity: 96%.

LCMS: MH+321 (Mol. Wt 320)

Example 2

Synthesis of the 1,3,4-oxadiazole cores

Synthesis of the 1,3,4-oxadiazole cores was carried out as shown in the scheme below.

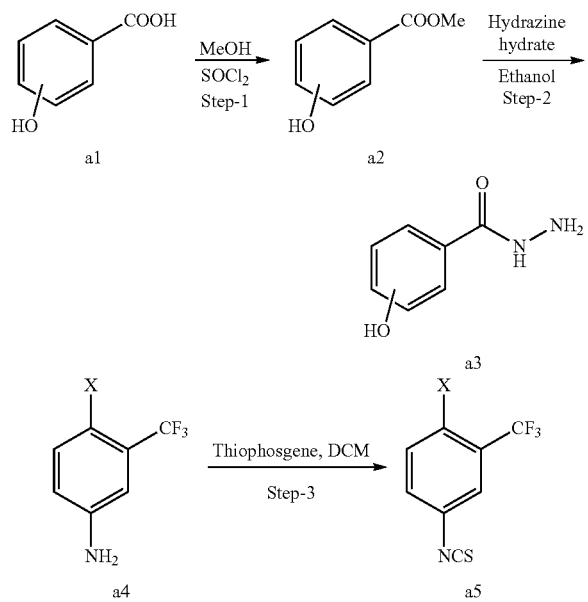

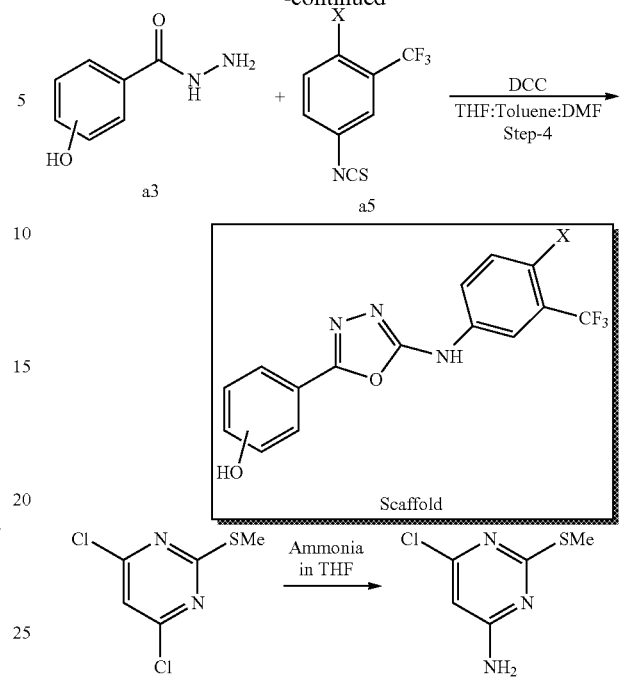

Experimental Procedures

Step-4: Preparation of the Scaffold

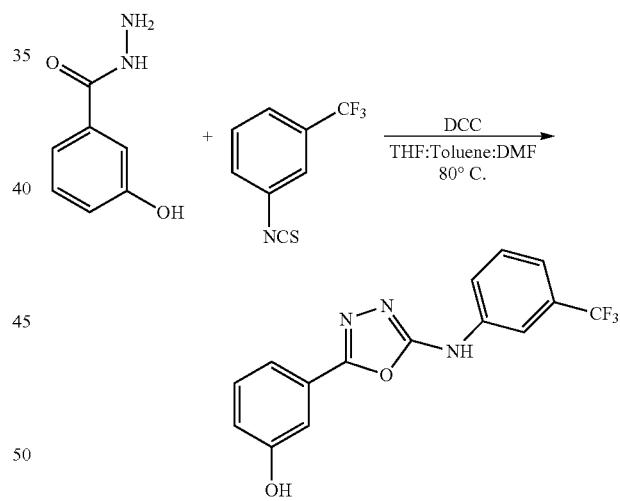

| S. No. | Chemical | Mol. Wt. | Amount | mmol | Molar Ratio |
|---|---|---|---|---|---|
| 1 | 3-Hydroxy benzohydrazide | 152 | 1 g | 6.5 | 1 |
| 2 | 1-Isothiocyanato-3-(trifluoromethyl)benzene | 203 | 1.33 g | 6.5 | 1 |
| 3 | DCC | 206 | 1.49 g | 7.2 | 1.1 |
| 4 | Toluene | | 5 mL | | |
| 5 | THF | | 5 mL | | |
| 6 | DMF | | 5 mL | | |

To a suspension of methyl 3-hydroxy benzohydrazide (1 g, 6.5 mmol) in THF:Toluene:DMF (5 mL) each was added 1-Isothiocyanato-3-(trifluoromethyl)benzene (1.33 g, 6.5 mmol) under N₂↑ atmosphere at room temperature. After complete addition of isothiocyanate reaction mixture was stirred at 80° C. for 30 min. Then DCC (1.49 g, 7.23 mmol) was added and reaction mixture was stirred at 80° C. for 5-6h. When TLC (mobile phase-5% methanol in chloroform, Rf. S.M.-0.30, product-0.5) showed absence of starting material and formation of product, the reaction mixture was cooled to room temperature; water was added and the reaction mixture was extracted with ethyl acetate (3×50 mL). The combined organic layer was dried over Na₂SO₄ and concentrated in vacuo to give the crude product. This was purified by column chromatography to afford desired product (750 mg).
Yield: 35.5%
HPLC Purity: 90.6%
1H NMR: Consistent with structure
LCMS: MH+322 (Mol. Wt 321)

Example 3

Synthesis of the 1,3,4-thiadiazole Cores

Synthesis of the 1,3,4-thiadiazole cores was carried out as shown in the scheme below.

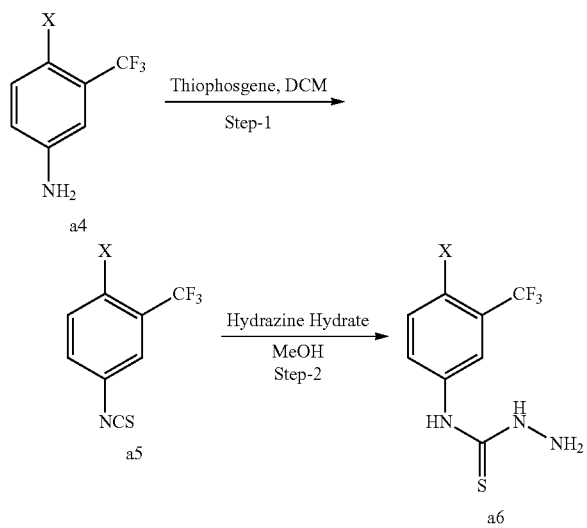

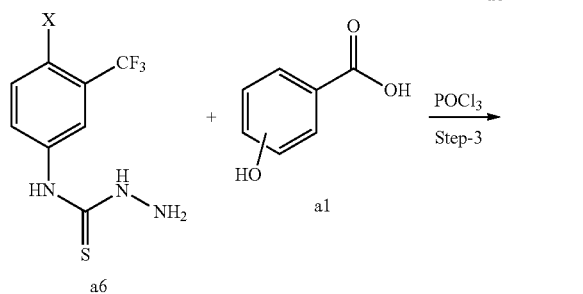

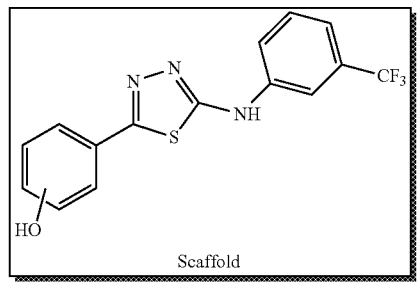

Experimental Procedures for the Synthesis of the 1,3,4-thiadiazole Cores

Step-2: Preparation of N-(3-(trifluoromethyl)phenyl)hydrazinecarbothioamide

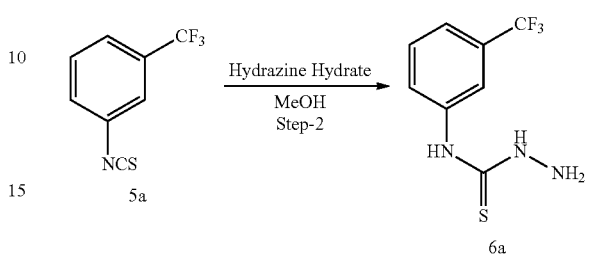

| S. No. | Chemical | Mol. Wt. | Amount | mmol | Molar Ratio |
|---|---|---|---|---|---|
| 1 | 1-Isothiocyanato-3-(trifluoromethyl)benzene | 203 | 250 mg | 1.23 | 1 |
| 2 | Hydrazine hydrate | 50 | 308 mg | 6.16 | 5 |
| 3 | Methanol | | 5 mL | | |

To a stirred solution of 1-isothiocyanato-3-(trifluoromethyl)benzene (250 mg, 1.23 mmol) in methanol (5 mL) was added hydrazine hydrate (307 mg, 6.16 mmol) dropwise at 5° C.-10° C. After complete addition of hydrazine hydrate, the reaction mixture was stirred at room temperature for 2-3 h. When TLC (mobile phase-30% ethyl acetate in n-Hexane, Rf. S.M.-0.80, product-0.2) showed absence of starting material, the methanol was concentrated, water was added and extracted with ethyl acetate. The combined organic layer was washed with brine, dried over Na₂SO₄ and concentrated to give the pure product as an off white solid (Yield: 200 mg, 69.4% of theoretical).

Yield: 69.4%
LCMS: MH+236 (Mol. Wt.235)

Step-3: Preparation of the Scaffold

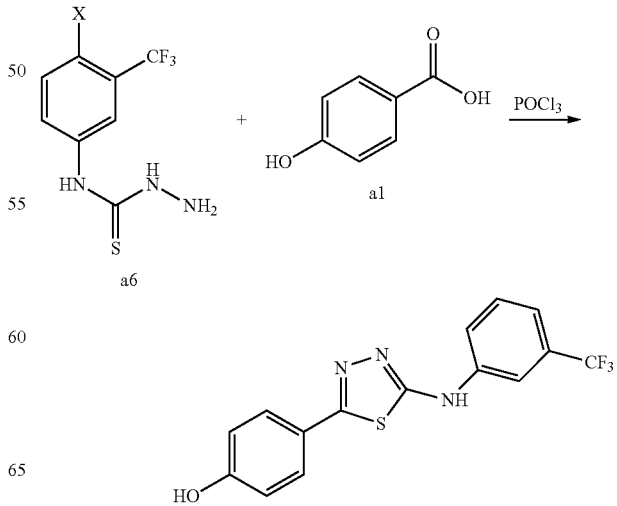

| S. No. | Chemical | Mol. Wt. | Amount | mmol | Molar Ratio |
|---|---|---|---|---|---|
| 1 | N-(3-(trifluoromethyl)phenyl) hydrazinecarbothioamide | 235 | 350 mg | 1.5 | 1 |
| 2 | 4-Hydroxy benzoic acid | 138 | 246 mg | 1.78 | 1.2 |
| 3 | POCl$_3$ | | 2 mL | | |

A solution of N-(3-(trifluoromethyl)phenyl)hydrazinecarbothioamide (350 mg, 1.5 mmol), 4-hydroxy benzoic acid (246 mg, 1.78 mmol) in POCl$_3$ (2 mL) was stirred for 5-6 hrs at 80° C. When TLC (mobile phase-10% methanol in chloroform, Rf. S.M.-0.20, product-0.5) shows absence of starting material and formation product, the reaction mixture was cooled to 10-15° C. and quenched with ice water; the solid that precipitated was filtered and dried in Oven at 50° C. the product was purified by column chromatography to obtain an off white solid (Yield: 130 mg, 25.9% of theoretical).

Yield: 25.9%

1H NMR: Consistent with structure

LCMS: MH+338 (Mol. Wt 337)

Example 3

Synthesis of the Inverted Aminotriazole Cores

Synthesis of the 1,2,4-triazole cores was carried out as shown in the scheme below.

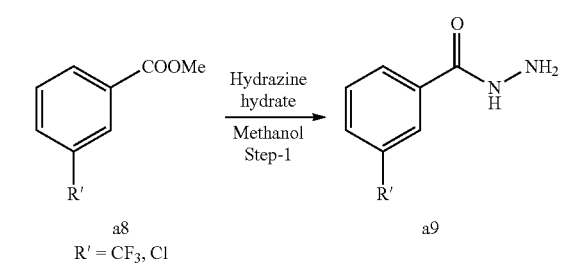

Experimental Procedures

Experimental procedures followed were the same as described for the synthesis of the 1,2,4-triazole cores. Analytical data for the intermediates and the scaffolds are provided below.

(I) Preparation of the Scaffold K43

Step-1: Preparation of the Hydrazide 9a

Steps-2 & 3: Preparation of the Thiourea 12a

-continued

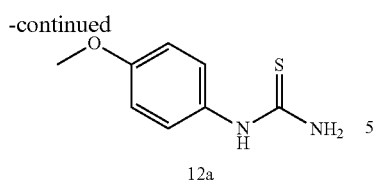
12a

Step-4: Preparation of the S-Methyl Isothiourea Hydroiodide Salt 6a

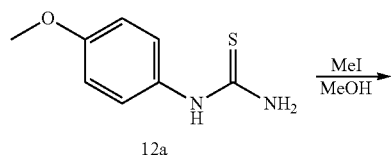
12a

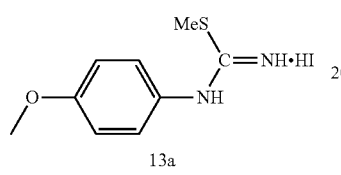
13a

Step-5: Preparation of the Scaffold 183

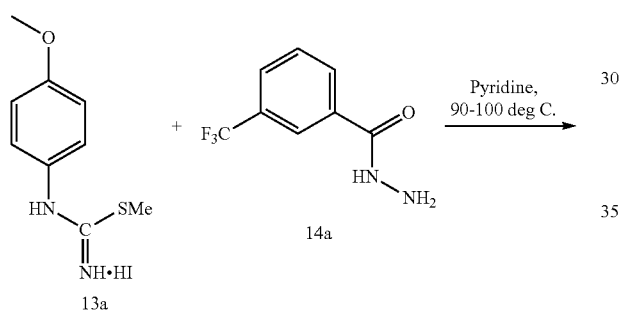

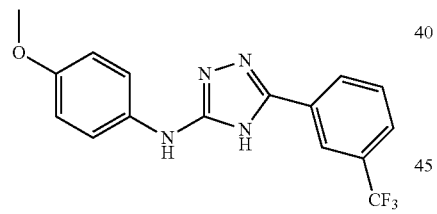
183

(II) Preparation of the Scaffold K36

Step-4: Preparation of the S-Methyl Isothiourea Hydroiodide Salt 13a

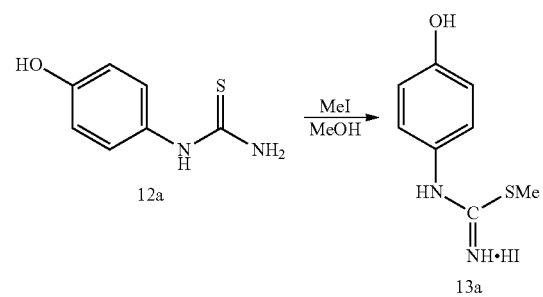
12a  13a

Step-5: Preparation of the Scaffold 181

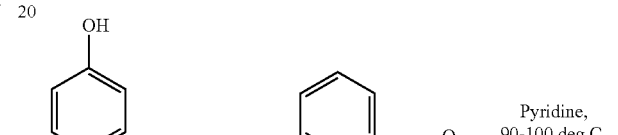

13b  14a

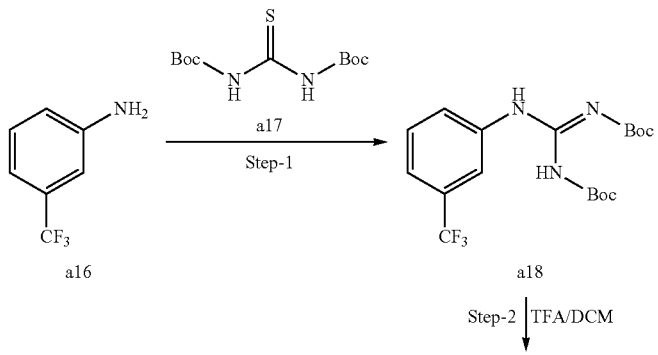
181

Example 4

Synthesis of the 2-amino Imidazole Cores

Synthesis of the 2-amino imidazole cores was carried out as shown in the scheme below. Detailed experimental procedures and analytical data follow.

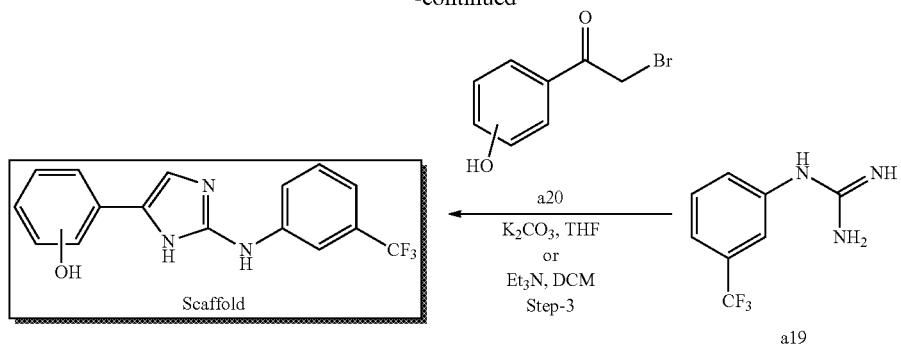

Experimental Procedures for the Synthesis of the 2-amino Imidazole Core

Step-1: Preparation of the Di-Boc Guanidine

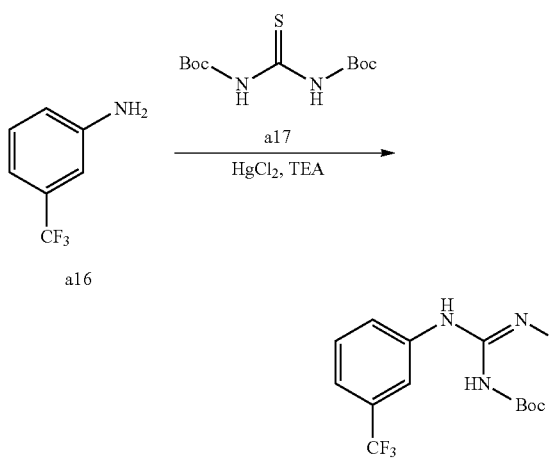

| S. No. | Chemical | Mol. Wt. | Amount | mmol | Molar Ratio |
|---|---|---|---|---|---|
| 1 | 3-Trifluoro methyl aniline | 161 | 81 mg | 0.5 | 1 |
| 2 | Bis Boc thiourea | 276 | 138 mg | 0.5 | 1 |
| 3 | Mercury(II) Chloride | 270 | 150 mg | 0.55 | 1.1 |
| 4 | TEA | 101 | 152 mg | 1.5 | 3 |
| 5 | DCM |  | 5 mL |  |  |

To a suspension of 3-trifluoromethyl aniline (81 mg, 0.5 mmol), bis boc thiourea (138 mg, 0.5 mmol) and Et$_3$N (152 mg, 1.5 mmol) in DCM was added mercury(II) chloride (150 mg, 055 mmol) at 0° C. The reaction mixture was stirred at 0° C. for 1 h and then allowed to warm to room temperature and stirred overnight. When TLC (mobile phase-40% ethyl acetate in n-Hexane Rf. S.M.-0.3, product-0.5) shows formation of product with some starting material unreacted, the reaction mixture was diluted with ethyl acetate and the inorganic by-product was filtered off. The organic layer was washed with water (2×25 mL) followed by brine (1×25 mL). The organic layer was dried over Na$_2$SO$_4$ and concentrated in vacuo to yield the product (200 mg).
Yield: 89.39%
HPLC Purity: 95.38%
1H NMR: Consistent with structure Step-2: Preparation of 1-(3-(trifluoromethyl)phenyl) guanidine

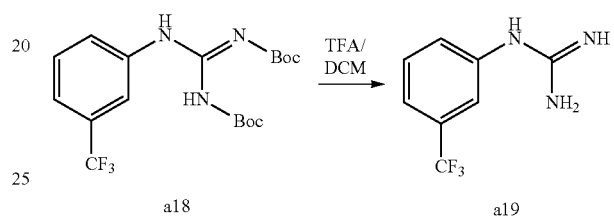

| S. No. | Chemical | Mol. Wt. | Amount | mmol | Molar Ratio |
|---|---|---|---|---|---|
| 1 | Compound-a18 | 403 | 806 mg | 2 | 1 |
| 2 | TFA | 114 | 2.28 g | 20 | 10 |
| 3 | DCM |  | 10 mL |  |  |

To a suspension of compound a18 (806 mg, 2 mmol) in DCM (10 mL) was added TFA (2.28 g, 20 mmol) and the reaction mixture was stirred at room temperature overnight. TLC (mobile phase-40% ethyl acetate in n-Hexane Rf. S.M.-0.6, product-0.2) showed absence of starting material and formation of product. Water was added to the reaction mixture and stirred for 15-20 min. The aqueous layer was separated and basified with 10% NaHCO$_3$ solution to pH ~10. The free base product was extracted with ethyl acetate; the combined organic layer was dried over Na$_2$SO$_4$ and concentrated in vacuo to yield the product (350 mg).
Yield: 72.4%
HPLC Purity: 84.04%
1H NMR: Consistent with structure
LCMS: MH+: 338 (Mol. Wt 337)

Step-3: Preparation of 2-Amino Imidazole Scaffold K38

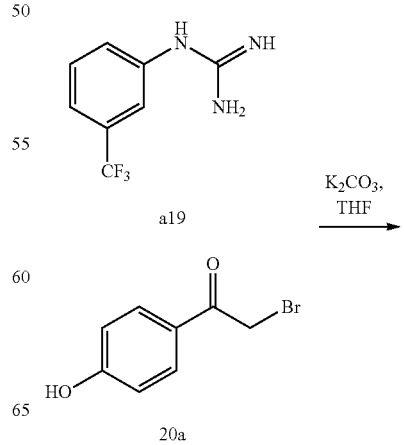

-continued

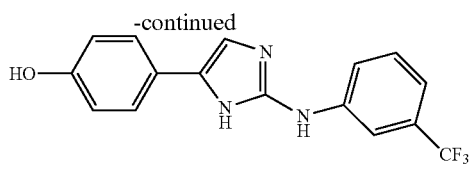

K38

| S. No. | Chemical | Mol. Wt. | Amount | mmol | Molar Ratio |
|---|---|---|---|---|---|
| 1 | 1-(3-(trifluoromethyl) phenyl) guanidine | 203 | 456 mg | 2.25 | 1.5 |
| 2 | 2-bromo-1-(4-hydroxyphenyl)ethanone | 215 | 323 mg | 1.5 | 1 |
| 3 | $K_2CO_3$ | 138 | 249 mg | 1.8 | 1.2 |
| 4 | THF | | 20 mL | | |

To a solution of 1-(3-(trifluoromethyl)phenyl) guanidine (456 mg, 2.25 mmol) in THF (10 mL) was added $K_2CO_3$ (249 mg, 1.18 mmol) followed by 2-bromo-1-(4-hydroxyphenyl)ethanone (323 mg, 1.5 mmol) at 0° C. The reaction mixture was allowed to warm to room temperature and stirred overnight. LCMS and TLC (mobile phase: 10% methanol in chloroform, Rf. S.M.-0.20, product-0.35) formation of product and absence of starting material. The crude product after aqueous workup was purified by preparative HPLC to afford 120 mg of the scaffold K38.

Yield: 25%
HPLC Purity: 90.6%
1H NMR: Consistent with structure
LCMS: MH+: 338 (Mol. Wt 337)

Example 5

Synthesis of the Exemplary Mercapto Library Compound 119

Synthesis of the mercapto core was carried out as shown in the scheme below. Detailed experimental procedures and analytical data follow.

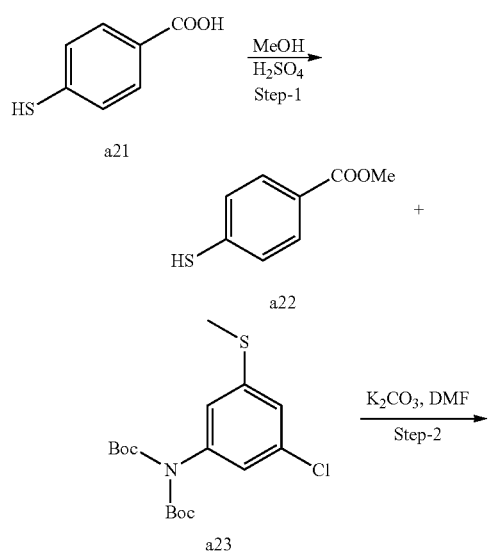

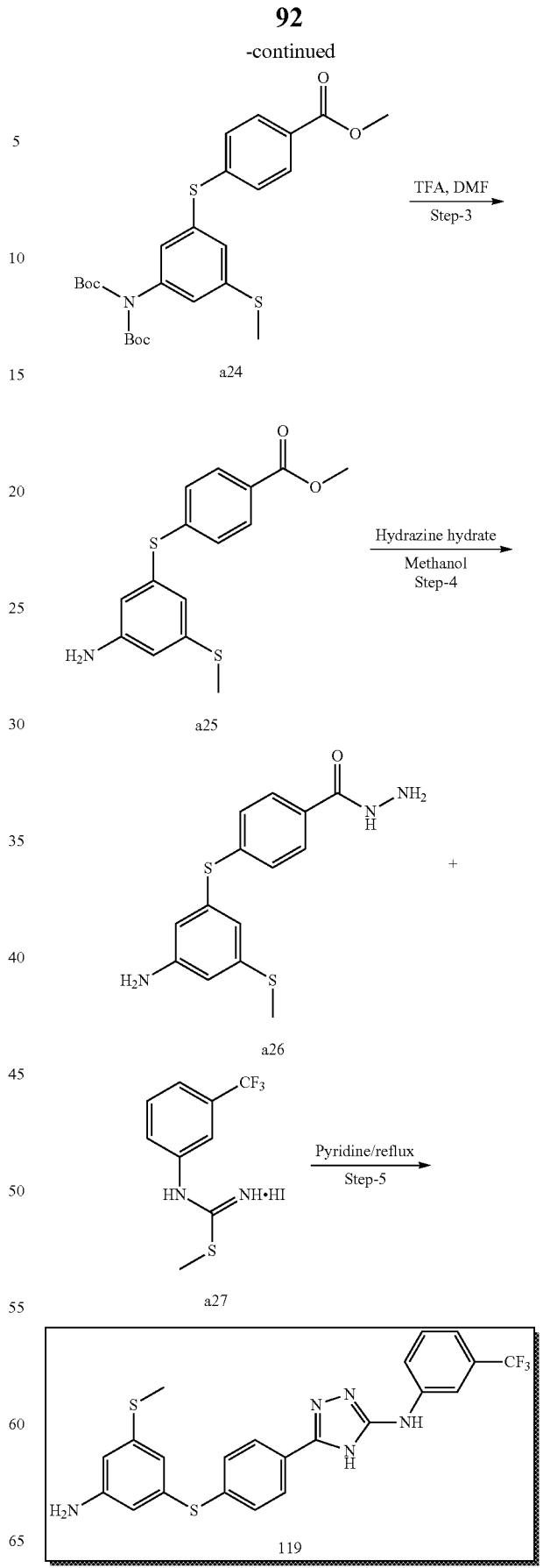

Experimental Procedures for the Synthesis of Compound 119

Step-1: Preparation of Methyl 4-mercaptobenzoate

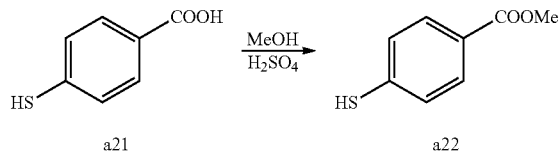

| S. No. | Chemical | Mol. Wt. | Amount | mmol | Molar Ratio |
|---|---|---|---|---|---|
| 1 | 4-mercapto benzoic acid | 154 | 5 g | 32.4 | 1 |
| 2 | $H_2SO_4$ | | Cat. | | |
| 3 | Methanol | | 25 mL | | |

To a solution of 4-mercapto benzoic acid (5 g, 32.4 mmol) in methanol (25 mL) was added catalytic $H_2SO_4$ (1-2 drops) and refluxed for 5-6 h. TLC (mobile phase-10% methanol in chloroform Rf. S.M.-0.2, product-0.6) shows absence of starting material and formation of product; the methanol was distilled off in vacuo and the residue was diluted with ethyl acetate. The organic layer was washed with water (2×25 mL) followed by 10% aq. sodium bicarbonate solution. The organic layer was dried over $Na_2SO_4$ and concentrated in vacuo to obtained the product as an off-white solid (Yield-5 g).

Yield: 97.7%

HPLC Purity: 97.08%

1H NMR: Consistent with structure

LCMS: MH+: 169 (Mol. Wt.168)

Step-2: Coupling Reaction of the Mercapto Benzoate and Di-Boc Chlorovariant

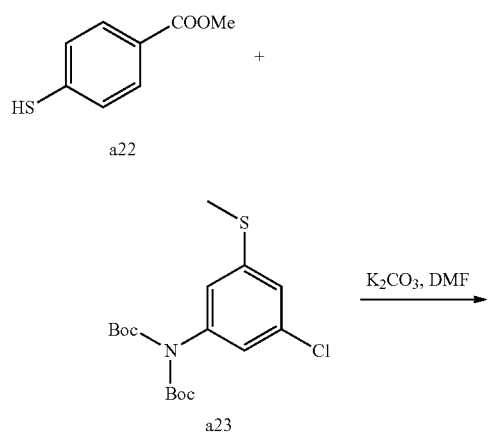

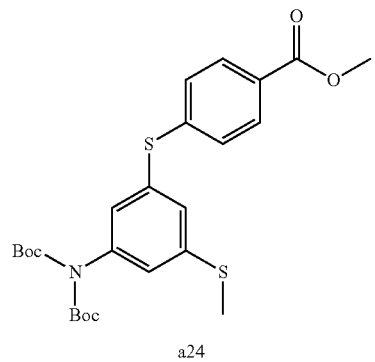

| S. No. | Chemical | Mol. Wt. | Amount | mmol | Molar Ratio |
|---|---|---|---|---|---|
| 1 | Methyl 4-mercapto benzoate | 168 | 500 mg | 2.97 | 1 |
| 2 | Di-Boc chlorovariant a23 | 375 | 1.35 g | 3.57 | 1.2 |
| 3 | $K_2CO_3$ | 138 | 500 mg | 3.57 | 1.2 |
| 4 | DMF | | 10 mL | | |

To a stirred solution of the di-Boc chloro derivative a23 (1.35 g, 3.57 mmol) in DMF (10 mL) was added $K_2CO_3$ (500 mg, 3.57 mmol) and methyl 4-mercaptobenzoate (500 mg, 2.97 mmol) at room temperature. The reaction mass was stirred at room temperature for 2-3 h. TLC (mobile phase-40% ethyl acetate in n-hexane Rf. S.M.-0.5, product-0.4) and LCMS showed formation of product and absence of starting material. The reaction mixture was diluted with ethyl acetate (25 mL) and washed with water (3×30 mL) followed by brine. The organic layer was dried over $Na_2SO_4$ and concentrated in vacuo to afford the desired product (900 mg).

Yield: 60%

HPLC Purity: 92%

LCMS: MH+: 308 (Mol. Wt.507). Boc deprotected mass

Step-3: Preparation of methyl 4-(3-amino-5-(methylthio)phenylthio)benzoate

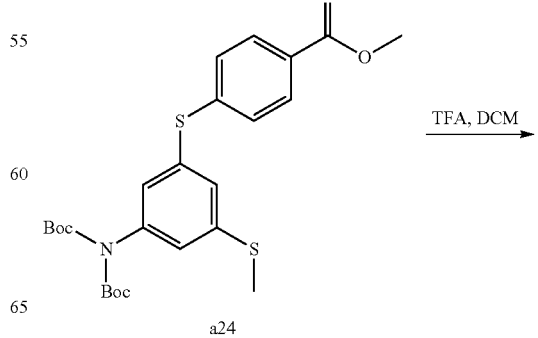

-continued

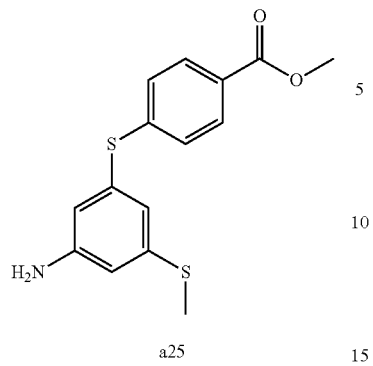

a25

| S. No. | Chemical | Mol. Wt. | Amount | mmol | Molar Ratio |
|---|---|---|---|---|---|
| 1 | Compound a24 | 507 | 270 mg | 0.53 | 1 |
| 2 | Trifluoro acetic acid | 114 | 364 mg | 3.2 | 6 |
| 3 | DCM | | 10 mL | | |

To a stirred solution of compound a24 (287 mg, 0.53 mmol) in DCM (10 mL) was added trifluoroacetic acid (364 mg, 3.2 mmol) at 5-10° C. The reaction mass was stirred at room temperature overnight. TLC (mobile phase-10% methanol in chloroform Rf. S.M.-0.5, product-0.2) and LCMS showed formation of product and absence of starting material. Water was added to the reaction mixture and stirred for 15-20 min. The aqueous layer was separated and basified with 10% NaHCO$_3$ solution to pH ~10. The free base product was extracted with ethyl acetate; the combined organic layer was dried over Na$_2$SO$_4$ and concentrated in vacuo to yield the product (350 mg).

Yield: 73.6%

LCMS Purity: 97.89%

LCMS: MH+: 308 (Mol. Wt.307)

Step-4: Preparation of 4-(3-amino-5-(methylthio)phenyl-thio)benzohydrazide

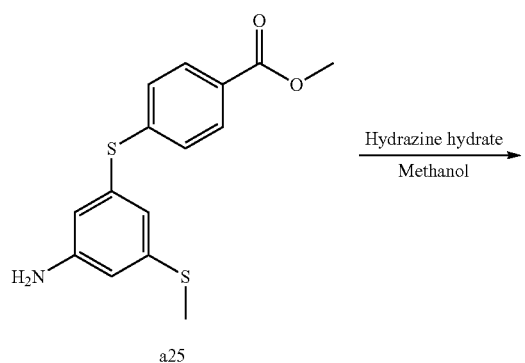

-continued

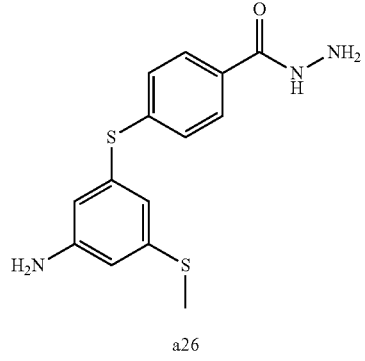

a26

| S. No. | Chemical | Mol. Wt. | Amount | mmol | Molar Ratio |
|---|---|---|---|---|---|
| 1 | Compound-a25 | 307 | 250 mg | 0.81 | 1 |
| 2 | Hydrazine hydrate | 50 | 325 mg | 6.5 | 8 |
| 3 | Methanol | | 10 mL | | |

To a stirred solution of compound a25 (250 mg, 0.81 mmol) in methanol (10 mL) was added hydrazine hydrate (325 mg, 6.5 mmol) at room temperature. The reaction mixture was refluxed for 5-6 h. TLC (mobile phase-10% methanol in chloroform Rf. S.M.-0.5, product-0.2) and LCMS shows formation of product and absence of starting material. The reaction mixture was cooled to room temperature and methanol was distilled off in vacuo to get the crude product. This was stirred in n-hexane:acetone (95:05) and the solid that precipitated out was filtered to get the product (210 mg).

Yield: 84%

HPLC Purity: 91.3%

LCMS: MH+: 308 (Mol. Wt.307)

Step-5: Preparation of the Target Molecule 119

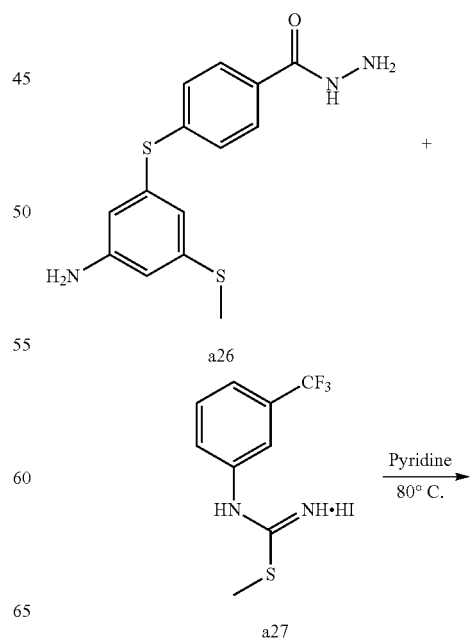

a26 a27

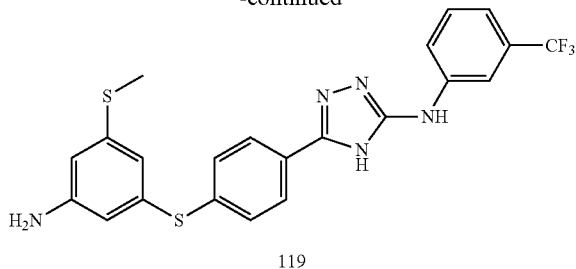

119

| S. No. | Chemical | Mol. Wt. | Amount | mmol | Molar Ratio |
|---|---|---|---|---|---|
| 1 | Compound a26 | 307 | 100 mg | 0.32 | 1 |
| 2 | Compound a27 | 362 | 129 mg | 0.36 | 1.1 |
| 3 | Pyridine | | 5 mL | | |

A solution of compound a26 (100 mg, 032 mmol), compound a27 (129 mg, 0.36 mmol) in pyridine (5 mL) was stirred at 80° C. for 6-7 h. TLC (mobile phase-10% methanol in chloroform Rf. S.M.-0.2, product-0.3) and LCMS showed formation of product and absence of starting material. The reaction mixture was cooled to room temperature. Pyridine was distilled off in-vacuo and the crude residue obtained was purified by preparative HPLC to furnish the pure mercapto library compound 119 (60 mg).
Yield: 38.96%
HPLC Purity: 98.71%
1H NMR: Consistent with structure
LCMS: MH+: 308 (Mol. Wt.307)

Example 6

Library Preparation

Methods of Generation
(A) Compounds Generated by Coupling Reaction of Core and Halovariant:

Most of the targets were generated by coupling of the scaffolds with various chlorovariants. The methods used for the coupling reaction have been described in brief below.

Coupling was attempted with over 50 halovariants including pyridine/pyrimidine/quinoline/isoquinoline derivatives. The reaction scheme and the general experimental procedures have been described below.

General Procedure for the Coupling Reaction of Halovariants with K1/K2

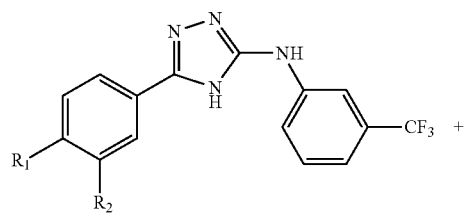

K1: $R_1$ = OH, $R_2$ = H
K2: $R_1$ = H; $R_2$ = OH

HetArCl $\xrightarrow{i/ii/iii}$

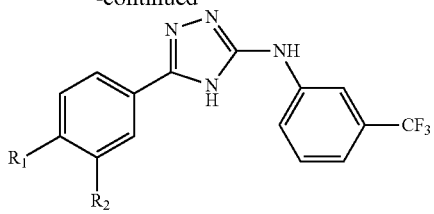

K1: $R_1$ = OHetAr, $R_2$ = H
K2: $R_1$ = H; $R_2$ = OHetAr

Key: (i) $Cs_2CO_3$, DMF, 110° C., overnight; (i) $Cs_2CO_3$, THF, 65°C., overnight; (i) $Cs_2CO_3$, DMF, MW, 200/240° C., 20-30 min.

Method A1 (Conditions (i)):
To a mixture of the scaffold (K1/K2, 160 mg, 0.5 mmol), the halovariant (1.2 equiv., 0.6 mmol) and $Cs_2CO_3$ (196 mg, 0.6 mmol) was added DMF (0.3 mL) and the reaction mixture was heated at 110° C. overnight. $H_2O$ (10 mL) was then added to the reaction mixture and extracted with EtOAc (4×20 mL). The combined organic layer was washed with water & brine and dried over $Na_2SO_4$. Removal of the solvent under reduced pressure yielded a residue which was purified by preparative HPLC to afford the pure product.
Yield & Purity: As mentioned in the Table below.
Method A2 (Conditions (ii)):
To a mixture of the scaffold (K1/K2, 160 mg, 0.5 mmol), the halovariant (1.2 equiv., 0.6 mmol) and $Cs_2CO_3$ (196 mg, 0.6 mmol) was added THF (0.3 mL) and the reaction mixture was heated at 65° C. overnight. $H_2O$ (10 mL) was then added to the reaction mixture and extracted with EtOAc (4×20 mL). The combined organic layer was washed with water & brine and dried over $Na_2SO_4$. Removal of the solvent under reduced pressure yielded a residue which was purified by preparative HPLC to afford the pure product.
Yield & Purity: As mentioned in the Table.
Method A3 (Conditions (iii)):
To a mixture of the scaffold (K1/K2, 160 mg, 0.5 mmol), the halovariant (1.2 equiv., 0.6 mmol) and $Cs_2CO_3$ (196 mg, 0.6 mmol) was added DMF (2 mL) and the reaction mixture was heated at 200/240° C. under microwave conditions for 20-30 min. $H_2O$ (10 mL) was then added to the reaction mixture and extracted with EtOAc (4×20 mL). The combined organic layer was washed with water & brine and dried over $Na_2SO_4$. Removal of the solvent under reduced pressure yielded a residue which was purified by preparative HPLC to afford the pure product.
Yield & Purity: As mentioned in the Table.
(B) Compounds generated from the hydrazide intermediate H3: Some of the compounds were prepared from the hydrazide intermediate (H3, structure shown below). These have been indicated as "hydrazide route" under the "method of synthesis" column in the table. A general scheme for the synthesis of these compounds is also depicted.

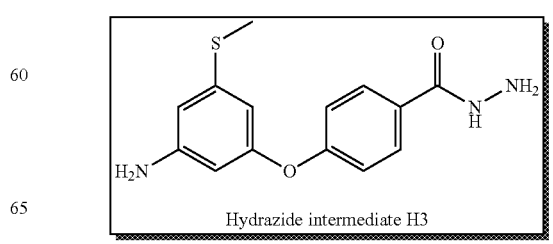

Hydrazide intermediate H3

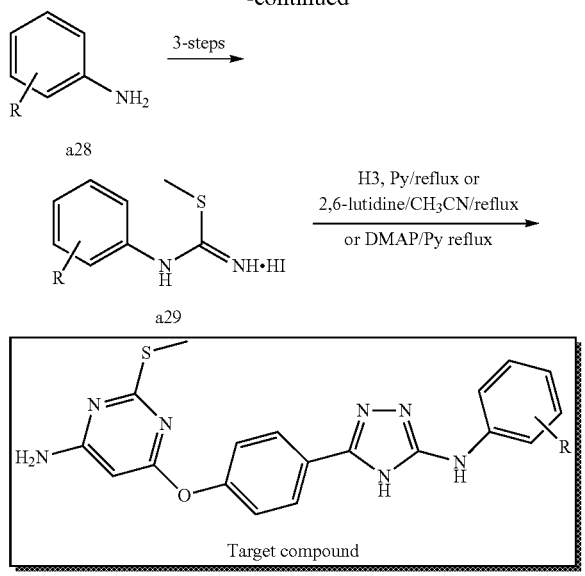

The experimental procedures for the synthesis of the S-methyl isothiourea hydroiodide a29 (3-steps from a28 via the corresponding isothiocyanate and thiourea) and for the preparation of the library compound (cyclization reaction involving compound a29 and the hydrazide intermediate H3) are the same as described earlier in the synthesis of the cores.

(C) Compounds Generated by Displacement Reaction on a 2-pyrimidinyl (Sulfoxide or Sulfone Displacement)

mmol) at room temperature and the reaction mixture was heated at 80° C. for 3-4 h. TLC (mobile phase-10% MeOH in CHCl$_3$) showed absence of starting material and formation of a new spot. The reaction mixture was cooled to room temperature and water was added and extracted with ethyl acetate; the organic layer was washed with brine, dried over Na$_2$SO$_4$ and concentrated in vacuo to obtain the crude product which was purified by preparative HPLC (qty.: 40 mg).

Yield: 25%
HPLC Purity: 99.6%
1H NMR: Consistent with structure
LCMS: MH+: 532 (Mol. Wt 531)

Example 7

Cell Viability Assays

MTT Assay

MTT assay is used to determine cell proliferation, percent of viable cells, and cytotoxicity. MTT (3-[4,5-dimethylthiazol-2-yl]2,5-diphenyltetrazolium bromide) is a yellow dye, which can be absorbed by the living cells and be reduced to purplish blue formazan crystals by succinate tetrazolium reductase in mitochondria. Formazan formation can therefore be used to assess and determine the survival rate of cells.

Tumor cells (A549) were plated at 2500 cells/well of a 96-well plate in complete growth medium (DMEM+10% FBS, antibiotic/antimycotic, fungizone, L-glutamine, sodium pyruvate, and non-essential amino acids). The cells were allowed to grow overnight. After cell proliferation, the cells were washed and re-suspended in fresh culture medium and placed in 96 well plates.

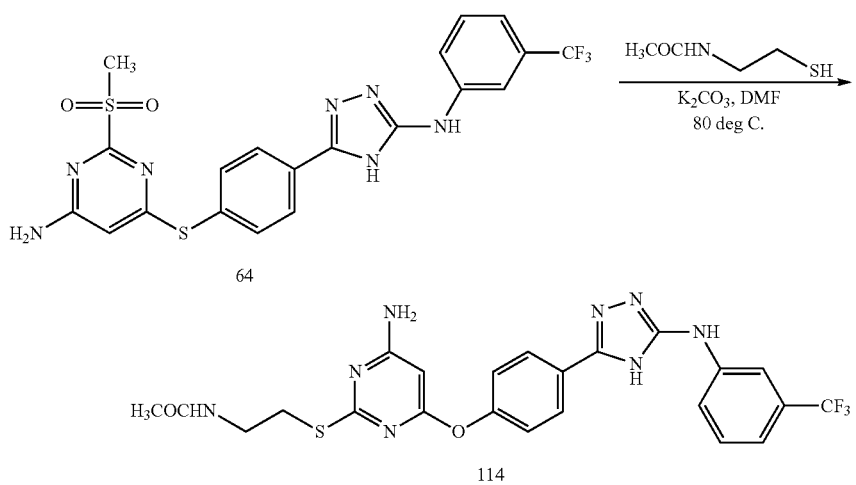

| S. No. | Chemical | Mol. Wt. | Amount | mmol | Molar Ratio |
|---|---|---|---|---|---|
| 1 | Compound 64 | 491 | 150 mg | 0.31 | 1 |
| 2 | N-(2-mercaptoethyl)acetamide | 119 | 54.5 mg | 0.46 | 1.5 |
| 3 | K$_2$CO$_3$ | 138 | 51.3 mg | 0.37 | 1.2 |
| 4 | DMF | | 2.5 mL | | |

To a stirred solution of compound 64 (150 mg, 0.31 mmol) in DMF (2.5 mL) was added K$_2$CO$_3$ (51.3 mg, 0.37 mmol) and N-(2-mercaptoethyl)acetamide (54.5 mg, 0.46

To each of the 96 well plates containing A549 and a control, 5, 1, and 0.2 µM of the exemplary compounds 1-200 were add. The 96 well plates were incubated for 48 hours. Cell viability was measured by adding MTT (Sigma) at 5 mg/ml for 4 h to the cells and then removing the medium and resuspending each well in 50 µl DMSO to solubilize the crystals. The 96-well plates were read on a plate-scanning spectrophotometer (BioTek) at an absorbance of 560 nm. The survival rate of cells was calculated based on the measurement of absorption at the 570 nm wavelength by enzyme immunoassay analyzer. The results are shown in the Table 1.

EC50 of in Cell Viability Assays

Tumor cells (A549) were plated at 2500 cells/well of a 96-well plate in complete growth medium (DMEM+10% FBS, antibiotic/antimycotic, fungizone, L-glutamine, sodium pyruvate, and non-essential amino acids). The cells were allowed to grow overnight and then serial dilutions of the exemplary compounds 254-274 in DMSO were added to fresh complete growth medium and added to the cells for 72 h. Cell viability was measured by adding MTT (Sigma) at 5 mg/ml for 4 h to the cells and then removing the medium and resuspending each well in 50 µl DMSO to solubilize the crystals. The 96-well plates were read on a plate-scanning spectrophotometer (BioTek) at an absorbance of 560 nm. The 11 pt cell viability curves were plotted using GraphPad software and EC50s were calculated using the software and the non-linear regression feature. The results are shown in the Table 1 below.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 1

Exemplary invention compounds and the illustrative results of cell viability on A549 cells

| Compound | Structure | Formula Mol.Wt. | Method of synthesis | % Purity (HPLC) | 5 µM | 1 µM | 0.2 µM |
|---|---|---|---|---|---|---|---|
| | | | | | \% Viability A549 +: <50% ++: 50-70% +++: >70% | | |
| 1. | | C19H14F3N7O 413.36 | A1 | 99.30 | ++ | ++ | +++ |
| 2. | | C19H14F3N7O 413.36 | A1 | 99.97 | +++ | +++ | +++ |
| 3. | | C20H14F3N5O 397.35 | A3 | 98.60 | + | ++ | +++ |
| 4. | | C20H15F3N6O 412.37 | A3 | 96.71 | ++ | +++ | +++ |

TABLE 1-continued

Exemplary invention compounds and the illustrative results of cell viability on A549 cells

| | Structure | Formula / MW | Group | % | | | |
|---|---|---|---|---|---|---|---|
| 5. | | C20H13ClF3N5O 431.80 | A3 | 97.85 | +++ | +++ | +++ |
| 6. | | C20H13ClF3N5O 431.80 | A3 | 99.34 | + | ++ | +++ |
| 7. | | C20H15F3N6O3S 476.43 | A3 | 94.56 | +++ | +++ | +++ |
| 8. | | C21H13F6N5O 465.35 | A3 | 98.72 | ++ | +++ | +++ |
| 9. | | C22H16F3N7OS 483.47 | A1 | 99.32 | +++ | +++ | +++ |

TABLE 1-continued

Exemplary invention compounds and the illustrative results of cell viability on A549 cells

| | | | | | | | |
|---|---|---|---|---|---|---|---|
| 10. | [structure] | C21H14F3N7O 437.38 | A3 | 99.75 | ++ | +++ | +++ |
| 11. | [structure] | C25H18F3N5O2 477.44 | A1 | 97.05 | ++ | +++ | +++ |
| 12. | [structure] | C24H16F3N5O 447.41 | A3 | 97.85 | ++ | +++ | +++ |
| 13. | [structure] | C19H15F3N8O 428.37 | A3 | 99.60 | ++ | +++ | +++ |
| 14. | [structure] | C20H16F3N7OS 459.50 | A3 | 94.62 | ++ | ++ | ++ |

TABLE 1-continued

Exemplary invention compounds and the illustrative results of cell viability on A549 cells

| # | Structure | Formula / MW | Method | % | | | | |
|---|---|---|---|---|---|---|---|---|
| 15. | (3-CF3-phenyl)NH-triazole-phenyl-O-pyrimidin-2-amine | C19H14F3N7O 413.36 | A1 | 99.18 | +++ | +++ | +++ | +++ |
| 16. | (3-CF3-phenyl)NH-triazole-phenyl-O-pyrazin-2-amine | C19H14F3N7O 413.36 | A1 | 99.60 | +++ | +++ | +++ | +++ |
| 17. | (3-CF3-phenyl)NH-triazole-phenyl-O-pyridine | C20H14F3N5O 397.35 | A3 | 99.56 | ++ | ++ | +++ | +++ |
| 18. | (3-CF3-phenyl)NH-triazole-phenyl-O-(2-aminopyridine) | C20H15F3N6O 412.37 | A3 | 98.37 | + | + | ++ | ++ |
| 19. | (3-CF3-phenyl)NH-triazole-(SO2NH2-phenyl)-O-pyridine | C20H15F3N6O3S 476.43 | A3 | 97.01 | +++ | +++ | +++ | +++ |
| 20. | (3-CF3-phenyl)NH-triazole-phenyl-O-(CF3-pyridine) | C21H13F6N5O 465.35 | A3 | 95.94 | ++ | ++ | +++ | +++ |

TABLE 1-continued

Exemplary invention compounds and the illustrative results of cell viability on A549 cells

| | Structure | Formula / MW | Method | % | | | |
|---|---|---|---|---|---|---|---|
| 21. | | C21H14F3N7O 437.38 | A3 | 99.36 | +++ | +++ | +++ |
| 22. | | C25H18F3N5O2 477.44 | A1 | 96.25 | +++ | +++ | +++ |
| 23. | | C24H16F3N5O 447.41 | A3 | 99.28 | +++ | +++ | +++ |
| 24. | | C19H14F3N7O2 429.36 | A3 | 99.36 | +++ | +++ | +++ |
| 25. | | C20H15F3N6O2S 460.43 | A1 | 99.16 | + | + | + |

TABLE 1-continued

Exemplary invention compounds and the illustrative results of cell viability on A549 cells

| # | Structure | Formula / MW | Class | % | | | |
|---|---|---|---|---|---|---|---|
| 26. | (3-Cl-pyrimidin-2-yloxy-phenyl)-oxadiazole-NH-(3-CF3-phenyl) | C19H11ClF3N5O2 433.77 | A3 | 97.08 | +++ | +++ | +++ |
| 27. | (2-NH2-pyrimidin-4-yloxy-phenyl)-oxadiazole-NH-(3-CF3-phenyl) | C19H13F3N6O2 414.34 | A3 | 96.26 | ++ | +++ | +++ |
| 28. | (2-NH2-pyrimidin-5-yloxy-phenyl)-oxadiazole-NH-(3-CF3-phenyl) | C19H13F3N6O2 414.34 | A1 | 99.85 | +++ | +++ | +++ |
| 29. | (pyridin-4-yloxy-phenyl)-oxadiazole-NH-(3-CF3-phenyl) | C20H13F3N4O2 398.34 | A1 | 96.35 | ++ | +++ | +++ |
| 30. | (6-Cl-pyridin-3-yloxy-phenyl)-oxadiazole-NH-(3-CF3-phenyl) | C20H12ClF3N4O2 432.78 | A3 | 94.72 | ++ | +++ | +++ |

TABLE 1-continued
Exemplary invention compounds and the illustrative results of cell viability on A549 cells
| | Structure | Formula / MW | Group | Viability | | | |
|---|---|---|---|---|---|---|---|
| 31. | 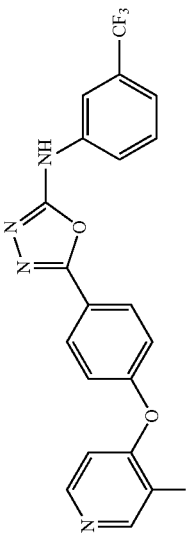 | C20H14F3N5O4S 477.42 | A3 | 99.67 | +++ | +++ | +++ |
| 32. | 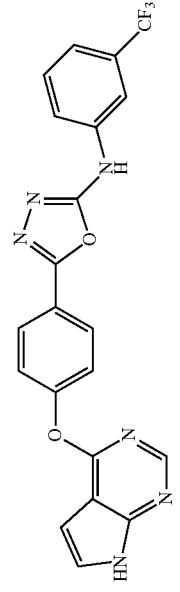 | C21H13F3N6O2 438.36 | A1 | 98.77 | +++ | +++ | +++ |
| 33. | 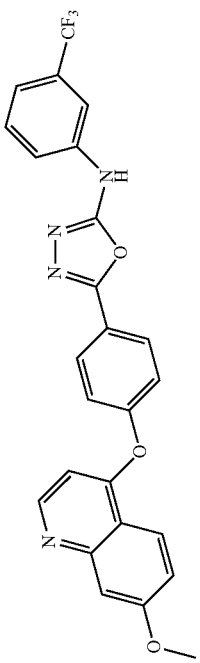 | C25H17F3N4O3 478.42 | A1 | 99.19 | +++ | +++ | +++ |
| 34. | 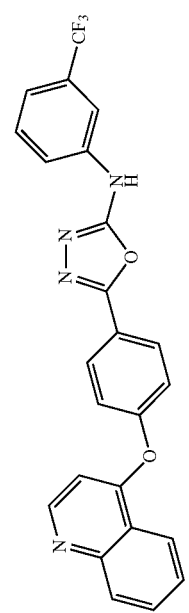 | C24H15F3N4O2 448.40 | A3 | 99.44 | +++ | +++ | +++ |
| 35. | 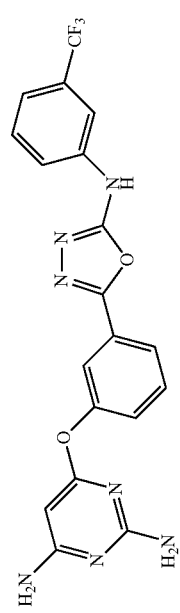 | C19H14F3N7O2 429.36 | A3 | 98.93 | +++ | +++ | +++ |

TABLE 1-continued

Exemplary invention compounds and the illustrative results of cell viability on A549 cells

| | Structure | Formula / MW | Group | Value | | | |
|---|---|---|---|---|---|---|---|
| 36. | (structure with MeS-pyrimidine-NH2, oxadiazole, phenyl-O-phenyl-NH-phenyl-CF3) | C20H15F3N6O2S 460.43 | A3 | 95.31 | +++ | +++ | +++ |
| 37. | (structure with pyridine-O-phenyl, oxadiazole, NH-phenyl-CF3) | C20H13F3N4O2 398.34 | A3 | 97.60 | +++ | +++ | +++ |
| 38. | (structure with H2N-pyridine-O-phenyl, oxadiazole, NH-phenyl-CF3) | C20H14F3N5O2 413.35 | A3 | 90.33 | +++ | +++ | +++ |
| 39. | (structure with SO2NH2-pyridine-O-phenyl, oxadiazole, NH-phenyl-CF3) | C20H14F3N5O4S 477.42 | A1 | 96.26 | +++ | +++ | +++ |
| 40. | (structure with CF3-pyridine-O-phenyl, oxadiazole, NH-phenyl-CF3) | C21H12F6N4O2 466.34 | A3 | 98.90 | +++ | +++ | +++ |

TABLE 1-continued

Exemplary invention compounds and the illustrative results of cell viability on A549 cells

| | Structure | Formula / MW | | | | | |
|---|---|---|---|---|---|---|---|
| 41. | (quinoline-7-methoxy-4-oxy-phenyl-oxadiazole-NH-phenyl-CF₃) | C25H17F3N4O3  478.42 | A1 | 99.70 | +++ | +++ | +++ |
| 42. | (quinoline-4-oxy-phenyl-oxadiazole-NH-phenyl-CF₃) | C24H15F3N4O2  448.40 | A3 | 94.78 | +++ | +++ | +++ |
| 43. | (2-amino-pyrimidine-oxy-phenyl-thiadiazole-NH-phenyl-CF₃) | C19H14F3N7OS  445.42 | A1 | 97.22 | +++ | +++ | +++ |
| 44. | (2-SMe-pyrimidine-amino-oxy-phenyl-thiadiazole-NH-phenyl-CF₃) | C20H15F3N6OS2  476.50 | A1 | 99.95 | +++ | +++ | +++ |
| 45. | (pyrrolopyrimidine-oxy-phenyl-thiadiazole-NH-phenyl-CF₃) | C21H13F3N6OS  454.43 | A1 | 98.64 | + | ++ | +++ |

TABLE 1-continued

Exemplary invention compounds and the illustrative results of cell viability on A549 cells

| 46. | [structure] | C25H17F3N4O2S 494.49 | A1 | 99.55 | + | +++ | +++ |
| 47. | [structure] | C24H15F3N4OS 464.46 | A1 | 97.69 | +++ | +++ | +++ |
| 48. | [structure] | C20H15F3N6OS2 476.50 | A1 | 98.46 | +++ | +++ | +++ |
| 49. | [structure] | C25H17F3N4O2S 494.49 | A1 | 98.72 | ++ | +++ | +++ |

TABLE 1-continued

Exemplary invention compounds and the illustrative results of cell viability on A549 cells

| | Structure | Formula / MW | Method | % | | | |
|---|---|---|---|---|---|---|---|
| 50. | | C24H15F3N4OS 464.46 | A3 | 98.97 | | | |
| 51. | | C20H15F3N6O 412.37 | A1 | 96.16 | + | ++ | +++ |
| 52. | | C21H18F3N7O2 457.41 | A1 | 94.44 | +++ | +++ | +++ |
| 53. | | C22H20F3N7O3 487.43 | A1 | 96.87 | + | +++ | +++ |
| 54. | | C20H16F3N7O 427.38 | A1 | 99.98 | + | + | +++ |

TABLE 1-continued

Exemplary invention compounds and the illustrative results of cell viability on A549 cells

| | Structure | Formula / MW | Method | % | | | |
|---|---|---|---|---|---|---|---|
| 55. | | C20H15F3N6O 412.37 | A1 | 98.35 | + | ++ | ++ |
| 56. | | C22H16F3N7OS 483.47 | A1 | 99.98 | +++ | +++ | +++ |
| 57. | | C21H18F3N7O2 457.41 | A1 | 99.84 | +++ | +++ | +++ |
| 58. | | C22H20F3N7O3 487.43 | A1 | 99.83 | +++ | +++ | +++ |
| 59. | | C20H14F3N5O2 413.35 | A3 | 98.39 | +++ | +++ | +++ |

TABLE 1-continued

Exemplary invention compounds and the illustrative results of cell viability on A549 cells

| | Structure | Formula / MW | | Viability | | | |
|---|---|---|---|---|---|---|---|
| 60. | | C21H13F3N6O2 438.36 | A1 | 99.46 | +++ | +++ | +++ |
| 61. | | C21H19F3N8O2 472.42 | C | 97.15 | +++ | +++ | +++ |
| 62. | | C21H19F3N8OS 488.49 | C | 99.41 | +++ | +++ | +++ |
| 63. | | C20H16F3N7O2S 475.45 | N.A. | 97.98 | ++ | +++ | +++ |
| 64. | | C20H16F3N7O3S 491.45 | N.A. | 94.78 | +++ | +++ | +++ |

TABLE 1-continued

Exemplary invention compounds and the illustrative results of cell viability on A549 cells

| | Structure | Formula / MW | Class | % | | | |
|---|---|---|---|---|---|---|---|
| 65. | | C20H19N7OS<br>405.48 | B | 95.91 | ++ | +++ | +++ |
| 66. | | C20H15ClF3N7OS<br>493.89 | B | 98.77 | + | +++ | +++ |
| 67. | | C21H21N7OS<br>419.50 | B | 90.69 | + | + | ++ |
| 68. | | C22H15F3N6O<br>436.39 | A3 | 96.85 | + | ++ | +++ |
| 69. | | C24H17F3N6O<br>462.43 | A1 | 97.30 | +++ | +++ | +++ |

TABLE 1-continued

Exemplary invention compounds and the illustrative results of cell viability on A549 cells

| | | | | | | | |
|---|---|---|---|---|---|---|---|
| 70. | [structure] | C24H17F3N6O2 478.43 | A1 | 90.14 | + | +++ | +++ |
| 71. | [structure] | C20H15F3N6O2 428.37 | A1 | 96.92 | ++ | +++ | +++ |
| 72. | [structure] | C20H16F3N7O2 443.38 | A1 | 97.47 | + | +++ | +++ |
| 73. | [structure] | C21H16F3N5O2 427.38 | A3 | 91.74 | + | +++ | +++ |
| 74. | [structure] | C21H16F3N5O 411.38 | A1 | 99.51 | + | + | +++ |

TABLE 1-continued

Exemplary invention compounds and the illustrative results of cell viability on A549 cells

| | Structure | Formula / MW | Class | Viability | | | |
|---|---|---|---|---|---|---|---|
| 75. | | C22H16F3N7O2 467.40 | A1 | 98.01 | +++ | +++ | +++ |
| 76. | | C20H15F3N6O2 428.37 | A2 | 99.37 | ++ | +++ | +++ |
| 77. | | C21H18F3N7O 441.41 | A1 | 98.71 | ++ | ++ | +++ |
| 78. | | C22H20F3N7O3 487.43 | C | 98.27 | + | +++ | +++ |
| 79. | | C21H18F3N7O2 457.41 | A1 | 98.21 | + | + | +++ |

TABLE 1-continued

Exemplary invention compounds and the illustrative results of cell viability on A549 cells

| | Structure | Formula / MW | Method | % | | | |
|---|---|---|---|---|---|---|---|
| 80. | 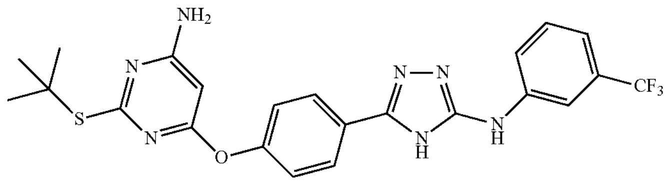 [SMILES: CC(C)(C)Sc1nc(N)cc(Oc2ccc(-c3nnc(Nc4cccc(C(F)(F)F)c4)[nH]3)cc2)n1] | C23H22F3N7OS 501.53 | C | 99.10 | + | ++ | +++ |
| 81. | 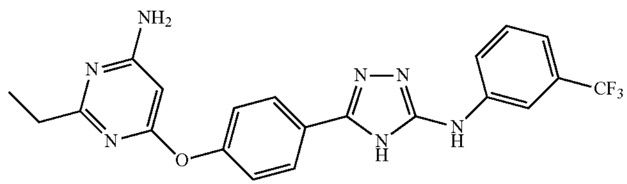 [SMILES: CCc1nc(N)cc(Oc2ccc(-c3nnc(Nc4cccc(C(F)(F)F)c4)[nH]3)cc2)n1] | C21H18F3N7O 441.41 | A1 | 99.61 | + | ++ | +++ |
| 82. | 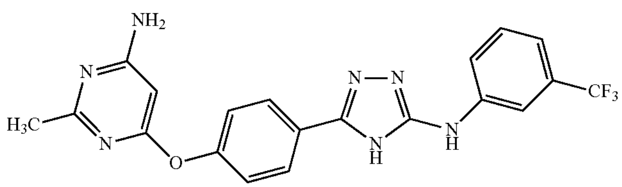 [SMILES: Cc1nc(N)cc(Oc2ccc(-c3nnc(Nc4cccc(C(F)(F)F)c4)[nH]3)cc2)n1] | C20H16F3N7O 427.38 | A1 | 98.21 | ++ | +++ | +++ |
| 83. | 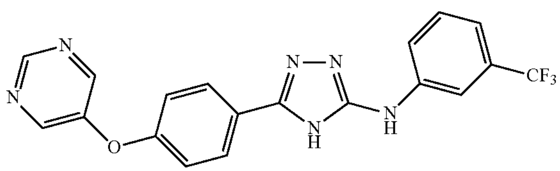 [SMILES: FC(F)(F)c1cccc(Nc2nnc(-c3ccc(Oc4cncnc4)cc3)[nH]2)c1] | C19H13F3N6O 398.34 | A1 | 99.92 | +++ | +++ | +++ |
| 84. | 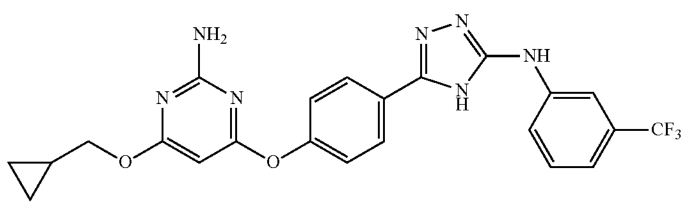 [SMILES: Nc1nc(OCC2CC2)cc(Oc2ccc(-c3nnc(Nc4cccc(C(F)(F)F)c4)[nH]3)cc2)n1] | C23H20F3N7O2 483.45 | A1 | 95.21 | +++ | +++ | +++ |

TABLE 1-continued

Exemplary invention compounds and the illustrative results of cell viability on A549 cells

| | | | | | |
|---|---|---|---|---|---|
| 85. | [structure] | C22H15F3N6O 436.39 | A3 | 87.43 | ++ | +++ | +++ |
| 86. | [structure] | C24H17F3N6O 462.43 | A1 | 91.69 | +++ | +++ | +++ |
| 87. | [structure] | C24H17F3N6O2 478.43 | A1 | 99.18 | +++ | +++ | +++ |
| 88. | [structure] | C20H15F3N6O2 428.37 | A1 | 90.36 | +++ | +++ | +++ |
| 89. | [structure] | C20H16F3N7O2 443.38 | A1 | 91.54 | +++ | +++ | +++ |

TABLE 1-continued

Exemplary invention compounds and the illustrative results of cell viability on A549 cells

| | Structure | Formula / MW | Method | Value | | | |
|---|---|---|---|---|---|---|---|
| 90. | | C21H16F3N5O2 427.38 | A3 | 87.07 | +++ | +++ | +++ |
| 91. | | C21H16F3N5O 411.38 | A1 | 91.16 | ++ | +++ | +++ |
| 92. | | C22H16F3N7O2 467.40 | A1 | 96.78 | +++ | +++ | +++ |
| 93. | | C20H15F3N6O2 428.37 | A1 | 95.56 | ++ | +++ | +++ |
| 94. | | C21H18F3N7O 441.41 | A1 | 72.97 | ++ | +++ | +++ |

TABLE 1-continued

Exemplary invention compounds and the illustrative results of cell viability on A549 cells

| # | Structure | Formula / MW | Method | Value | | | |
|---|---|---|---|---|---|---|---|
| 95. | | C20H16F3N7O 427.38 | A1 | 97.91 | ++ | +++ | +++ |
| 96. | | C22H20F3N7O3 487.43 | A1 | 98.09 | +++ | +++ | +++ |
| 97. | | C21H18F3N7O2 457.41 | A1 | 88.32 | +++ | +++ | +++ |
| 98. | | C23H22F3N7OS 501.53 | A1 | 83.21 | +++ | +++ | +++ |
| 99. | | C21H18F3N7O 441.41 | A1 | 99.90 | ++ | +++ | +++ |

TABLE 1-continued

Exemplary invention compounds and the illustrative results of cell viability on A549 cells

| | Structure | Formula / MW | Class | Value | | | |
|---|---|---|---|---|---|---|---|
| 100. | | C20H16F3N7O 427.38 | A1 | 98.77 | +++ | +++ | +++ |
| 101. | | C19H13F3N6O 398.34 | A1 | 96.59 | +++ | +++ | +++ |
| 102. | | C21H18F3N7OS 473.47 | A1 | 99.40 | +++ | +++ | +++ |
| 103. | | C20H13ClF3N5O 431.80 | A2 | 96.29 | ++ | +++ | +++ |
| 104. | | C20H15ClF3N7OS 493.89 | A1 | 96.81 | + | +++ | +++ |

TABLE 1-continued

Exemplary invention compounds and the illustrative results of cell viability on A549 cells

| | | | | | |
|---|---|---|---|---|---|
| 105. | [structure] | C20H15F4N7OS 477.44 | A1 | 98.56 | + | +++ | +++ |
| 106. | [structure] | C20H15F4N7OS 477.44 | A1 | 96.92 | +++ | +++ | +++ |
| 107. | [structure] | C20H15F4N7OS 477.44 | A1 | 98.38 | ++ | +++ | +++ |
| 108. | [structure] | C21H16F3N5O2 427.38 | A1 | 99.04 | + | +++ | +++ |
| 109. | [structure] | C21H18F3N7O2S 489.47 | A1 | 95.05 | + | +++ | +++ |

TABLE 1-continued
Exemplary invention compounds and the illustrative results of cell viability on A549 cells
| | | | | | | |
|---|---|---|---|---|---|---|
| 110. | 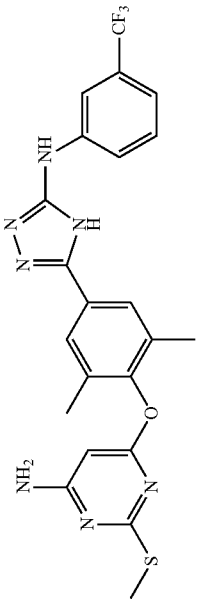 | C22H20F3N7OS 487.50 | A1 | 97.23 | +++ | +++ | +++ |
| 111. | 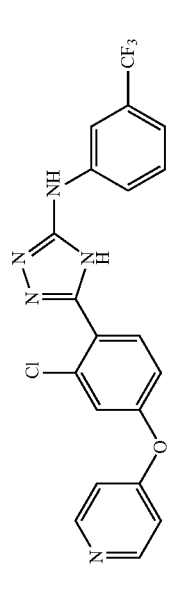 | C20H13ClF3N5O 431.80 | A1 | 98.23 | +++ | +++ | +++ |
| 112. | 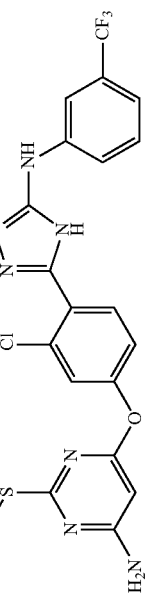 | C20H15ClF3N7OS 493.89 | A1 | 95.02 | +++ | +++ | +++ |
| 113. | 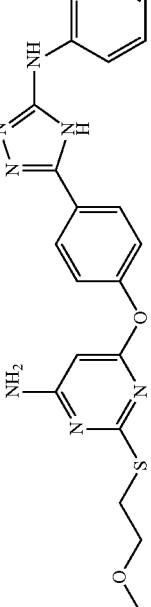 | C24H24F3N7O3S 547.55 | C | 99.94 | 1+++ | +++ | +++ |
| 114. | 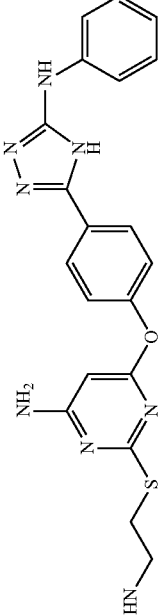 | C23H21F3N8O2S 530.53 | C | 99.58 | +++ | +++ | +++ |

TABLE 1-continued

Exemplary invention compounds and the illustrative results of cell viability on A549 cells

| # | Structure | Formula / MW | | % | | | |
|---|---|---|---|---|---|---|---|
| 115. | 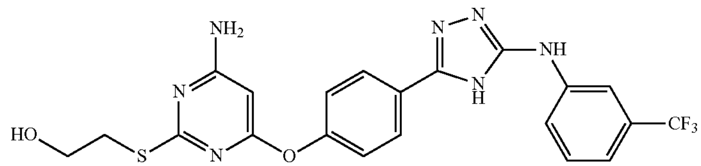 [SMILES: Nc1cc(Oc2ccc(-c3nnc(Nc4cccc(C(F)(F)F)c4)[nH]3)cc2)nc(SCCO)n1] | C21H18F3N7O2S 489.47 | C | 99.73 | +++ | +++ | +++ |
| 116. | 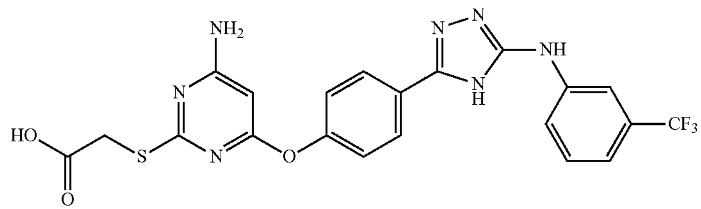 [SMILES: Nc1cc(Oc2ccc(-c3nnc(Nc4cccc(C(F)(F)F)c4)[nH]3)cc2)nc(SCC(=O)O)n1] | C21H16F3N7O3S 503.86 | C | 96.72 | +++ | +++ | +++ |
| 117. | 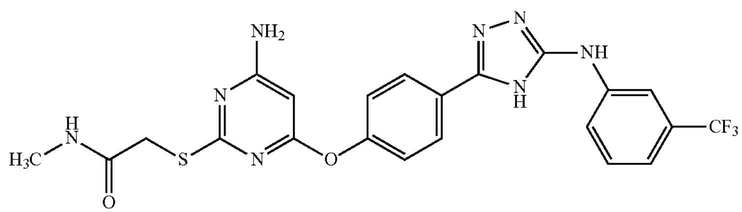 [SMILES: CNC(=O)CSc1nc(N)cc(Oc2ccc(-c3nnc(Nc4cccc(C(F)(F)F)c4)[nH]3)cc2)n1] | C22H19F3N8O2S 516.50 | C | 97.34 | +++ | +++ | +++ |
| 118. | 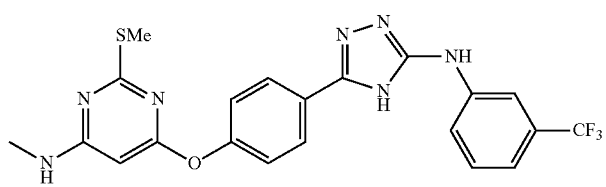 [SMILES: CNc1cc(Oc2ccc(-c3nnc(Nc4cccc(C(F)(F)F)c4)[nH]3)cc2)nc(SC)n1] | C21H18F3N7OS 473.47 | N.A. | 98.43 | +++ | +++ | +++ |
| 119. | 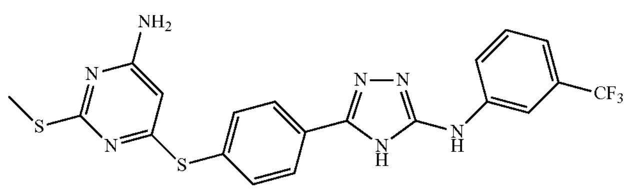 [SMILES: CSc1nc(N)cc(Sc2ccc(-c3nnc(Nc4cccc(C(F)(F)F)c4)[nH]3)cc2)n1] | C20H16F3N7S2 475.51 | N.A. | 98.71 | + | + | +++ |

TABLE 1-continued
Exemplary invention compounds and the illustrative results of cell viability on A549 cells
| | | | | | | |
|---|---|---|---|---|---|---|
| 120. | 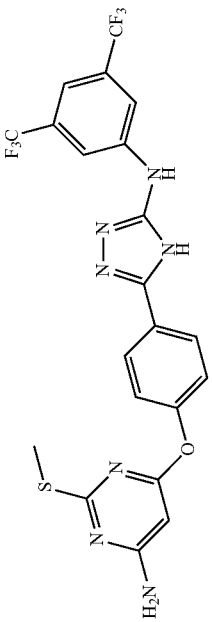 | C21H15F6N7OS 527.45 | B | 93.64 | +++ | +++ | +++ |
| 121. | 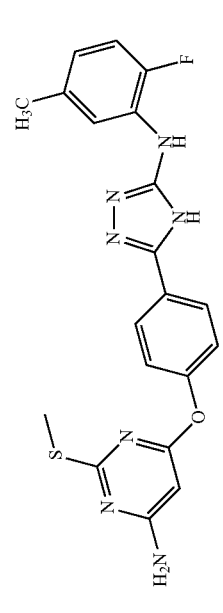 | C20H18FN7OS 423.47 | B | 98.14 | + | ++ | +++ |
| 122. | 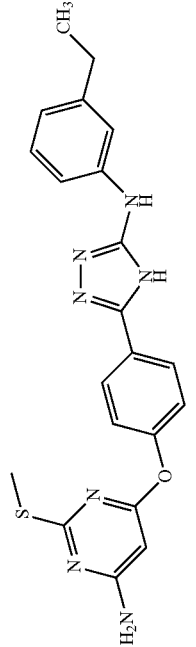 | C21H21N7OS 419.50 | B | 98.90 | + | +++ | +++ |
| 123. | 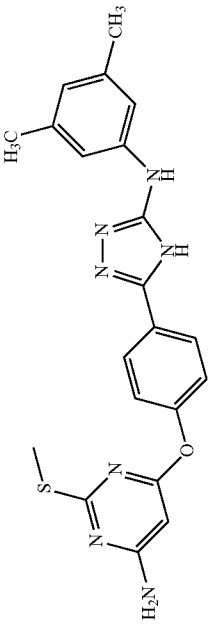 | C21H21N7OS 419.50 | B | 99.38 | + | + | + |
| 124. | 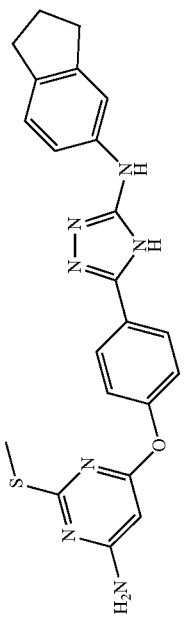 | C22H21N7OS 431.51 | B | 93.66 | + | +++ | +++ |

TABLE 1-continued

Exemplary invention compounds and the illustrative results of cell viability on A549 cells

| | Structure | Formula / MW | Class | Value | | | |
|---|---|---|---|---|---|---|---|
| 125. | 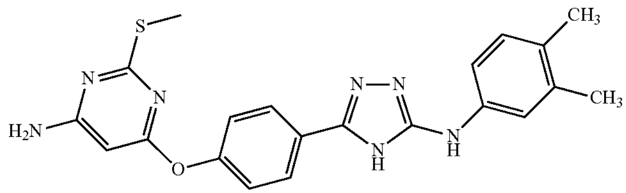 [SMILES: CSc1nc(N)cc(Oc2ccc(-c3nnc(Nc4ccc(C)c(C)c4)[nH]3)cc2)n1] | C21H21N7OS 419.50 | B | 95.94 | + | +++ | +++ |
| 126. | 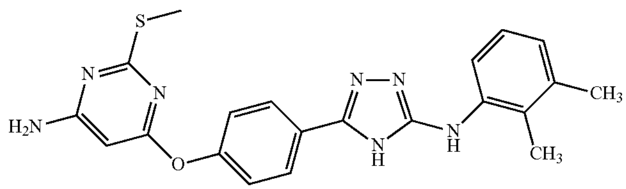 [SMILES: CSc1nc(N)cc(Oc2ccc(-c3nnc(Nc4cccc(C)c4C)[nH]3)cc2)n1] | C21H21N7OS 419.50 | B | 92.44 | + | + | + |
| 127. | 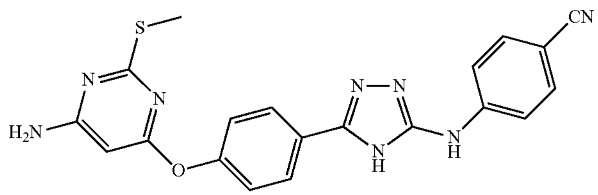 [SMILES: CSc1nc(N)cc(Oc2ccc(-c3nnc(Nc4ccc(C#N)cc4)[nH]3)cc2)n1] | C20H16N8OS 416.46 | B | 94.59 | ++ | +++ | +++ |
| 128. | 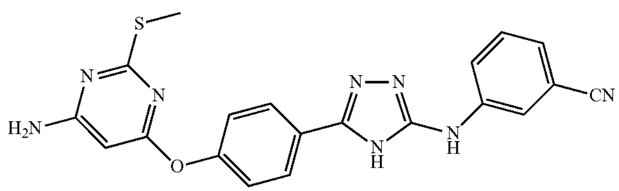 [SMILES: CSc1nc(N)cc(Oc2ccc(-c3nnc(Nc4cccc(C#N)c4)[nH]3)cc2)n1] | C20H16N8OS 416.46 | B | 92.45 | +++ | +++ | +++ |
| 129. | 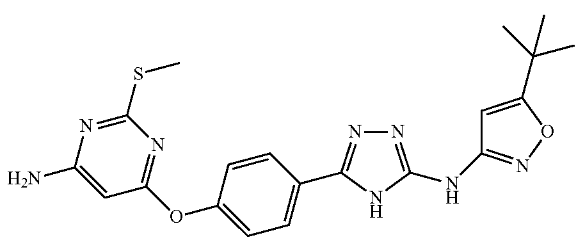 [SMILES: CSc1nc(N)cc(Oc2ccc(-c3nnc(Nc4cc(C(C)(C)C)on4)[nH]3)cc2)n1] | C20H22N8O2S 438.51 | B | 92.68 | +++ | +++ | +++ |

TABLE 1-continued

Exemplary invention compounds and the illustrative results of cell viability on A549 cells

| | | | | | | |
|---|---|---|---|---|---|---|
| 130. | [structure] | C21H18N8OS 430.49 | B | 95.70 | + | +++ | +++ |
| 131. | [structure] | C23H22N8OS 458.54 | B | 98.96 | + | +++ | +++ |
| 132. | [structure] | C20H23N9OS 437.52 | B | 96.36 | + | +++ | +++ |
| 133. | [structure] | C19H16ClN7OS 425.89 | B | 98.27 | + | + | +++ |
| 134. | [structure] | C22H23N7O2S 449.53 | B | 96.06 | + | +++ | +++ |

TABLE 1-continued

Exemplary invention compounds and the illustrative results of cell viability on A549 cells

| # | Structure | Formula / MW | | Viability | | | |
|---|---|---|---|---|---|---|---|
| 135. | (tetrahydronaphthalen-1-ylamino triazole-phenoxy-pyrimidine structure) | C23H23N7OS 445.54 | B | 79.48 | + | + | + |
| 136. | (fluoren-2-ylamino triazole-phenoxy-pyrimidine structure) | C26H21N7OS 479.56 | B | 96.10 | + | ++ | +++ |
| 137. | (2-fluoro-3-trifluoromethylphenylamino triazole-phenoxy-pyrimidine structure) | C20H15F4N7OS 477.44 | B | 99.70 | + | + | +++ |
| 138. | (3-methoxycarbonylphenylamino triazole-phenoxy-pyrimidine structure) | C21H19N7O3S 449.49 | B | 96.82 | + | +++ | +++ |

TABLE 1-continued

Exemplary invention compounds and the illustrative results of cell viability on A549 cells

| | | | | | |
|---|---|---|---|---|---|
| 139. | [structure] | C27H29N9OS 527.64 | B | 93.44 | +++ +++ +++ |
| 140. | [structure] | C19H16ClN7OS 425.89 | B | 99.31 | ++ +++ +++ |
| 141. | [structure] | C23H22F3N7OS 501.53 | A1 | 93.81 | + +++ +++ |
| 142. | [structure] | C20H13D3F3N7O2 446.40 | N.A. | 96.51 | +++ +++ +++ |

TABLE 1-continued

Exemplary invention compounds and the illustrative results of cell viability on A549 cells

| # | Structure | Formula / MW | Method | Viability | | | |
|---|---|---|---|---|---|---|---|
| 143. | | C21H16F3N5O  411.38 | Mitsunobu | 93.87 | +++ | +++ | +++ |
| 144. | | C23H22F3N7OS  501.53 | A1 | 97.01 | ++ | +++ | +++ |
| 145. | | C24H24F3N7O2S  531.55 | A1 | 98.74 | + | +++ | +++ |
| 146. | | C24H16F3N5O  447.41 | A3 | 91.30 | + | +++ | +++ |
| 147. | | C21H13F4N5O3  459.35 | N.A. | 99.29 | ++ | +++ | +++ |

TABLE 1-continued

Exemplary invention compounds and the illustrative results of cell viability on A549 cells

| | | | | | | | |
|---|---|---|---|---|---|---|---|
| 148. | (structure) | C25H15F6N5O 515.41 | A1 | 95.77 | +++ | +++ | +++ |
| 149. | (structure) | C24H16F3N5O 447.41 | A1 | 97.87 | ++ | +++ | +++ |
| 150. | (structure) | C24H15ClF3N5O 481.86 | A1 | 93.88 | +++ | +++ | +++ |
| 151. | (structure) | C23H22F3N7OS 501.53 | A1 | 99.51 | +++ | +++ | +++ |
| 152. | (structure) | C24H17F3N8OS 522.50 | C | 99.03 | +++ | +++ | +++ |

TABLE 1-continued

Exemplary invention compounds and the illustrative results of cell viability on A549 cells

| | | | | | | |
|---|---|---|---|---|---|---|
| 153. | [structure with COOH, triazole, pyrimidine-SMe, NH2] | C20H17N7O3S 435.46 | B | 93.41 | +++ | +++ | +++ |
| 154. | [structure with CH3, triazole, pyrimidine-SMe, NH2] | C20H19N7OS 405.48 | B | 94.63 | + | + | ++ |
| 155. | [structure with cyclohexyl, triazole, pyrimidine-SMe, NH2] | C19H23N7OS 397.50 | B | 77.11 | + | +++ | +++ |
| 156. | [structure with CF3, triazole, NH2, F] | C21H15F4N5O 429.37 | Reduction of K1-99 (Raney Ni) | 98.46 | ++ | +++ | +++ |
| 157. | [structure with CF3, triazole, pyrimidine-CF3, dimethyl] | C22H16F6N6O 494.39 | A1 | 99.90 | +++ | +++ | +++ |

TABLE 1-continued

Exemplary invention compounds and the illustrative results of cell viability on A549 cells

| | Structure | Formula / MW | Class | % | | | |
|---|---|---|---|---|---|---|---|
| 158. | | C25H18F3N5O 461.44 | A1 | 99.68 | ++ | +++ | +++ |
| 159. | | C25H15F6N5O 515.41 | A1 | 99.72 | ++ | +++ | +++ |
| 160. | | C25H19F3N6O3 508.45 | A1 | 89.18 | ++ | +++ | +++ |
| 161. | | C25H18F3N5O2 477.44 | A1 | 70.91 | + | ++ | +++ |

TABLE 1-continued

Exemplary invention compounds and the illustrative results of cell viability on A549 cells

| | Structure | Formula / MW | Class | % | | | |
|---|---|---|---|---|---|---|---|
| 162. | | C25H18F3N5O 461.44 | A1 | 97.14 | +++ | +++ | +++ |
| 163. | | C25H15F6N5O2 531.41 | A1 | 99.14 | +++ | +++ | +++ |
| 164. | | C24H16F3N5O 447.41 | A3 | 93.64 | ++ | +++ | +++ |
| 165. | | C25H15F6N5O 515.41 | A1 | 93.65 | +++ | +++ | +++ |
| 166. | | C24H16F3N5O 447.41 | A1 | 98.49 | +++ | +++ | +++ |

TABLE 1-continued
Exemplary invention compounds and the illustrative results of cell viability on A549 cells
| | | | | | | |
|---|---|---|---|---|---|---|
| 167. | 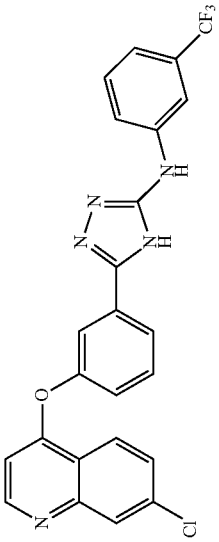 | C24H15ClF3N5O 481.86 | A1 | 89.33 | +++ | +++ | +++ |
| 168. | 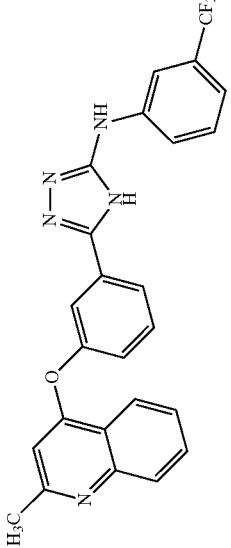 | C25H18F3N5O 461.44 | A1 | 99.56 | ++ | +++ | +++ |
| 169. | 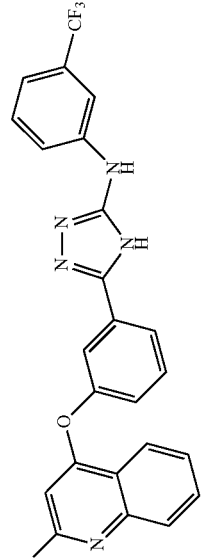 | C25H15F6N5O 515.41 | A1 | 98.88 | +++ | +++ | +++ |
| 170. | 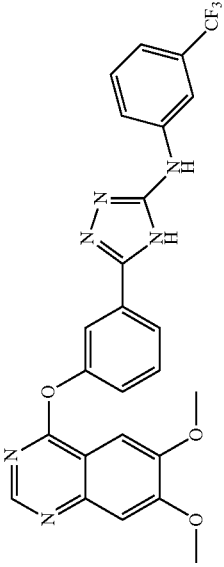 | C25H19F3N6O3 508.45 | A1 | 96.10 | +++ | +++ | +++ |

TABLE 1-continued

Exemplary invention compounds and the illustrative results of cell viability on A549 cells

| | Structure | Formula / MW | Class | Value | | | |
|---|---|---|---|---|---|---|---|
| 171. | 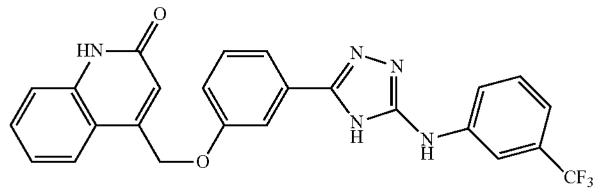 | C25H18F3N5O2 477.44 | A1 | 83.65 | +++ | +++ | +++ |
| 172. | 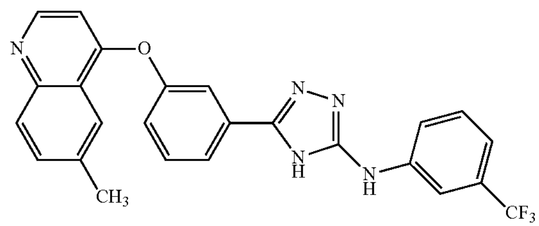 [SMILES: Cc1ccc2nccc(Oc3cccc(-c4nnc(Nc5cccc(C(F)(F)F)c5)[nH]4)c3)c2c1] | C25H18F3N5O 461.44 | A1 | 98.21 | ++ | +++ | +++ |
| 173. | 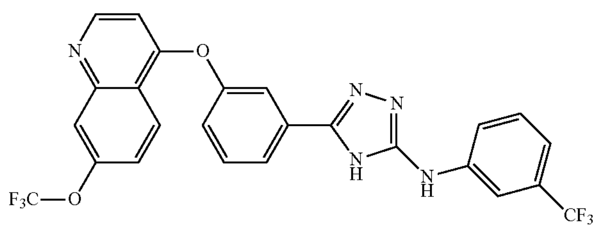 [SMILES: FC(F)(F)Oc1ccc2c(Oc3cccc(-c4nnc(Nc5cccc(C(F)(F)F)c5)[nH]4)c3)ccnc2c1] | C25H15F6N5O2 531.41 | A1 | 95.54 | +++ | +++ | +++ |
| 174. | 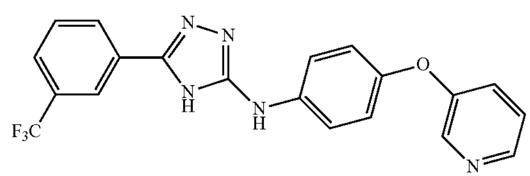 [SMILES: FC(F)(F)c1cccc(-c2nnc(Nc3ccc(Oc4cccnc4)cc3)[nH]2)c1] | C20H14F3N5O 397.35 | A1 | 99.71 | +++ | +++ | +++ |
| 175. | 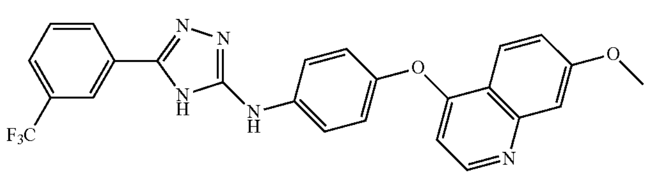 [SMILES: COc1ccc2c(Oc3ccc(Nc4nnc(-c5cccc(C(F)(F)F)c5)[nH]4)cc3)ccnc2c1] | C25H18F3N5O2 477.44 | A1 | 91.69 | +++ | +++ | +++ |

TABLE 1-continued

Exemplary invention compounds and the illustrative results of cell viability on A549 cells

| | | | | | | | |
|---|---|---|---|---|---|---|---|
| 176. | [structure] | C20H16F3N7OS 459.45 | A1 | 97.29 | +++ | +++ | +++ |
| 177. | [structure] | C21H16F3N5O 411.38 | A1 | 99.67 | +++ | +++ | +++ |
| 178. | [structure] | C21H16F3N5O 411.38 | A1 | 99.99 | + | + | ++ |
| 179. | [structure] | C21H18F3N7OS 473.47 | A1 | 95.27 | ++ | +++ | +++ |
| 180. | [structure] | C19H16ClN7OS 425.89 | A1 | 97.32 | ++ | +++ | +++ |

TABLE 1-continued
Exemplary invention compounds and the illustrative results of cell viability on A549 cells
| # | Structure | Formula / MW | Method | % | | |
|---|---|---|---|---|---|---|
| 181. | 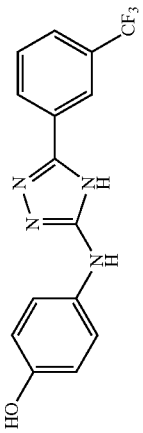 | C15H11F3N4O 320.27 | Core synthesis | 93.97 | +++ | +++ | +++ |
| 182. | 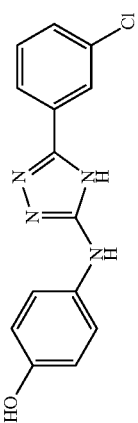 | C14H11ClN4O 286.72 | Core synthesis | 97.45 | +++ | +++ | +++ |
| 183. | 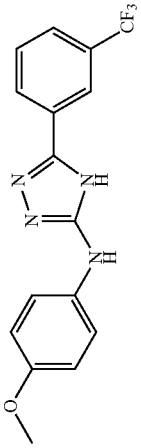 | C16H13F3N4O 334.30 | Core synthesis | 99.74 | +++ | +++ | +++ |
| 184. | 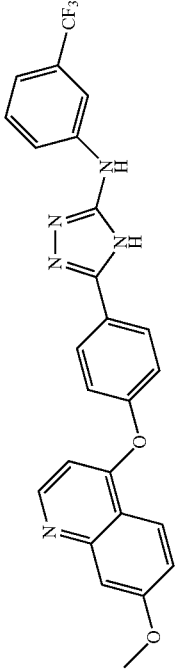 | C25H18F3N5O2 477.44 | A1 | 96.53 | ++ | +++ | +++ |
| 185. | 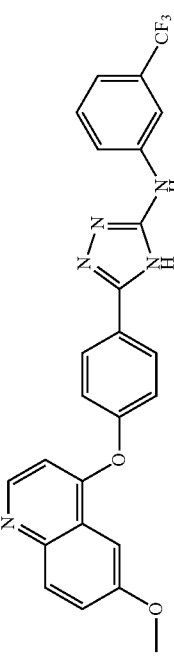 | C25H18F3N5O2 477.44 | A1 | 97.95 | +++ | +++ | +++ |
| 186. | 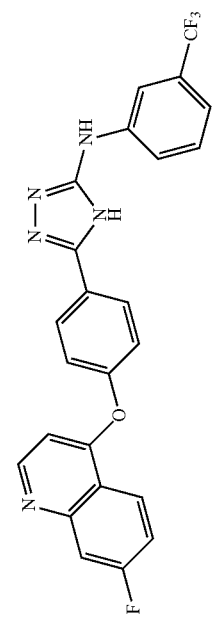 | C24H15F4N5O 465.40 | A1 | 99.67 | +++ | +++ | +++ |

TABLE 1-continued

Exemplary invention compounds and the illustrative results of cell viability on A549 cells

| # | Structure | Formula / MW | Class | % | | | |
|---|---|---|---|---|---|---|---|
| 187. | | C31H22F3N5O2 553.53 | A1 | 99.79 | +++ | +++ | +++ |
| 188. | | C26H20F3N5O2 491.46 | A1 | 96.96 | +++ | +++ | +++ |
| 189. | | C25H15F3N6O 472.42 | A1 | 99.54 | +++ | +++ | +++ |
| 190. | | C26H21F3N6O 490.48 | A1 | 97.65 | ++ | +++ | +++ |

TABLE 1-continued

Exemplary invention compounds and the illustrative results of cell viability on A549 cells

| | | | | | | |
|---|---|---|---|---|---|---|
| 191. | (structure) | C25H18F3N5O2 477.44 | A1 | 98.80 | +++ | +++ | +++ |
| 192. | (structure) | C24H15F4N5O 465.40 | A1 | 98.96 | +++ | +++ | +++ |
| 193. | (structure) | C31H22F3N5O2 553.53 | A1 | 96.51 | +++ | +++ | +++ |
| 194. | (structure) | C26H20F3N5O2 491.46 | A1 | 98.87 | +++ | +++ | +++ |

TABLE 1-continued

Exemplary invention compounds and the illustrative results of cell viability on A549 cells

| | Structure | Formula / MW | | Value | | | |
|---|---|---|---|---|---|---|---|
| 195. | | C25H15F3N6O 472.42 | A1 | 99.57 | +++ | +++ | +++ |
| 196. | | C26H21F3N6O 490.48 | A1 | 98.74 | ++ | +++ | +++ |
| 197. | | C26H20F3N5O2 491.46 | A1 | 95.06 | +++ | +++ | +++ |
| 198. | | C24H18ClN5O2 443.89 | A1 | 97.88 | +++ | +++ | +++ |
| 199. | | C21H17F3N6OS 458.46 | A1 | 98.86 | + | + | + |

TABLE 1-continued

Exemplary invention compounds and the illustrative results of cell viability on A549 cells

| | Structure | Formula / MW | | | |
|---|---|---|---|---|---|
| 200. | | C26H19F3N4O2 476.45 | A1 | 98.05 | +++ |
| 201. | | C19H15F3N8O 428.37 | | | +++ |
| 202. | | C19H14F3N7O 413.36 | | | +++ |
| 203. | | C22H20F3N7O3 487.43 | | | +++ |

TABLE 1-continued

Exemplary invention compounds and the illustrative results of cell viability on A549 cells

| # | Structure | Formula / MW |
|---|---|---|
| 204. | | C22H19F3N6O3  472.42 |
| 205. | | C21H18F3N7O2  457.41 |
| 206. | | C21H17F3N6O2  442.39 |
| 207. | | C23H22F3N7O2  485.46 |

TABLE 1-continued

Exemplary invention compounds and the illustrative results of cell viability on A549 cells

| # | Structure | Formula / MW |
|---|---|---|
| 208. | (structure) | C23H21F3N6O2 470.45 |
| 209. | (structure) | C20H13F6N7O2 497.35 |
| 210. | (structure) | C20H12F6N6O2 482.34 |
| 211. | (structure) | C20H15F3N6O 412.37 |

TABLE 1-continued
Exemplary invention compounds and the illustrative results of cell viability on A549 cells
| | | |
|---|---|---|
| 212. | 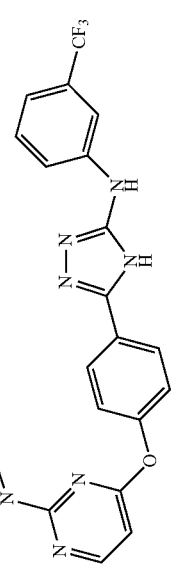 | C23H20F3N7O 467.45 |
| 213. | 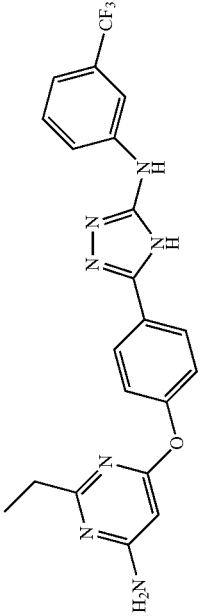 | C21H18F3N7O 441.41 |
| 214. | 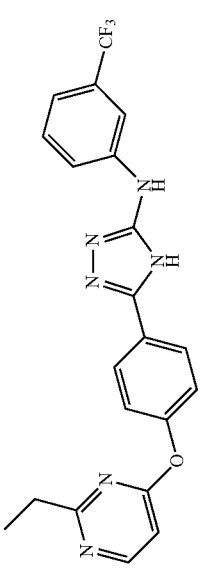 | C21H17F3N6O 426.39 |
| 215. | 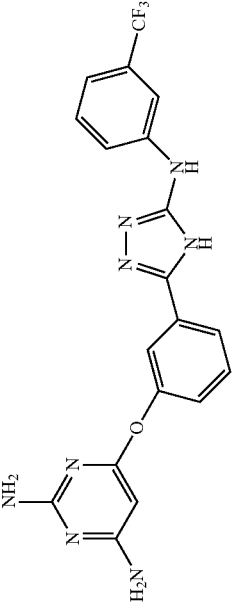 | C19H15F3N8O 428.37 |

TABLE 1-continued
Exemplary invention compounds and the illustrative results of cell viability on A549 cells
| | | |
|---|---|---|
| 216. | 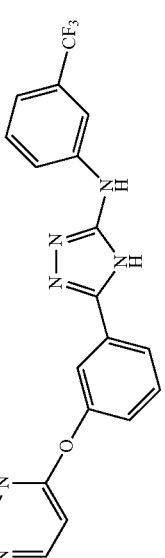 | C19H14F3N7O<br>413.36 |
| 217. | 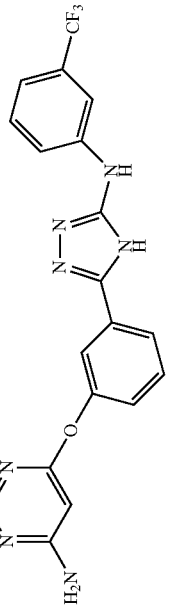 | C22H20F3N7O3<br>487.43 |
| 218. | 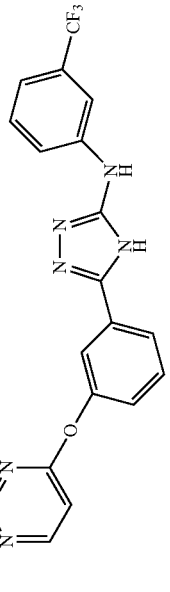 | C22H19F3N6O3<br>472.42 |

TABLE 1-continued
Exemplary invention compounds and the illustrative results of cell viability on A549 cells
| 219. | 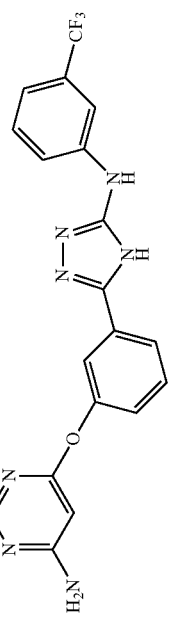 | C21H18F3N7O2 457.41 |
| --- | --- | --- |
| 220. | 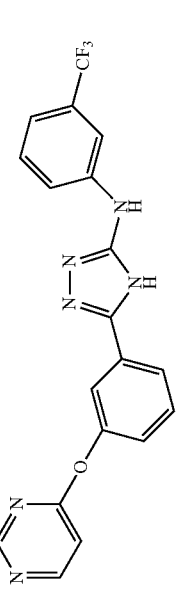 | C21H17F3N6O2 442.39 |
| 221. | 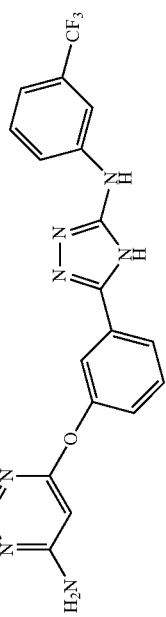 | C23H22F3N7O2 485.46 |

TABLE 1-continued
Exemplary invention compounds and the illustrative results of cell viability on A549 cells
| | | |
|---|---|---|
| 222. |  | C23H21F3N6O2<br>470.45 |
| 223. |  | C20H13F6N7O2<br>497.35 |
| 224. |  | C20H12F6N6O2<br>482.34 |
| 225. |  | C20H15F3N6O<br>412.37 |

TABLE 1-continued

Exemplary invention compounds and the illustrative results of cell viability on A549 cells

| No. | Structure | Formula / MW |
|---|---|---|
| 226. | (pyrrolidine-pyrimidine-O-phenyl-triazole-NH-phenyl-CF3) | C23H20F3N7O 467.45 |
| 227. | (4-amino-2-ethylpyrimidine-O-phenyl-triazole-NH-phenyl-CF3) | C21H18F3N7O 441.41 |
| 228. | (2-ethylpyrimidine-O-phenyl-triazole-NH-phenyl-CF3) | C21H17F3N6O 426.39 |
| 229. | (2-methylamino-quinazoline-O-phenyl-triazole-NH-phenyl-CF3) | C24H18F3N7O 477.44 |

TABLE 1-continued

Exemplary invention compounds and the illustrative results of cell viability on A549 cells

| | | |
|---|---|---|
| 230. | (structure) | C23H16F3N7O 463.41 |
| 231. | (structure) | C24H18F3N7O 477.44 |
| 232. | (structure) | C23H16F3N7O 463.41 |
| 233. | (structure) | C24H18F3N7OS 509.51 |

TABLE 1-continued
Exemplary invention compounds and the illustrative results of cell viability on A549 cells
| | | |
|---|---|---|
| 234. | 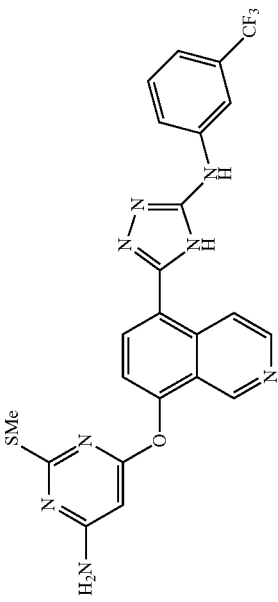 | C23H17F3N8OS 510.49 |
| 235. | 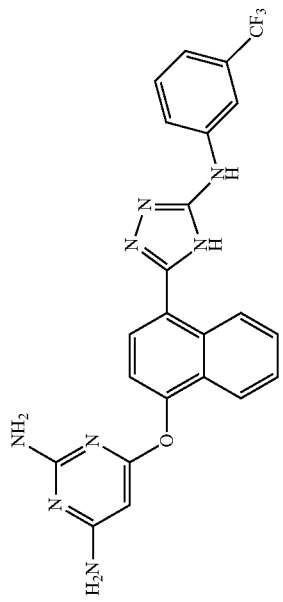 | C23H17F3N8O 478.43 |
| 236. | 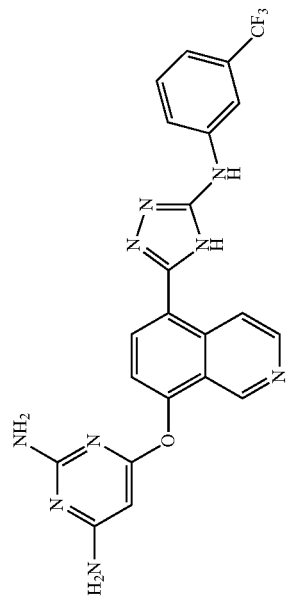 | C22H16F3N9O 479.42 |

TABLE 1-continued
Exemplary invention compounds and the illustrative results of cell viability on A549 cells
| 237. | 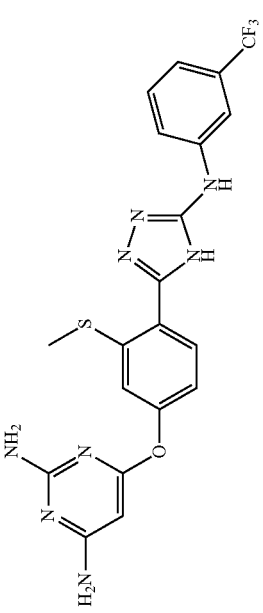 | C20H17F3N8OS 474.46 |
| --- | --- | --- |
| 238. | 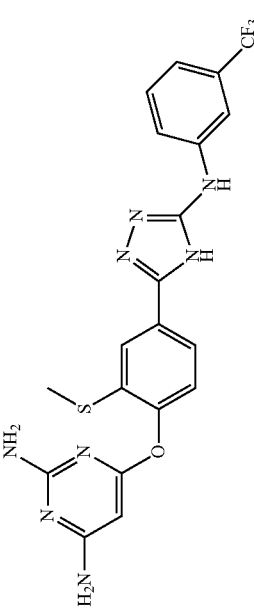 | C20H17F3N8OS 474.46 |
| 239. | 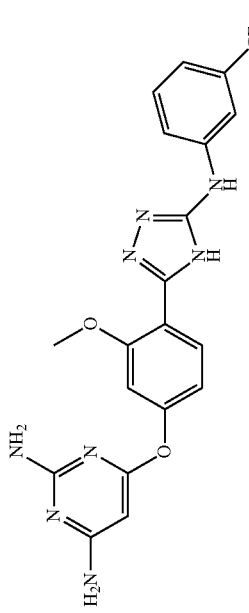 | C20H17F3N8O2 458.40 |

TABLE 1-continued
Exemplary invention compounds and the illustrative results of cell viability on A549 cells
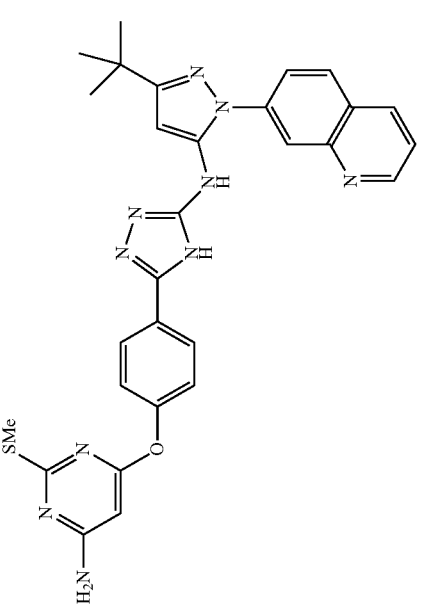
240. C20H17F3N8O2
458.40
241. C29H28N10OS
564.66

TABLE 1-continued
Exemplary invention compounds and the illustrative results of cell viability on A549 cells
| 242. | 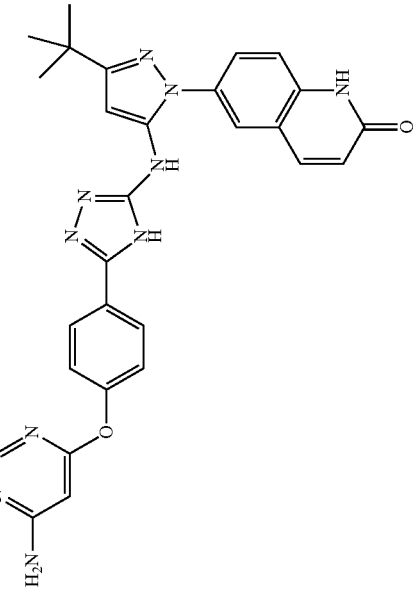 C29H28N10O2S 580.66 |
| 243. | 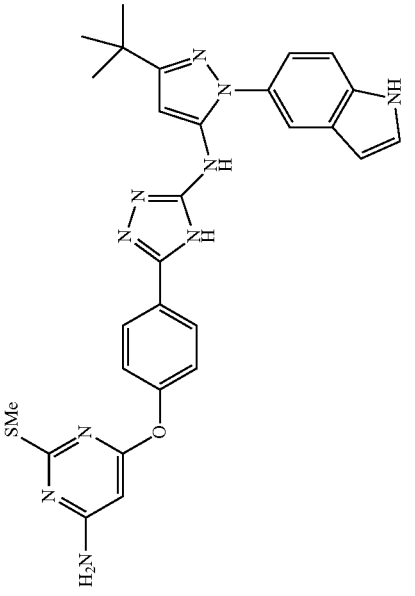 C28H28N10OS 552.65 |
| 244. | 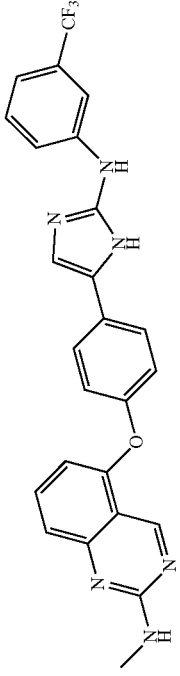 C25H19F3N6O 476.45 |

TABLE 1-continued

Exemplary invention compounds and the illustrative results of cell viability on A549 cells

| # | Structure | Formula / MW |
|---|---|---|
| 245. | | $C_{24}H_{17}F_3N_6O$ 462.43 |
| 246. | | $C_{25}H_{19}F_3N_6O$ 476.45 |
| 247. | | $C_{19}H_{10}D_4F_3N_7O$ 417.38 |
| 248. | | $C_{19}D_{14}F_3N_7O$ 427.44 |
| 249. | | $C_{20}H_9D_7F_3N_7OS$ 466.49 |

TABLE 1-continued
Exemplary invention compounds and the illustrative results of cell viability on A549 cells
| | | |
|---|---|---|
| 250. |  | C19H10D4F3N7O2<br>433.38 |
| 251. |  | C19H5D9F3N7O2<br>438.41 |
| 252. |  | C20H12D3F3N6OS2<br>479.52 |
| 253. |  | C20H7D8F3N6OS2<br>484.55 |

TABLE 1-continued

Exemplary invention compounds and the illustrative results of cell viability on A549 cells

| Compound | Structure | Formula Mol. Wt. | Method of synthesis | % Purity (HPLC) | % Viability A549 (μm) >10: *** 1-10: ** <1.0: * |
|---|---|---|---|---|---|
| 254. | 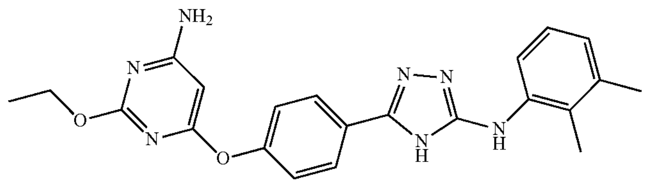 [SMILES: CCOc1nc(N)cc(Oc2ccc(-c3nnc(Nc4cccc(C)c4C)[nH]3)cc2)n1] | C22H23N7O2 417.46 | B | 99.2 | * |
| 255. | 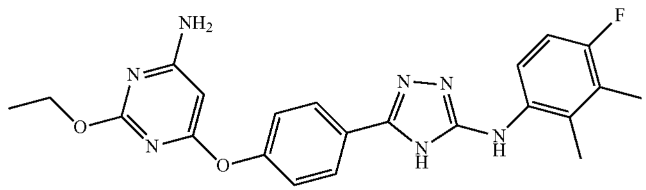 [SMILES: CCOc1nc(N)cc(Oc2ccc(-c3nnc(Nc4ccc(F)c(C)c4C)[nH]3)cc2)n1] | C22H22FN7O2 435.45 | B | 100 | * |
| 256. | 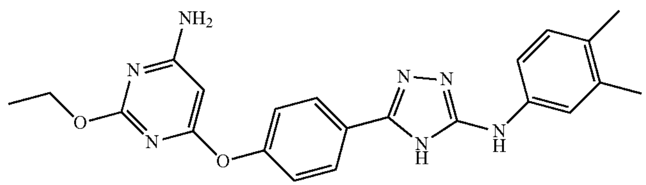 [SMILES: CCOc1nc(N)cc(Oc2ccc(-c3nnc(Nc4ccc(C)c(C)c4)[nH]3)cc2)n1] | C22H23N7O2 417.46 | B | 100 | *** |
| 257. | 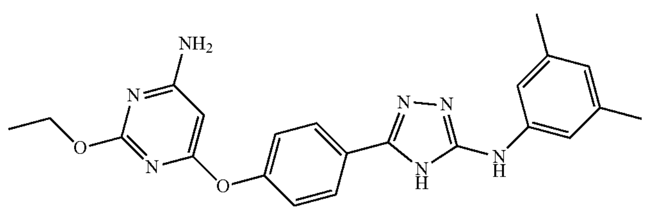 [SMILES: CCOc1nc(N)cc(Oc2ccc(-c3nnc(Nc4cc(C)cc(C)c4)[nH]3)cc2)n1] | C22H23N7O2 417.46 | B | 99.7 | * |

TABLE 1-continued

Exemplary invention compounds and the illustrative results of cell viability on A549 cells

| # | Structure | Formula / MW | | | |
|---|---|---|---|---|---|
| 258. | | C22H22ClN7O2 451.91 | B | 100 | *** |
| 259. | | C24H25N7O2 443.50 | B | 98.5 | * |
| 260. | | C20H18ClN7O2 423.86 | B | 93.8 | * |
| 261. | | C21H19N5O 357.41 | B | 97.8 | * |

TABLE 1-continued
Exemplary invention compounds and the illustrative results of cell viability on A549 cells
| | | | | |
|---|---|---|---|---|
| 262. | 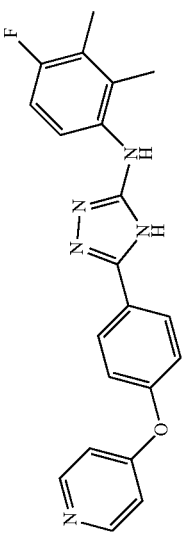 | C21H18FN5O 375.40 | B | 96.6 | * |
| 263. | 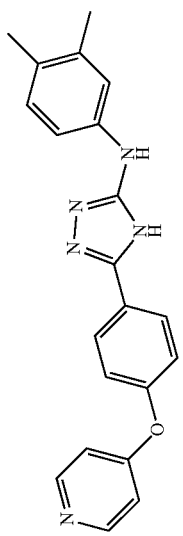 | C21H19N5O 357.41 | B | 94.1 | ** |
| 264. | 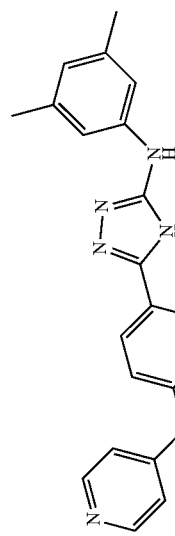 | C21H19N5O 357.41 | B | 99.3 | * |
| 265. | 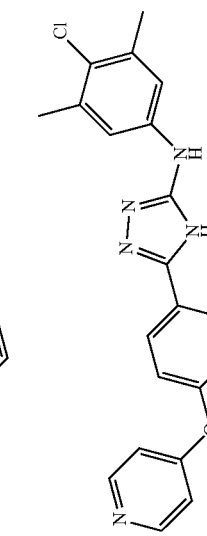 | C21H18ClN5O 391.85 | B | 99.1 | *** |
| 266. | 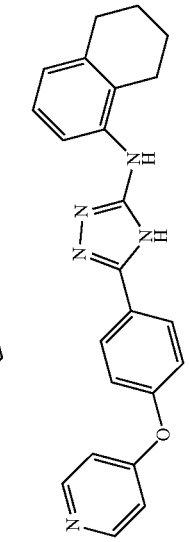 | C23H21N5O 383.45 | B | 98.1 | * |

TABLE 1-continued

Exemplary invention compounds and the illustrative results of cell viability on A549 cells

| | | | | |
|---|---|---|---|---|
| 267. | [structure] | C19H14ClN5O 363.80 | B | 98.5 | ** |
| 268. | [structure] | C22H21N5O 371.44 | B | 100 | * |
| 269. | [structure] | C22H20FN5O 389.43 | B | 98.0 | * |
| 270. | [structure] | C22H21N5O 371.44 | B | 100 | ** |
| 271. | [structure] | C22H21N5O 371.44 | B | 100 | * |

TABLE 1-continued
Exemplary invention compounds and the illustrative results of cell viability on A549 cells
| | | | | |
|---|---|---|---|---|
| 272. | 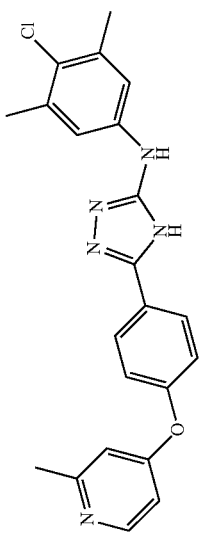 | C22H20ClN5O 405.88 | B | 98.1 | ** |
| 273. | 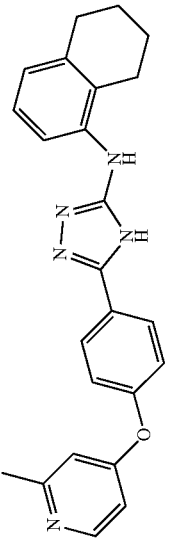 | C24H23N5O 397.47 | B | 96.1 | * |
| 274. | 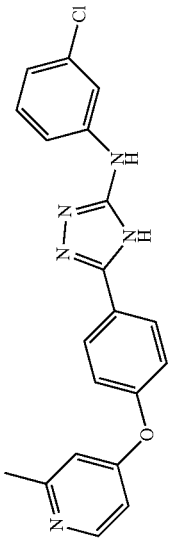 | C20H16ClN5O 377.83 | B | 94.9 | * |

What is claimed is:

1. A compound having the structure (IV) or an N-oxide, N,N'-dioxide, N,N',N''-trioxide, or a pharmaceutically acceptable salt thereof:

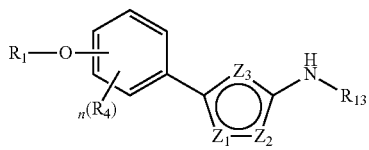

(IV)

wherein:

$Z_1$ and $Z_2$ are N;

$Z_3$ is $NR_5$, wherein $R_5$ is hydrogen or an unsubstituted $C_1$-$C_6$ alkyl;

$R_1$ is a $C_6$ heteroaryl having 1 or 2 nitrogens optionally substituted with alkylthio or amino;

$R_4$ is independently selected from a group consisting of hydrogen, halogen, and an unsubstituted $C_1$-$C_6$ alkyl;

n is 1 or 2; and $R_{13}$ is selected from a group consisting of the following structures:

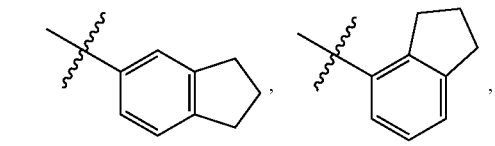

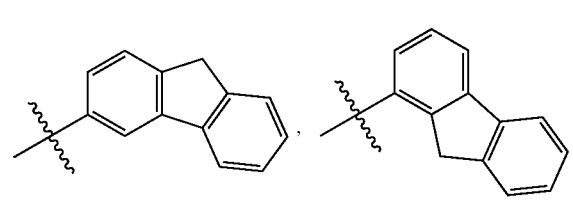

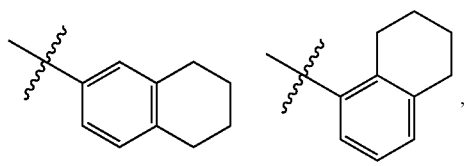

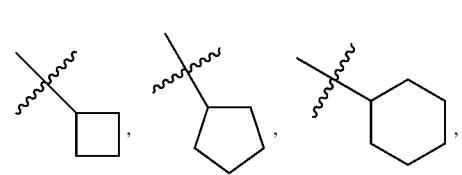

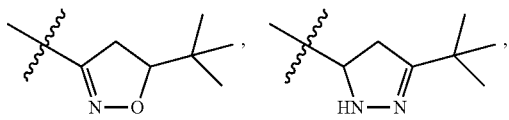

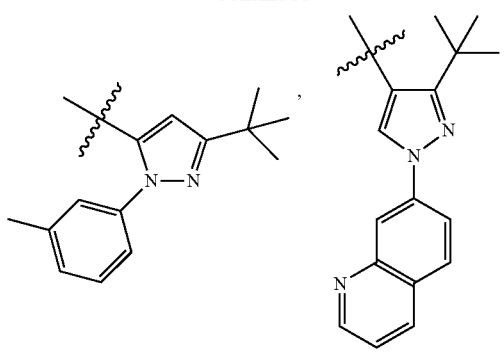

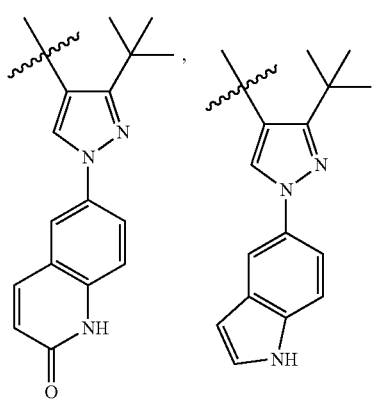

2. The compound of claim 1, wherein the compound having structure (IV) is selected from the group consisting of

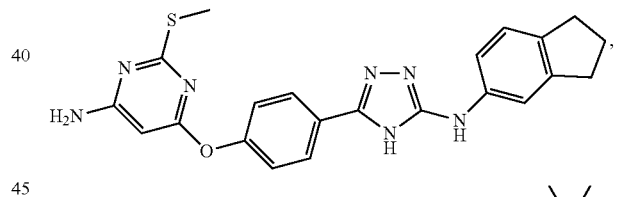

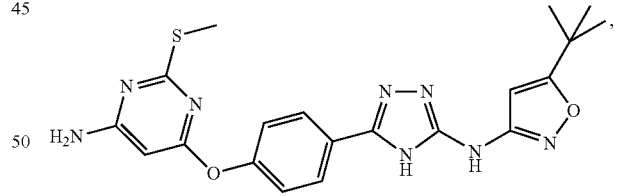

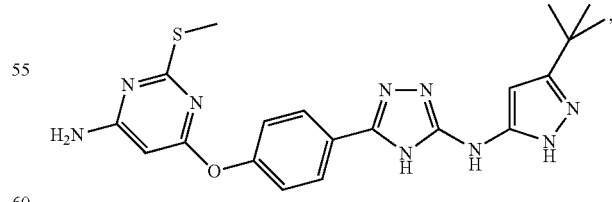

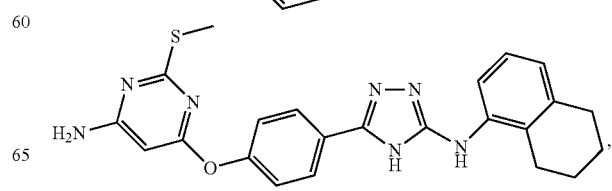

-continued
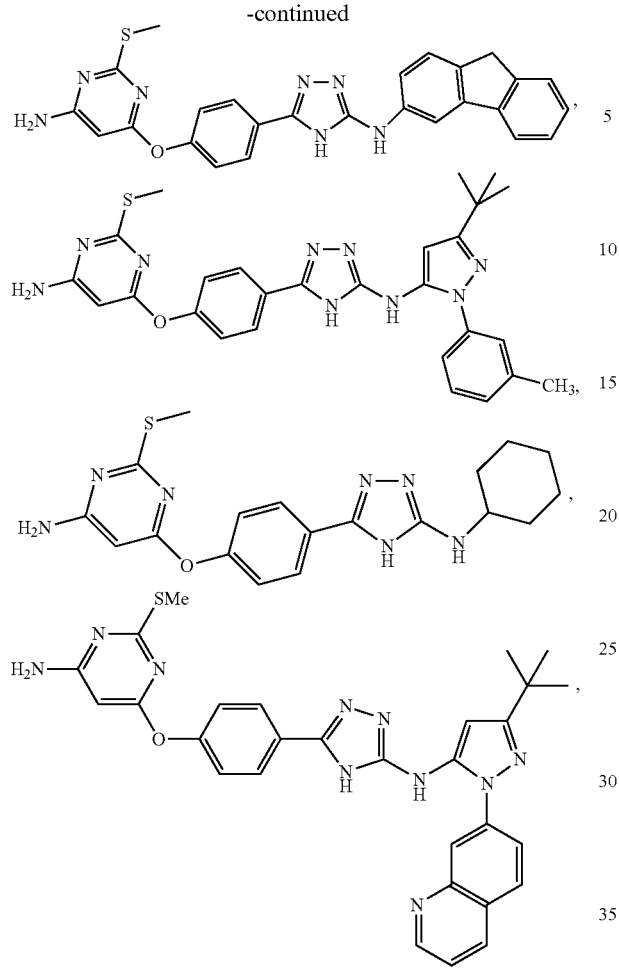
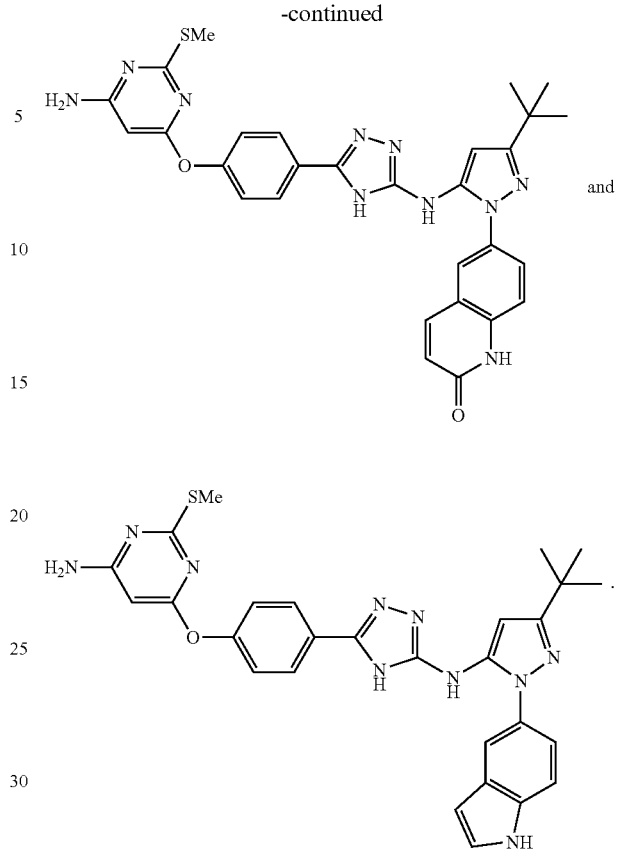
3. A pharmaceutical composition comprising a compound of claim 1, in a pharmaceutically acceptable carrier.
* * * * *